United States Patent [19]
Ohno et al.

[11] Patent Number: 5,763,188
[45] Date of Patent: Jun. 9, 1998

[54] PROBE FOR DIAGNOSING *ESCHERICHIA COLI, KLEBSIELLA PNEUMONIEAE* OR *ENTEROBACTER CLOACAE*

[75] Inventors: Tsuneya Ohno, Tokyo; Akio Matsuhisa, Nara; Hirotsugu Uehara, Kobe; Soji Eda, Higashi-Osaka, all of Japan

[73] Assignees: Tsuneya Ohno, Tokyo; Fuso Pharmaceutical Industries, Ltd., Osaka, both of Japan

[21] Appl. No.: 920,812

[22] Filed: Aug. 29, 1997

Related U.S. Application Data

[62] Division of Ser. No. 362,577, filed as PCT/JP93/00936 Jul. 7, 1993.

[30] Foreign Application Priority Data

Jul. 7, 1992 [JP] Japan .................................. 4-179719

[51] Int. Cl.[6] .............................. C12Q 1/68; C07H 21/04
[52] U.S. Cl. .......................... 435/6; 536/23.1; 536/23.7; 536/24.32; 935/8; 935/9; 935/78
[58] Field of Search ........................ 435/6; 536/24.32, 536/23.1, 23.7; 935/8, 9, 78

[56] References Cited

FOREIGN PATENT DOCUMENTS 0297807  1/1989  European Pat. Off. .

OTHER PUBLICATIONS

Eick–Helmerich et al. "Import of Biopolymers into *Escherichia coli*: Nucleotide Sequences of the exbB and exbD Genes Are Homologous to Those of the tolQ and tolR Genes, Respectively" J. Bacterial. 171:5117–5126 (Sep. 1989).
Alberts et al., *Molecular Biology of the Cell*, Second Edition, Garland Publishing Inc., New York, NY, pp. 182 and 188–193 (1989).
Bell, et al., "The Nucleotide Sequences of the rbsD, rbsA, and rbsC Genes of Escherichia coli K12", *The Journal of Biological Chemistry* 261(17):7652–7658 (Jun. 1986).
Betzl, et al., "Identification of Lactococci and Enterococci by Colony Hybridization with 23S rRNA–Targeted Oligonucleotide Probes", *Applied and Environmental Microbiology*: 56(9):2927–2929 (Sep. 1990).
Buckel, et al., "An Analysis of the Structure of the Product of the rbsA Gene of Escherichia coli D12", *The Journal of Biological Chemistry* 261(17):7659–7662 (Jun. 1986).
Cano et al., *Microbiology*, West Publishing Company, Minneapolis, MN, pp. 264–268, 279, 293, 296, 297, and 801 (1986).
Davis, et al., "Direct Identification of Bacterial Isolates in Blood Cultures by Using a DNA Probe", *Journal of Clinical Microbiology* 29(10):2193–2196 (Oct. 1991).
De Buyser, et al., "Evaluation of a ribosomal RNA gene probe for the identification of species and subspecies within the genus Staphylococcus", *Journal of General Microbiology* 138:889–899 (1992).
Gerberding et al. Antimicrobial Agents and Chemotherapy 35(12):2574–2579 (1991).
Groarke, et al., "The Amino Acid Sequence of D–Ribose–binding Protein from Escherichia coli K12", *The Journal of Biological Chemistry* 258(21):12952–12956 (1983).
Hall, et al., "Typing of Enterococcus Species by DNA Restriction Fragment Analysis", *Journal of Clinical Microbiology* 30(4):915–919, (Apr. 1992).
Hope, et al., "Ribokinase from Escherichia coli K12", *The Journal of Biological Chemistry* 261(17):7663–7668 (Jun. 1986).

(List continued on next page.)

*Primary Examiner*—Carla J. Myers
*Attorney, Agent, or Firm*—Marshall, O'Toole, Gerstein, Murray & Borun

[57] ABSTRACT

DNA probes for diagnosing infectious diseases involving *Escherichia coli*, *Klebsielkli pneunmoniae* or *Enterobacter cloacae* and methods of using such probes are provided.

2 Claims, 6 Drawing Sheets

OTHER PUBLICATIONS

Joffee, et al., "Epidemiologic Studies of Nosocomial Infections with *Pseudomonas aeruginosa* Using a DNA Probe", *Abstracts of the Annual Meeting*:485 (1989).

Lehninger, A.L., *Principles of Biochemistry*, Worth Publishers, Inc., New York, pp. 809–811 (1982).

Maniatis et al., *Molecular Cloning: A Laboratory Manual*, Cold Spring Harbor Laboratory, Cold Spring Harbor, NY, pp. 309–330, 374 and 375 (1982).

Sambrook et al., *Molecular Cloning : A Laboratory Manual*, Second Edition, Cold Spring Harbor Laboratory Press, Cold Spring Harbor, NY, pp. 5.10, 5.11, and 12.21–12.23 (1989).

Smith et al., *Principles of Biochemistry: General Aspects*, Seventh Edition, McGraw–Hill Book Company, New York, NY, p. 723 (1983).

Tredget, et al., "Epidemiology of Infections with *Pseudomonas aeruginose* in Burn Patients: The Role of Hydrotherapy", *Clinical Infectious Diseases* 15:941–949, (1992).

Watson et al., *Molecular Biology of the Gene*, Fourth Edition, The Benjamin/Cummings Publishing Company, Inc., Menlo Park, CA, pp. 89, 208–210, and 608 (1987).

Watson et al., *Recombinant DNA: A Short Course*, Scientific American Books, USA, pp. 58–60 (1983).

Bell et al. Journal of Biological Chemistry. 261:7652–7658, 1986.

Eick–Helmerich. Journal of Bacteriology. 171:5117–5126, 1989.

Burland et al. Genomics. 16:551–561, 1993.

Schnetz et al. Journal of Bacteriology. 169:2579–2590, 1987.

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 8959 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus aureus
        ( B ) STRAIN: Clinical Isolate SA-7

( x i ) SEQUENCE DESCRIPTION: SEQ ID NO:1:

```
AAGCTTTATC TGCTGAATAT ACCGCATTTT TTATCTTGTT AATTGTCGGC ACATTTCTT     60
CAATAGTTAA ACCTGCTTTG TTAGCTTCTT CTAATAATGC TCGAGTTACT GTTTATTAAA   120
TGTTCATTCG CTTTTCAACG ACAACTGACG AACCAGTATC TGTTAGCTTA GACGCAACAG   180
CGTTAATCTT CTGATTCACC TTAAATTCTA CATCTGCTTT TTGAGGCTGC TTACGTAGTG   240
TCCCGGTAAT TTCATGTGTA AACTTAGATG GGATGTAAAT ACCTGCAAAA TATTTACCCA   300
TTTTTATCTC ATGATCAGCT TTCTCTCTAC TTACAAACTG CCAATCAAAA CTTTTATTTT   360
TCTTGAGTGT ATTAACCATC GTATTACCGA CATTAACTTT TTCCCTCTG ATTGTGTCGC    420
CTTTATCTTC ATTAACGACT GCGACCTTGA TGTGTCCCGT GTTGCCATAT GGATCCCACA   480
TTGCCCATAA GTTAAACCAA GCGTAGAACG ATGGCAAAAT AGCTAAGCCT GCTAAGATAA   540
TCCACACAGC TGGCGTCTTA GCTACTTTCT TCAGATCCAT TTTAAATAAT TTAAATGCGT   600
TCTTCATTGT CACACTCCTA TGTAGGAATT ATTCATATTT TTTATATATT TTTTGTAAAT   660
TAATTTATTT TTGCGTTGTG AATTAGTATA ATCAATTTAC TGGAAGATAT TTAGTCGATT   720
GATACCTATC AACTATTTTC AGCATACGAT AAATTATAAC AAATCATAGT TTATTATCAC   780
ACTTAATTAT TATATTTTTC AAGGGAGAAT ACGAAATATG CCTAAAAATA AAATTTTAAT   840
TTATTTGCTA TCAACTACCC TCGTATTACC TACTTTAGTT TCACCTACCG CTTATGCTGA   900
TACACCTCAA AAAGATACTA CAGCTAAGAC AACATCTCAT GATTCAAAAA AATCTAATGA   960
CGATGAAACT TCTAAGGATA CTACAAGTAA AGATACTGAT AAAGCAGACA CAATAATAC   1020
AAGTAACCAA GACAATAACG ACAAAAAATT TAAAACTATA GACGACAGCA CTTCAGACTC  1080
TAACAATATC ATTGATTTTA TTTATAAAGA ATTACCACA AACCAATATA AACCAATTGC   1140
TAACCAAAAA TAAATACGAT GATAATTACT CATTAACAAC TTTAATCCAA AACTTATTCA  1200
ATTTAAATTC GGATATTTCT GATTACGAAC AACCTCGTAA TGGCGAAAAG TCAACAAATG  1260
ATTCGATAAA AACAGTGACA TAGCATCAAA AATGACACTG ATACGCAATC ATCTAAACAA  1320
GATAAAGCAG ACAATCAAAA AGCACCTAAA TCAAACAATA CAAAACCAAG TACATCTAAT  1380
AAGCAACCAA ATTCGCCAAA GCCAACACAA CCTAATCAAT CAAATAGTCA ACCAGCAAGT  1440
GACGATAAAG CAAATCAAAA ATCTTCATCG AAAGATAATC AATCAATGTC AGATTCGGCT  1500
TTAGACTCTA TTTTGGATCA ATACAGTGAA GATGCAAAGA AAACACAAAA AGATTATGCA  1560
TCTCAATCTA AAAAAGACAA AAATGAAAAA TCTAATACAA AGAATCCACA GTTACCAACA  1620
CAAGATGAAT TGAAACATAA ATCTAAACCT GCTCAATCAT TCAATAACGA TGTTAATCAA  1680
```

```
AAGGATACAC GTGCAACATC ATTATTCGAA ACAGATCCTA GTATATCTAA CAATGATGAT  1740
AGCGGACAAT TTAACGTTGT TGACTCAAAA GATACACGTC AATTTGTCAA ATCAATTGCT  1800
AAAGATGCAC ATCGCATTGG TCAAGATAAC GATATTTATG CGTCTGTCAT GATTGCCCAA  1860
GCAATCTTAG AATCTGACTC AGGTCGTAGT GCTTAGCTA AGTCACCAAA CCATAATTTA  1920
TTCGGTATCA AAGGTGCTTT TGAAGGGAAT TCTGTTCCTT TTAACACATT AGAAGCTGAT  1980
GGTAATAAAT TGTATAGTAT TAATGCTGGA TTCCGAAAAT ATCCAAGCAC GAAAGAATCA  2040
CTAAAAGATT ACTCTGACCT TATTAAAAAT GGTATTGATG GCAATCGAAC AATTTATAAA  2100
CCAACATGGA AATCGGAAGC CGATTCTTAT AAAGATGCAA CATCACACTT ATCTAAAACA  2160
TATGCTACAG ATCCAAACTA TGCTAAGAAA TTAAACAGTA TTATTAAACA CTATCAATTA  2220
ACTCAGTTTG ACGATGAACG CATGCCAGAT TTAGATAAAT ATGAACGTTC TATCAAGGAT  2280
TATGATGATT CATCAGATGA ATTCTGTTCC TTTTAACACA TTAGAAGCTG ATGGTAATAA  2340
ATTGTATAGT ATTAATGCTG GATTCCGAAA ATATCCAAGC ACGAAAGAAT CACTAAAAGA  2400
TTACTCTGAC CTTATTAAAA ATGGTATTGA TGGCAATCGA ACAATTTATA AACCAACATG  2460
GAAATCGGAA GCCGATTCTT ATAAAGATGC AACATCACAC TTATCTAAAA CATATGCTAC  2520
AGATCCAAAC TATGCTAAGA AATTAAACAG TATTATTAAA CACTATCAAT TAACTCAGTT  2580
TGACGATGAA CGCATGCCAG ATTTAGATAA ATATGAACGT TCTATCAAGG ATTATGATGA  2640
TTCATCAGAT GAATTCAAAC CTTTCCGCGA GGTATCTGAT AGTATGCCAT ATCCACATGG  2700
CCAATGTACT TGGTACGTAT ATAACCGTAT GAAACAATTT GGTACATCTA TCTCAGGTGA  2760
TTTAGGTGAT GCACATAATT GGAATAATCG AGCTCAATAC CGTGATTATC AAGTAAGTCA  2820
TACACCAAAA CGTCATGCTG CTGTTGTATT TGAGGCTGGA CAATTTGGTG CAGATCAACA  2880
TTACGGTCAT GTAGCATTTG TTGAAAAAGT TAACAGTGAT GGTTCTATCG TTATTTCAGA  2940
TCAATGTTAA AGGATTAGGT ATCATTTCTC ATAGAACTAT CAATGCAGCT GCCGCTGAAG  3000
AATTATCATA TATTACAGGT AAATAAGTAT TATTAAACCC GCAAAATTTA TAAGTATAAA  3060
CAAGGAGTTC GGACTTAAAC ATATTTCTGT TCATAAGTCC GATTCTTAT TCAATTAAAC  3120
CCGAGGTATT CAGTTCGAAC GCCTCGGGTC ATTTTATATA AATATATTAT TTATGTTCA  3180
AATGTTCCTC ATCATATCCG TTTCAATTGT CATCTCACAC ATTTTATAAA TATGAGCAAA  3240
TGTACTTATT TTCAAACATT ACTGCCTAGC TTTAATTGAC GTTATATTAA CTATAAACTA  3300
CTTTTCCATG ACTCTACGGA TTCAATGTCA CATGAGCGTG ATAAAATTTG TTCAATAATA  3360
AAGTCATGTT TATCATCTGA TCTATCACCA ACAGCATCTT CTAAAACAGT AATATAATAG  3420
TCTTTATCTA CACTTTCTAA TGCCGTGCTC AATACAGCTC CACTCGTAGA GACACCCGTT  3480
AATACTAAAT GATTAATATC ATTTGCACGT AAATAAACTT CCAAGTAACT ACCTGTAAAT  3540
GCGCTAAAGC GTCGCTTAGA AATAATCGGC TCATCTTCTA GTGGTGCTAA ATCTTCAAGT  3600
ATTCGTGTAG ATGCATCTGC TTCAGTAATC GCATATCCTT GAGCTTTAAT TGTTGAAAAC  3660
ACTTTATTAC TCGAGGAGAC ATCATTAAAA TGCTTATCTA ACACTAAACG TATGAAAATG  3720
ACTGGTATTC GATGTTGTCT TGCTGCTTCA ATTGCTCTCT GATTCGCTTT AATAATATTT  3780
TTATTCTAG GTACACTACT CGCTATACTT CTTGCATATC CAAACTAATA GCGCCGTTTT  3840
TCGAGACATC TTCATTCTCC TTTACTTCTG TAGTTCTAAG TCGTTAAATT CATTATAACG  3900
TTAAAATGAT GGACAATCTA TTCATTGCAT TTTGCATATA CTTCACAATA ATTTAAGGGG  3960
GAAATAAGAC GTCTTATATA CTTAAAAAAA TATATAGATG CTCTTCCCCC AATATAATTA  4020
TGCTTTATTT TTCAACTTAT TGCGTCGTGA TAACCAAATC ATTAGTACAC CCATTGCACC  4080
```

| | | | | | |
|---|---|---|---|---|---|
| AACAATTACA | GATATCGGCA | ACCAATGTTC | TTTTATCGTT | TCCCCGCTTT | AGGCAAGATA | 4140
| CATTACCATC | AGCATTTAAT | AATCCACTTA | ACAATCCATT | ACCTTTACCA | AGTGTTACGT | 4200
| CTTTTCTGGC | TTTGGTGTGG | GTATATCTGG | AATACTGTCT | AATAAATTTG | ATCCTTGATT | 4260
| CATTAAATTT | GCTAACTTAT | TTAAATCCGT | TGTTTTCCCA | TTTTTATTCA | ATCGATCTAG | 4320
| TAAACTTGGA | CGATTTACTA | TTGGTGATAA | AATATAGTCT | ATATCTTTTT | TCGTTTGATT | 4380
| GAGTCTCTTT | TGTAAATTCA | ATAAATCATC | CGCTTTACCA | TTCAATGCCG | ATTTAACTAA | 4440
| ATTAAAAATT | TTATTTTGAT | CTGTTTCTAT | TTTAGTAATT | AAATCTGCCA | GTAATTTTGC | 4500
| CTTTTGTCTT | TCTATACGTG | TTGCTAAAAT | CGTTTCAATT | GCTTGCTTTT | TATCTTTGGC | 4560
| ATTATTCAAA | ATTGCTTTTA | ATATATCATC | TGAAGACGTG | TCGCCAGTTG | ATGCAAAATG | 4620
| TTTCTTCAAT | TGGTCAACGA | TTTGGCGATT | TGATAATCCT | TTATTCGTCC | AATCTTTAGC | 4680
| CAATTTATCT | GCTTCAGCTT | TTCCTAATTT | CGTTTGTAAG | ATTTGAGAAA | TCAATAGCGA | 4740
| CTTATCTTGT | GATTGATCAA | TCAATGACGT | TAATAAATCA | TCACTCGTTG | TCAGAGATAG | 4800
| TTGATCAATA | TGACGAGTAA | TTTGATCTGC | AATTTGTTGA | TCTGTTTTAC | CATCAACACG | 4860
| TATATCTTTT | AGAATTTTAT | CTGCCTCGTC | TTTATTAAAT | ATACTTTCTA | AAATGCTTTG | 4920
| TGTAGCATAC | TTTTTATCAT | CAGTACGTGC | AAGTTCTTCC | AAAATAATAT | TTCGTTGACT | 4980
| TTTTATACGC | TCTTTCGTCT | TATTTACTTC | GCTCATTAAG | TCTGATTTTT | GATTTTAGG | 5040
| AAGTTGCGTA | TTTGCAATAC | GTTGATCTAA | AGATTGTAAC | GTATTCAGTT | TATGATATGT | 5100
| GTAATGTTGC | GTTGAGGCAT | TACTTTTAGC | CAATTTTTCA | ATCATAGCAT | GATTAATTTT | 5160
| ATCGCTTCCT | TGTAATTTAT | CAGTGAGTTG | ATTACTATGG | CTTTGATTCT | CTTCATTTGA | 5220
| AAGAAATTTA | TTAACACAA | CATGTCCAGA | ACCATCATTA | TTTGGCGTTT | TAGCTACTTC | 5280
| ATGATTACTA | TCTGTTGTAG | ACACTGCCGG | ATCTTTCGAT | GCATCTTTCA | ATGCATCTTT | 5340
| CGATTTGTGT | ATTTGCTGAT | TCAAATGGTC | TAGGTCTTCT | AACGCCTTAT | TTACCATTGC | 5400
| TTCATCATTT | TTATCATCTT | TTTCTCCATA | TTTTGTTGTA | GCCGTTTGTG | ACATATCATT | 5460
| TTTCATTGCA | TTAAGATCGT | CCTCGCCACT | TTGTTGACCC | CTATCAACAT | TGAAGAAAC | 5520
| CTCATTTAAA | TCTTTAAGCA | ATTGATCTAA | TTTACTGTCT | ATATCACTTT | GACCGTTCAT | 5580
| TTCAGTGTGA | GAACTTTTAT | TTTCTTTGCT | ATCCAACTCA | TTAGCTCGTT | TTATGATTTC | 5640
| ATCTATTTGC | GATGCTGTTT | TCGCTTCATT | TAGTTGTGCT | TTATAATGTG | CTTTAGATGA | 5700
| AGCCGATAAC | TGTTTAATT | GCTCAATTTG | ACGAATTGCT | TTGTCAACTT | TGTCTAATAA | 5760
| ATCTTGCTTA | GATAATATCT | CTTTTGAAAT | TTCAGTATCC | TTTTCAGATG | CAGCTTGGGC | 5820
| ATCGTACGGC | AAGATATTCG | TTAAAATGAT | ACTTGACGCC | ATCATTGTCG | AACACGATAA | 5880
| CTTTACATAT | AATTGAAACG | GTTTCCCTCG | ATATTTAGCC | ATCAACATAC | TCCTTTCTCA | 5940
| CTTACTTCCT | TCAAAGAATT | ACATACTATT | ATATACCTGT | TTACAAGAAA | TTTACACTTA | 6000
| TCTATCTAGT | TATTGTTGTT | AGTAATTATC | AACTTATTAC | TTAGCTTATA | TTTAAGTAAA | 6060
| CAAAAAGCA | TGACGTAATA | TCATATTGTC | CATGTCGCTA | ACATCATATT | ACGTCAAATC | 6120
| TTTTAAATTA | AATGATGCTT | TATTTTAGAC | TGCTTTTTCT | TTTTAGCTTT | CGAGCGCCTG | 6180
| TTTAAAAACT | TGCTCGAATT | GTTCACGCGA | GATTCGTGT | GCATGTGCTT | TTTGTGCTAA | 6240
| TAAAGCATCT | CGAAACTGTT | GTTGATCTTT | CAAACTTTCT | AACATTTGTA | TTAATTGGTC | 6300
| TTTACTTTCC | ATTGTTATCT | CATCATTATG | CTCAAATAAG | TGCTCTGATA | ATGTTACTTT | 6360
| AGCATGGTGT | GCGGTTTGAC | GATAACCTAA | AATCAACAAC | TCATAGTCAA | ACGCTTGTTC | 6420
| CACCGCATTT | AAAATTTCAT | TACCCTCATT | GATATCAAGA | TAAATATCAC | ATAACTGGTA | 6480

-continued

```
TAGTTCATTT ACCCTGTCAA TATAATAGAT GGTATAAGTG CACATTAGCA TATTGATCAA    6540
GTTGCATTAG CTTATCAGAC ATCTCTGTAA TAGCAGCGAT GTGAAAATTA AAATCTGGTA    6600
AAGTTTCAAC CAATACCTTG ATGTTACGAA GTTGATCCGA GTTAGTTAAT ATTACAATTT    6660
CTTTAGTATA TCTATTACGA CTACGATAGT TATATAGATA TCCGCCTTGT AAAATACGAG    6720
ATTGAACCTT TGCGTCTGCT ATATTGAGCA TCGTTTCATA TTCGTTTTTA TCTGGAATAA    6780
TAATATTACA ATGTCGTTTC ATATCACCTT TACACATCAA TTGCATATTT CCCGGGACAT    6840
TACCATTACA GTGTTCTTGC CATACCAAAA CATCACTACC TTTGATGGC AAATTATATA     6900
ACACTGAAAA TGGTAGGGCT AGTGAGTTAA TAACGAAATG ATGTTCCGTA ATTTCAAGTT    6960
GCTTGATAAA AAATAATACG AATGCGAGCT TGAAGGGAA AAAGTAAGAC TTCCCTTGCC     7020
AATCCAATAT GACATCAGAT GTTACAAAAT TTTCATAAAT CACTTCTTTA CCTTCTGCTG    7080
TCATATATTT CTTCAAGATC GCTTTACGAT TTAAATCGTA ACAGTTTGTG CAATTTAATA    7140
CCATTCTTAG AATAATAATC GACAAATCGG ACACGTTGTT GGTCATCAAA CCATTCGACA    7200
CGACTAACAA TTCTAGGGCG CTCTCCACTT TGATAAAATA TTTTGCCTCG TAGACGTCCC    7260
ATATCATTAA TTGTAGCCGA ATTGTTGTTA CCTTTAATTT CCCAAAAAGC TGGTACAGTA    7320
ACCTGATTAA AAAATCGTGG TTTCATATTT TCTGTATTAT GATTATCTGC AAAAAATTGA    7380
TACGGTGATA TAACATCGTC CGGTAAAAAG CCATTGTCAT TGAGTACAAT TGTTAAATCT    7440
TCTTCCAACT TACTGGCTTT AAAAGACTCA TATAACTTTC GTGAATGATC GTTAAAGTAA    7500
TCAAATAATT TAATCATGTA GCACCTCTTG AACTAATGTT TCCCATTTTA AAATAATATC    7560
TTGAGTCATA AATTGCTGTG CCACTTCATA AGAGATGTCA TGTGGTGCCT GGGGACCATT    7620
GTTAAAATAC ATTACAATGG CATGAGCTAG TTTGCGATA ACATCATCCA CACTATCTTC     7680
GTCGGTATCA AAAGGTACCA AGTAGCCATT TTCCCCATCT CGAATAAAGG TTGGGTTACC    7740
ATAATTCACA TTTAATCCAA TCATACCTAG TCCTGAGCCT ACCGCTTCCA TTAGTGTTAA    7800
CCCAAAACCT TCGCTAGTTG ATGCAGAAAG AAATAACTCA TAATCATTAT AAATTTCATC    7860
AAGTTTAACA TGCCCTTAGT AAACCGAATA TAATCTTGTG CGCGGTGTGT ATCAATAATT    7920
TTACGCAGTC GCGTCTTCTC GCTACCTTCT CCATAAATAT CAAATGTTAA TTCTGGCACT    7980
TGTCGTTTAG CCACGATAAC CGCCTTGACA AGCCAATCAA TATGTTCTC ATTTGCTAAA     8040
CGAGATGCAC TAATCATCGC ATATGGCTTT CTTGATAATT TAGGATATGA TAACGCATCA    8100
ATGCTTCCCA CCGGDATAGT ATAGACACGT GGACGATAAC CTTGATATTG CTCAAATTGT    8160
CGACAAACCA TATGATTTTG AATATCTGTT GCTGTAATAA AGAAATCAAT GTATTTAGCT    8220
TTTGAAAATT GATATTCATA ATAATTGTTC CATAGTATAT GCTGCTCGCT CATCATATTA    8280
TTACTATAAT GATCAGCATG AATCACAACA CCAACTTTAC TATCACCTTT ATGCTGCAAA    8340
ACAGCCTGAC CAATATCAGA AGCGCGGTCT AATATGACAA TATCGTCTCG GGTTAAATTC    8400
AATCGTTGTA AAAAGTATGC AATAAATTCC GTTTGTTAT ACAACACCGC ATCTTCAAAC     8460
ACATATATAG AGCTGTCTCC ATCAATATAT TCGTTATAAG CGATGGAACC ATCTTCATTA    8520
TAGAATTGTC GCATATATAA TTTCGCTTTA TTATCAGCTG GTGCATAATA CTCAGAAAAT    8580
ATACGCGTAT AACTATAAAA ATCTTTACGT ACTAACATAC TATTAATTAC AATTCTGCAC    8640
GATCCACAAC ATCTTTTTGT TCATTTGTA GATAACATGT TACAAATGAT GATTTCCCAT     8700
TAAAATATAG ACGGACTATC TTACCATTTC TTTCTCTAAA ACTAATTTCA TGACCAAGCT    8760
CACGTTCAAT GTCATCTAAC GTGTACGTTG TTGGTGCTAT AGAAATATCA CTAAAAATAC    8820
TGATACAACC AAATAACTTC TTGATCTTTA AACCCAATGT TTGCGTTAA TGTCTGTATG     8880
```

-continued

```
TTCTCTGACT GTATAAAATC TAAAAACACA AATTTAGTGT CTTGATTTGT ACGTCTCAAT    8940

AATTTAGCAC GGTAAGCTT                                                 8959
```

( 2 ) INFORMATION FOR SEQ ID NO:2:

( i ) SEQUENCE CHARACTERISTICS:
        ( A ) LENGTH: 10207 base pairs
        ( B ) TYPE: nucleic acid
        ( C ) STRANDEDNESS: double
        ( D ) TOPOLOGY: linear ( i i ) MOLECULE TYPE:Genomic DNA ( v i ) ORIGINAL SOURCE:
        ( A ) ORGANISM: Staphylococcus aureus
        ( B ) STRAIN: Clinical Isolate SA- 24

( x i ) SEQUENCE DESCRIPTION: SEQ ID NO:2:

```
AAGCTTATGG ACCTATTTTA GGTATATTGA TTAGTTGGCT TGGATTAATT TCTGGAACAT      60

TTACAGTCTA TTTGATCTGT AAACGATTGG TGAACACTGA GAGGATGCAG CGAATTAAAC     120

AACGTACTGC TGTTCAACGC TTGATTAGTT TTATTGATCG CCAAGGATTA ATCCCATTGT     180

TTATTTTACT TTGTTTTCCT TTTACGCCAA ATACATTAAT AAATTTTGTA GCGAGTCTAT     240

CTCATATTAG ACCTAAATAT TATTTCATTG TTTTGGCATC ATCAAAGTTA GTTCAACAA      300

TTATTTTAGG TTATTTAGGT AAGGAAATTA CTACAATTTT AACGCATCCT TAAGAGGGA      360

TATTAATGTT AGTTGTGTTG GTTGTATTTT GGATTGTTGG AAAAAAGTTA GAACAGCATT     420

TTATGGGATC GAAAAAGGAG TGACATCGTG AAAAAAGTTG TAAAATATTT GATTTCATTG     480

ATACTTGCTA TTATCATTGT ACTGTTCGTA CAAACTTTTG TAATAGTTGG TCATGTCATT     540

CCGAATAATG ATATGTCACC AACCCTTAAC AAAGGGACGT GTTATTGTAA ATAAAATTAA     600

AGTTACATTT AATCAATTGA ATAATGGTGA TATCATTACA TATAGGCGTG GTAACGAGAT     660

ATATACTAGT CGAATTATTG CCAAACCTGG TCAATCAATG GCGTTTCGTC AGGGACAATT     720

ATACCGTGAT GACCGACCGG TTGACGCATC TTATGCCAAG AACAGAAAAA TTAAAGATTT     780

TAGTTTGCGC AATTTTAAAG AATTAGATGG AGATATTATA CCGCCTAACA ATTTTGTTGT     840

GCTAAATGAT CATGATAACA ATCAGCATGA TTCTAGACAA TTTGGTTTAA TTGATAAAAA     900

GGATATTATT GGTAATATAA GTTGAGATA TTATCCTTTT TCAAAATGGA CGATTCAGTT     960

CAAATCTTAA AAAGAGGTGT CAAAATTGAA AAAAGAATTA TTGGAATGGA TTATTTCAAT    1020

TGCAGTCGCT TTTGTCATTT TATTTATAGT AGGTAAATTT ATTGTTACAC CATATACAAT    1080

TAAAGGTGAA TCAATGGATC CAACTTTGAA AGATGGCGAG CGAGTAGCTG TAAACATTAT    1140

TGGATATAAA ACAGGTGGTT TGGAAAAAGG TAATGTAGTT GTCTTCCATG CAAACAAAAA    1200

TGATGACTAT GTTAAACGTG TCATCGGTGT TCCTGGTGAT AAAGTAGAAT ATAAAAATGA    1260

TACATTATAT GTCAATGGTA AAAACAAGA TGAACCATAT TTAAACTATA ATTTAAAACA    1320

TAAACAAGGT GATTACATTA CTGGGACTTT CCAAGTTAAA GATTACCGA ATGCGAATCC    1380

TAAATCAAAT GTCATTCCAA AAGGTAAATA TTTAGTTCTT GGAGATAATC GTGAAGTAAG    1440

TAAAGATAGC CGTGCGTTTG GCCTCATTGA TGAAGACCAA ATTGTTGGTA AAGTTTCATT    1500

TAGATTCTGG CCATTTAGTG AATTTAAACA TAATTTCAAT CCTGAAAATA CTAAAAATTA    1560

ATATGAAACA AATACAACAT CGTTGTCGG TTTTAATACT GATAAACGAT GTTTTATTTT    1620

GTTAGTACCA CAATAAAAGC TAAGTTCGAA ATGAACTTAT AATAAATCAA TCACAATCAC    1680

TTTGTGTTAA AATATGTGTC AAAGGAAGTG AGGGTTTGTC ATGACATTAC ATGCTTATTT    1740

AGGTAGAGCG GGAACAGGTA AGTCTACGAA AATGTTGACC GAAATAAAAC AAAAAATGAA    1800
```

```
AGCAGATCCG CTTGGAGATC CAATCATTTT AATTGCGCCA ACTCAAAGTA CATTTCAATT   1860
AGAACAAGCC TTTGTCAATG ATCCGGAATT AAATGGTAGT TTAAGAACAG AAGTGTTGCA   1920
TTTTGAACGA TTAAGTCATC GTATTTTCCA AGAAGTTGGT AGTTATAGCG AACAAAAGTT   1980
ATCTAAAGCT GCAACGGAAA TGATGATTTA TAACATTGTT CAAGAACAAC AAAAGTATTT   2040
AAAACTTTAT CAATCACAAG CAAAATATTA TGGGTTTAGT GAAAAATTAA CAGAACAAAT   2100
TCAAGATTTT AAAAAATATG CAGTAACGCC TGAACATTTA GAACACTTTA TTGCTGATAA   2160
AAATATGCAA ACTCGAACTA AAAATAAGTT AGAGGATATT GCTTTAATAT ACCGTGAGTT   2220
CGAACAACGC ATTCAAAACG AGTTTATTAC TGGTGAGGAT TCATTACAAT ATTTTATTGA   2280
TTGTATGCCG AAATCAGAGT GGCTAAAACG TGCTGATATA TATATTGATG GTTTTCACAA   2340
CTTTTCAACG ATTGAGTATT TAATAATCAA AGGATTAATT AAATATGCGA GAGTGTCACA   2400
ATTATATTGA CGACAGATGG TAACCACGAT CAATTTAGTT TTTAGAAAA CCATCGGAAG   2460
TGTTACGACA TATTGAAGAA ATAGCAAATG AACTCAATAT TTCTATTGAA CGTCAATATT   2520
TCAACCAATT ATATCGCTTC AATAATCAAG ATTAAAGCA TCTTGAACAA GAATTTGATG   2580
TACTTCAAAT CAATCGAGTG GCATGTCAAG GTCATATCAA TATTTTAGAA TCTGCGACTA   2640
TGAGAGAGGA AATAAATGAA ATTGCGCGAC GTATCATCGT TGATATTCGT GATAAGCAAT   2700
TACGATATCA AGATATTGCA ATTTTATATC GTGACGAGTC TTATGCTTAT TTATTTGATT   2760
CCATATTACC GCTTTATAAT ATTCCTTATA ACATTGATAC AAAGCGTTCG ATGACACATC   2820
ATCCGGTCAT GGAAATGATT CGTTCATTGA TTGAAGTTAT TCAATCTAAT TGGCAAGTGA   2880
ATCCAATGCT ACGCTTATTG AAGACTGATG TGTTAACGGC ATCATATCTA AAAAGTGCAT   2940
ACTTAGTTGA TTTACTTGAA AATTTTGTAC TTGAACGTGG TATATACGGT AAACGTTGGT   3000
TAGATGATGA GCTATTTAAT GTCGAACATT TTAGCAAAAT GGGGCGTAAA GCGCATAAAC   3060
TGACCGAAGA TGAACGTAAC ACATTTGAAC AAGTCGTTAA GTTAAAGAAA GATGTCATTG   3120
ATAAAATTTT ACATTTGAA AAGCAAATGT CACAAGCGGA AACTGTAAAA GACTTTGCAA   3180
CTGCTTTTTA TGAAAGTATG GAATATTTCG AACTGCCAAA TCAATTGATG ACAGAGCGAG   3240
ATGAACTTGA TTTAAATGGT AATCATGAAA AGGCGGAGGA AATTGATCAA ATATGGAATG   3300
GCTTAATTCA AATCCTTGAC GACTTAGTTC TAGTATTTGG AGATGAACCA ATGTCGATGG   3360
AACGTTTCTT AGAAGTATTT GATATTGGTT TAGAACAATT AGAATTTGTC ATGATTCCAC   3420
AAACATTAGA TCAAGTTAGT ATTGGTACGA TGGATTTGGC TAAAGTCGAC AATAAGCAAC   3480
ATGTTTACTT AGTTGGAATG AACGACGGCA CCATGCCACA ACCAGTAACT GCATCAAGTT   3540
TAATTACTGA TGAAGAAAAG AAATATTTTG AACAACAAGC AAATGTAGAG TTGAGTCCTA   3600
CATCAGATAT TTTACAGATG GATGAAGCAT TTGTTTGCTA TGTTGCTATG ACTAGAGCTA   3660
AGGGAGATGT TACATTTTCT TACAGTCTAA TGGGATCAAG TGGTGATGAT AAGGAGATCA   3720
GCCCATTTTT AAATCAAATT CAATCATTGT TCAACCAATT GGAAATTACT AACATTCCTC   3780
AATACCATGA AGTTAACCCA TTGTCACTAA TGCAACATGC TAAGCAAACC AAAATTACAT   3840
TATTTGAAGC ATTGCGTGCT TGGTTAGATG ATGAAATTGT GGCTGATAGT TGGTTAGATG   3900
CTTATCAAGT AATTAGAGAT AGCGATCATT TAAATCAAGG TTTAGATTAT TTAATGTCAG   3960
CATTAACGTT TGACAATGAA ACTGTAAAAT TAGGTGAAAC GTTGTCTAAA GATTTATATG   4020
GTAAGGAAAT CAATGCCAGT GTATCTCGTT TTGAAGGTTA TCAACAATGC CCATTTAAAC   4080
ACTATGCTTC ACATGGTCTG AAACTAAATG AACGAACGAA ATATGAACTT CAAAACTTTG   4140
ATTTAGGTGA TATTTTCCAT TCCGTTTTAA AATATATATC TGAACGTATT AATGGCGATT   4200
```

```
TTAAACAATT AGACCTGAAA AAAATAAGAC AATTAACGAA TGAAGCATTG GAAGAAATTT    4260
TACCTAAAGT TCAGTTTAAT TTATTAAATT CTTCAGCTTA CTATCGTTAT TTATCAAGAC    4320
GCATTGGCGC TATTGTAGAA ACAACACTAA GCGCATTAAA ATATCAAGGC ACGTATTCAA    4380
AGTTTATGCC AAAACATTTT GAGACAAGTT TTAGAAGGAA ACCAAGAACC AAATGTACGA    4440
ATTAATTGCA CAAACATTAA CGACAACTCA AGGTATTCCA ATTAATATTA GAGGGCAAAT    4500
TGACCGTATC GATACGTATA CAAAGAATGA TACAAGTTTT GTAATATCA TTGACTATAA    4560
ATCCTCTGAA GGTAGTGCGA CACTTGATTT AACGAAAGTA TATTATGGTA TGCAAATGCA    4620
AATGATGACA TACATGGATA TCGTTTACA AAATAAACAA CGCCTTGGAT TAACAGATAT    4680
TGTGAAACCA GGTGGATTAT TATACTTCCA TGTACATGAA CCTAGAATTA AATTTAAATC    4740
ATGGTCTGAT ATTGATGAAG ATAAACTAGA ACAAGATTTA ATTAAAAGT TTAAGCTGAG    4800
TGGTTTAGTG AATGCAGACC AAACTGTTAT TGATGCATTG GATATTCGTT TAGAACCTAA    4860
ATTCACTTCA GATATTGTAC CAGTTGGTTT GAATAAAGAT GGCTCTTTGA GTAAACGAGG    4920
CAGCCAAGTG GCAGATGAAG CAACAATTTA TAAATTCATT CAGCATAACA AAGAGAATTT    4980
TATAGAAACA GCTTCAAATA TTATGGATGG ACATACTGAA GTGCACCATT AAAGTACAAA    5040
CAAAAATTGC CATGTGCTTT TTGTAGTTAT CAATCGGTAT GTCATGTAGA TGGCATGATT    5100
GATAGTAAGC GATATCGAAC TGTAGATGAA ACAATAAATC CAATTGAAGC AATTCAAAAT    5160
ATTAACATTA ATGATGAATT TGGGGGTGAG TAATAGATGA CAATTCCAGA GAAACCACAA    5220
GGCGTGATTT GGACTGACGC GCAATGGCAA AGTATTTACG CAACTGGACA AGATGTACTT    5280
GTTGCAGCCG CGGCAGGTTC AGGTAAAACA GCTGTACTAG TTGAGCGTAT TATCCAAAAG    5340
ATTTTACGTG ATGGCATTGA TGTCGATCGA CTTTAGTCG TAACGTTTAC AAACTTAAGC    5400
GCACGTGAAA TGAAGCATCG TGTAGACCAA CGTATTCAAG AGGCATCGAT TGCTGATCCT    5460
GCAAATGCAC ACTTGAAAAA CCAACGCATC AAAATTCATC AAGCACAAAT ATCTACACTT    5520
CATAGTTTTT GCTTGAAATT AATTCAACAG CATTATGATG TATTAAATAT TGACCCGAAC    5580
TTTAGAACAA GCAGTGAAGC TGAAAATATT TTATTATTAG AACAAACGAT AGATGAGGTC    5640
ATAGAACAAC ATTACGATAT CCTTGATCCT GCTTTTATTG AATTAACAGA ACAATTGTCT    5700
TCAGATAGAA GTGATGATCA GTTCGAATG ATTATTAAAC AATTGTATTT CTTTAGCGTT    5760
GCAAATCCAA ATCCTACAAA TTGGTTGGAT CAATTGGTGA CACCATACGA AGAAGAAGCA    5820
CAACAAGCGC AACTTATTCA ACTACTAACA GACTTATCTA AAGTATTTAT CACAGCTGCC    5880
TATGATGCTT TAAATAAGGC GTATGATTTG TTTAGTATGA TGGATGGCGT CGATAAACAT    5940
TTAGCTGTTA TAGAAGATGA ACGACGTTTA ATGGGGCGTG TTTTAGAAGG TGGTTTTATT    6000
GATATACCTT ATTTAACTGA TCACGAATTT GGCGCGCGTT TGCCTAATGT AACAGCGAAA    6060
ATTAAAGAAG CAAATGAAAT GATGGTCGAT GCCTTAGAAG ATGCTAAACT TCAGTATAAA    6120
AAATATAAAT CATTAATTGA TAAAGTGAAA AATGATTACT TTCAAGAGA AGCTGATGAT    6180
TTGAAAGCTG ATATGCAACA ATTGGCGCCA CGAGTAAAGT ACCTTGCGCG TATTGTGAAA    6240
GATGTTATGT CAGAATTCAA TCGAAAAAAG CGTAGCAAAA ATATTCTGGA TTTTTCTGAT    6300
TATGAACAAT TTGCATTACA AATTTTAACT AATGAGGATG GTTCGCCTTC AGAAATTGCC    6360
GAATCATACC GTCAACACTT TCAAGAAATA TTGGTCGATG AGTATCAAGA TACGAACCGG    6420
GTTCAAGAGA AAATACTATC TTGCATCAAA ACGGGTGATG AACATAATGG TAATTTATTT    6480
ATGGTTGGAG ATGTTAAGCA ATCCATTTAT AAATTTAGAC AAGCTGATCC AAGTTTATTT    6540
ATTGAAAAGT ATCAACGCTT TACTATAGAT GGAGATGGCA CTGGACGTCG AATTGATTTG    6600
```

```
TCGCAAAACT CCGTTCTCGA AAAGAAGTAC TGTCAACGAC TAACTATATA TCAAACATAT   6660
GATGGATGAA CAAGTCGGTG AAGTAAAATA TGATGAAGCG GCACAGTTGT ATTATGGTGC   6720
ACCATATGAT GAATCGGACC ATCCAGTAAA CTTAAAAGTG CTTGTTGAAG CGGATCAAGA   6780
ACATAGTGAT TTAACTGGTA GTGAACAAGA AGCGCATTTT ATAGTAGAAC AAGTTAAAGA   6840
TATCTTAGAA CATCAAAAAG TTTATGATAT GAAAACAGGA AGCTATAGAA GTGCGACATA   6900
CAAAGATATC GTTATTCTAG AACGCAGCTT TGGACAAGCT CGCAATTTAC AACAAGCCTT   6960
TAAAAATGAA GATATTCCAT TCCATGTGAA TAGTCGTGAA GGTTACTTTG AACAAACAGA   7020
AGTCCGCTTA GTATTATCAT TTTTAAGAGC GATAGATAAT CCATTACAAG ATATTTATTT   7080
AGTTGGGTTA ATGCGCTCCG TTATATATCA GTTCAAAGAA GACGAATTAG CTCAAATTAG   7140
AATATTGAGT CAAATGATGA CTACTTCTAT CAATCGATTG TAAATTACAT TAATGACGAA   7200
GCAGCAGATG CTATTTTAGT TGATAAATTA AAAATGTTTT TATCAGATAT TCAAAGTTAC   7260
CAACAATATA GTAAAGATCA TCCGGTGTAT CAGTTAATTG ATAAATTTTA TAATGATCAT   7320
TATGTTATTC AATACTTTAG TGGACTTATT GGTGGACGTG GACGACGTGC AAACCTTTAT   7380
GGTTTATTTA ATAAAGCTAT CGAGTTTGAG AATTCAAGTT TTAGAGGTTT ATATCAATTT   7440
ATTCGTTTTA TCGATGAATT GATTGAAAGA GGCAAAGATT TTGGTGAGGA AAATGTAGTT   7500
GGTCCAAACG ATAATGTTGT TAGAATGATG ACAATTCATA GTAGTAAAGG TCTAGAGTTT   7560
CCATTTGTCA TTTATTCTGG ATTGTCAAAA GATTTTAATA AACGTGATTT GAAACAACCA   7620
GTTATTTTAA ATCAGCAATT TGGTCTCGGA ATGGATTATT TTGATGTGGA TAAAGAAATG   7680
GCATTTCCAT CTTTAGCTTC GGTTGCATAT AAAGCTGTTG CCGAAAAGA ACTTGTGTCA   7740
GAAGAAATGC GATTAGTCTA TGTAGCATTA ACAAGAGCGA AGAACAACT TTATTTAATT   7800
GGTAGAGTGA AAAATTGATA AATCGTTACT AGAACTAGAG CAATTGTCTA TTTCTGGTGA   7860
GCACATTGCT GTCAATGAAC GATTAACTTC ACCAAATCCG TTCCATCTTA TTTATAGTAT   7920
TTTATCTAAA CATCAATCTG CGTCAATTCC AGATGATTTA AAATTTGAAA AGATATAGC   7980
ACAAGTTGAA GATAGTAGTC GTCCGAATGT AAATATTTCA ATTATATACT TGAAGATGT   8040
GTCTACAGAA ACCATTTTAG ATAATAATGA ATATCGTTCG GTTAATCAAT TAGAAACTAT   8100
GCAAAATGGT AATGAGGATG TTAAAGCACA AATTAAACAC CAACTTGATT ATCAATATCC   8160
ATATGTAAAT GATACTAAAA AGCCATCCAA AACAATCTGT TTCTGAATTG AAAAGGCAAT   8220
ATGAAAGAAG AAAGTGGCAC AAGTTACGAA CGAGTAAGAC AATATCGTAT CGGTTTTCAA   8280
CGTATGAACG ACCTAAATTT CTAAGTGAAC AAGGTAAACG AAAAGCGAA TTGAAATTGG   8340
TACGTTAATG CATACAGTGA TGCAACATTT ACCATTCAAA AAGAACGCA TATCTGAAGT   8400
TGAGTTACAT CAGTATATCG ATGGATTAAT CGATAAACAT ATTATCGAAG CAGATGCGAA   8460
AAAAGATATC CGTATGGATG AAATAATGAC ATTATCAATA GTGAGTATAT TCGATTATTG   8520
CTGAAGCAGA GCAAGTTTAT CGTGAATTAC CGTTTGTAGT TAACCAAGCA TTAGTTGACC   8580
AATTGCCACA AGGAGACGAA GACGTCTCAA TTATTCAAGG TATGATTGAC TTAATCTTTG   8640
TTAAAGATGG TGTGCATTAT TTTGTAGACT ATAAAACCGA TGCATTTAAT CGTCGCCGTG   8700
GGATGACAGA TGAAGAAATT GGTACACAAT TAAAAAATAA ATATAAGATA CAGATGAAAT   8760
ATTATCAAAA TACGCTTCAA ACGATACTTA ATAAAGAAGT TAAAGGTTAT TTATACTTCT   8820
TCAAATTTGG TACATTGCAA CTGTAGTATT TTGATTTTCA AAAGAATAAA AATAATTTC   8880
GATTAAGTGC AAAGTCCTTG TAGCAGAATG AACACAACTC ATTTCAAAA TTGTCTTACT   8940
TATTTATTTG TTATTTGATA ACGAAAAAAG TTATAATGTG AATTAAGATA AAGATGAGGA   9000
```

-continued

```
GTTGAGAATG AATGAAATTC TTATCATTCA AGTATAATGA CAAAACTTCA TATGGCGTTA    9060
AAGTAAAACG CGAAGATGCT GTATGGGATT TAACACAAGT ATTTGCTGAC TTTGCAGAAG    9120
GAGATTTCCA TCCTAAAACA TTGTTAGCTG GTTTACAACA AAATCATACT TTAGATTTTC    9180
AAGAACAAGT ACGTAAAGCA GTTGTAGCAG CAGAAGATAG CGGCAAAGCT GAAGACTATA    9240
AAATTTCATT TAATGACATT GAATTCTTAC CACCAGTAAC ACCTCCGAAT AATGTGATTG    9300
CTTTTGGTAG AAATTACAAA GATCATGCGA ACGAATTAAA TCATGAAGTA GAAAAATTAT    9360
ATGTATTTAC AAAAGCAGCG TCATCTTTAA CAGGAGATAA TGCAACAATT CCAAATCATA    9420
AAGATATTAC TGATCAATTA GATTATGAAG GTGAATTAGG TATTGTTATT GGTAAGTCTG    9480
GTGAAAAGAT TCCAAAAGCA TTAGCTTTAG ATTATGTTTA CGGCTATACA ATTATTAACG    9540
ATATCACTGA TCGCAAAGCA CAAGTGAAC AAGATCAAGC ATTTTATCA AAAAGTTTAA     9600
CTGGCGGTTG CCCAATGGGT CCTTATATCG TTACTAAAGA CGAACTACCA TTACCTGAAA    9660
ATGTAAATAT TGTTACAAAA GTTAACAATG AAATTAGACA AGATGGTAAC ACTGGCGAAA    9720
TGATTCTTAA AATTGATGAA TTAATAGAAG AAATTTCAAA ATATGTTGCA CTACTACCGG    9780
GAGATTATTA TTGCAACTGG TACACCAGCT GGCGTTGGTG CAGGTATGCA ACCACCTAAA    9840
TTTTTACAAC CAGGTGATGA AGTTAAAGTG ACTATTGATA ATATTGGAAC GCTGACAACT    9900
TATATCGCTA AATAATTATC ATTTAAAAAG CTAACCAGGT CTTTATATAG ATTGGTTAGT    9960
TTTTTCTTGC TTTTCTAAAA AGGTGTTAAA GATAAATTAT TTATAATGTT ACCATTTGA    10020
GATGAAAGTG AAATATTGAT ATTAAGAAGT AGTTGATTAT TTACAGCAG ATTCACAATA    10080
TTCTAATAAG GGCAATGCAA ATGTCATGTT CTTCCTCTCA AATATAGAAG TGTGGTAGAA   10140
TATATATTCG TGTATAATCA AATCTAGATT AAATTACAAG CAAGTGGGTA TTAATCCCAA   10200
GAAGCTT                                                             10207
```

( 2 ) INFORMATION FOR SEQ ID NO:3:

( i ) SEQUENCE CHARACTERISTICS:
        ( A ) LENGTH: 2082 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus aureus
        ( B ) STRAIN: Clinical Isolate SA-36

( x i ) SEQUENCE DESCRIPTION: SEQ ID NO:3:

```
AAGCTTTCTA ATCTATCGTT AATGATTTGC TTTAAAATTG GGTCGAAGTT AATTGAAGGT     60
GTGAAGTGTA TATCTGTATT AATAACCATG TCATTCATTT GCTGCTTCAC TTTGTTAACA    120
AGTCTTCCGT CATATAAAAA TAATGGTACG ACAATCAATT TTTGATACCG TTCGAGATG     180
CTTTCTAAAT CATGTGTAAA ACTAATCTCT CCATATAGCG TTCTCGCATA AGTAGGTTTA    240
TTAATCTGCA AATGTTGAGC GCATATTTGT AACTCTTCGT GTGCCTTAGT AAAATTTCCA    300
TTAATATTGC CGTGTGCAAC AACCATAACT CCAACTTGTT GTTCGTCACC TGCTAATGCG    360
TCACAAATAC GTTGTTCAAT TAATCGTCTC ATTAAAGGAT GTGTGCCAAG TGGCTCGCTT    420
ACTTCTACCT TTATGTCTGG ATACCGTCGT TTCATTTCAT GAACGATATT CGGTATATCC    480
TTGAGATAAT GCATTGCACT AAAGATTAGC AATGGTACAA TTTTAAAATG GTCAACCCCA    540
CTTTGAATCA ACGTCGTCAT TACCGTCTCT AAATCCTGAT GCTCACTTTC TAAAAACGCA    600
```

-continued

| | | | | | |
|---|---|---|---|---|---|
| ATATCATAGT | GATGTATATC | ATCTTTTACT | AATTCAGAAA | TAAATGCTTC | TAACGCTTGA | 660
| TTCTGTCGTC | CGTGCCTCAT | GCCATGTGCA | ACAATGATAT | TCCCATTCAC | ATTACCAAC | 720
| CCTTTCACAC | GTATTGTATA | CCAAATCATT | TTGTTTTTGT | GAAAAGAATC | ACATTATAAT | 780
| GTAAAATCAG | GGAATTCCCT | GATGCCTGTA | GTCATGCATA | TTCCTTATAC | ATTTTCCCTT | 840
| TTTGTTAAAT | CAAAAAAGC | GACCGATATA | TGAATCCCTA | CTCAACATTT | ATTGAGCAA | 900
| GCATCAATAT | ATCGGTCGCT | TGTAGTGTAT | ATTATTATCT | TAAAATGGTG | GTTGGCCTAA | 960
| TATTGTTTCG | TCAAAGCGCT | CGGGTATCAA | TACTTTGCGC | ATGATCACAC | CTAAATCGCC | 1020
| ATCATCATTT | TCATGTTCGC | TGTATATTTC | ATAACCTCTT | TTTCATAAA | TTTTAAGTAA | 1080
| CCACGGATGC | AATCTTGCAG | ATGTACCTAA | AGTAACTGCC | GCTGACTTTA | ACGTATCTCG | 1140
| CAAAATGCT | CTTCAACATA | AGTAAGTAAT | TGGCTACCAT | AGCCTTTCCC | TTCATACTCA | 1200
| GGATTTGTCG | CAAACCACCA | GACAAAAGGA | TAGCCCGAAA | TACTTTCAC | ACTTCCCCAA | 1260
| GGATATCTAA | CCGTAATCGT | AGATATAATT | TCATCATCAA | TTGTCATGAC | AAATGTAGTA | 1320
| TTTTTATCTA | TATTTTCTTT | AACAGCATCT | AAATTAGCAT | TAACTGAAGG | CCAATCAATA | 1380
| CCTAGTTCTC | TTAGAGGCGT | AAATGCTTCA | TGCATGAGTT | GTTGCAATTT | TTCTGCATCT | 1440
| TGTTCACTTG | CGAGTCGAAT | CATCGTTTTT | GTCATATTAA | TCCCCACTCT | TTTTTAAATG | 1500
| ATTAACCAT | ATTTATTTT | TAAATAAAT | ATCCATCAAA | GTGTATCAAT | AAATTTATCA | 1560
| CATGTCAGAA | AGTATGCTTC | ATCTGAATAC | ACCAATACTC | TCATGAAACT | TATTAAAAAT | 1620
| TACTCTCTCA | ACGTAAAAAA | ACCATTCAAA | TTCATGAATG | GTTGGAAGA | ATGATTCATT | 1680
| GTTACGCTAT | TTAATCACTA | CATCTTAATT | ATTGTTGCTC | TAAACGATTA | CGCTTACCAT | 1740
| TTAAGAAAGC | ATAAACGAGA | CCTACAAAAA | TACCGCCACC | GACAAAGTTA | CCTAAGAAAG | 1800
| CAAAAACGAT | ATTTTTAAA | ACATGTAACC | ATGAAACTGC | ATCAAGGTTA | AAGAATACCA | 1860
| TACCTGCATA | TAGACCTGCA | TTGAACACAA | CGTGCTCATA | TCCCATGTAT | ACAAAGACCA | 1920
| CGACACCACA | AGCTATGAAG | AATGCCTTTG | TTAAGCCGCC | TTTGAATTGC | ATAGAGATGA | 1980
| AAATACCAAT | ATTAATAAAG | AAGTTACAGA | AAATACCTTT | TGTAAAAATA | TTCAACCATG | 2040
| TTGAATCAAC | AGTCTTTTTC | TGAACTAAAG | CTGTTAAAGC | TT | | 2082

( 2 ) INFORMATION FOR SEQ ID NO:4:

( i ) SEQUENCE CHARACTERISTICS:
        ( A ) LENGTH: 2885 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus aureus
        ( B ) STRAIN: Clinical Isolate SA- 77

( x i ) SEQUENCE DESCRIPTION: SEQ ID NO:4:

| | | | | | |
|---|---|---|---|---|---|
| AAGCTTTTGA | TTAATTTGGG | CTTTAAAGTA | TTCCCAATTA | TAATTCTTCA | TGATTTTCTT | 60
| ATTGGATTTC | GAATTTGGTT | TCATGCATTG | TTGCCTCAAA | GAACATGCTG | AACAGTCATC | 120
| GCATTCATAT | AGCTTGAAGT | CACGTTTAAA | ACCATATCTA | TCATTACGGT | ATGCATATCT | 180
| TTTAAAACCT | ATTCTTTTGT | TATTAGGACA | TATAAATTCA | TCATTAAGTT | CGTCATATTT | 240
| CCAATTTTGA | GTGTTAAAAA | TGTCACTTTT | AAACTTTCTA | GTTTATCTT | TAATAAACAT | 300
| GCCATACGTA | ATAAGTGGCG | TTTTATTAAA | ACATCTATAA | TAGCCATATA | GTTTGCTCA | 360
| CTATCATAAC | TGCATCAGCT | ACATTAACTC | TGGTAATACC | GAGGATTTGA | ATCATTGTTA | 420

| | | | | | |
|---|---|---|---|---|---|
| AAAATGGAAT | TAAAGTTCTA | GTATCTGTTG | GGGTTTGAAA | TAGGTCATAG | GATAAAAAA  480 |
| TTGAGAATTT | GTCGCTATTT | GTAAATTGTA | TCCTGGCTTA | AGTTGGCCAT | TTTTCATATG  540 |
| GTCTTCCTTC | ATTCTCATAA | AAGTTGCATC | ATGATCAGCC | CAGAAAGCTA | TTTCTATCTT  600 |
| TAAGAATCCA | TTTTTGTTCT | TCATATTTAT | TTTTCTTTC  | GGAATAATCA | TCAAATTTCT  660 |
| TTTTGAACTT | CTTAATCTCA | GTTCTTTTTT | ACGGGTCTGT | TTTCTAATTT | GAGCACTCTT  720 |
| CGTTCTAAAT | AGAATGATTT | AAATCTTCGA | TTTCTTTTAT | CTAAATGACT | ACCAATTAAA  780 |
| TCTATTTCTT | CTCGTGATTT | TGAATACTTT | TCTTCCACAC | AAATGTATAT | CTATTGGCAT  840 |
| TAGCTTCTAC | TTATGTACCA | TCAATAAAAA | TTGAATTATT | ATCAATAAGA | TTTTGCTTTA  900 |
| AACATTGACT | ATGGAACTGA | ATAAATAAAG | ATTCAATTAA | CGCATCAGTA | TTAGGATTCA  960 |
| CTCTAAAACG | ATTAATAGTT | TTATAAGAAG | GTGTTTGATC | TTGAGCTAAC | CACATCATTC 1020 |
| GAATACTGTC | ATGAAGTAAT | TTCTCTATTC | TACGACCAGA | AAATACAGAT | TGAGTATATG 1080 |
| CATATAAGAT | GATTTTAAC  | ATCATTTTG  | GATGATAGGA | TGTTGCGCCA | CGATGATGTC 1140 |
| TGAATTCATC | GAATTCGCTA | TCAGGTATCG | TTTCAACAAT | TCATTTACA  | TATCGCGAAA 1200 |
| TATCATTTTA | AGGAATTCTA | ACAGAAGTTT | CTATTGGTAG | TGTAAGTTGG | GCAAAGTGTC 1260 |
| TTATTTTTTT | AAAGTATGTA | AAAGTAAAAT | TACATGTTAA | TACGTAGTAT | TAATGGCGAG 1320 |
| ACTCCTGAGG | GAGCAGTGCC | AGTCGAAGAC | CGAGGCTGAG | ACGGCACCCT | AGGAAAGCGA 1380 |
| AGCATTCAAT | ACGAAGTATT | GTATAAATAG | AGAACAGCAG | TAAGATATTT | TCTAATTGAA 1440 |
| AATTATCTTA | CTGCTGTTTT | TTTAGGGATT | TATGTCCAG  | CCTGTTTTAT | TTCGACTAG  1500 |
| TTTGGAGAAT | TTATTGACAT | TCACATTATT | TAAACGGCAA | CAAAGATTGT | TTTATTTTGA 1560 |
| TAGGCATTAT | ATGGTGTTAA | AAAATTTGCA | TGAAAATTAA | AAAATGCTTC | GTTCAGGAAG 1620 |
| GTGTCGTAAT | TTACCTATTT | GCTGAATGAA | GCATTTATT  | TTTAAATATG | ATAGCCAATA 1680 |
| TAACAAGCTA | TAAATCCAAT | GATGAATTGT | AAAAGTGAAT | AATTGAGAAA | AAGGTTAATA 1740 |
| TCAAATTTTG | GTGTCATCAT | TAATGTAAGT | TCCTTGGCTA | ACGTTGAGAA | AGTTGTTAAG 1800 |
| CCACCTAAAA | AAACCGGTGA | CAAAGAACGC | AGGGAACCAT | GAGATTGAAA | TTGATAGGCC 1860 |
| TATAGTTAAT | CCAATTAAAA | AACTACCAAC | TAGATTACT  | ATCAATGTTG | CGATAGGTAA 1920 |
| CTTTGAAGTA | AATTTATGAT | TAAAATAATC | AGTAATGGCA | CTTCTAGCAA | TTGCGCCAAA 1980 |
| ACCGCCGCCA | ATCATGACTA | AATGATTGA  | TATCATGATA | AACCACCACC | TAGTTTTATA 2040 |
| CCGACGTAAC | ATAACAAAAT | ACCAAGACA  | TAACTTGTTA | CAGCATATAG | TAGTAAAGTT 2100 |
| ATAAATTGTT | GATGATCAAA | CATATGTATT | AATTCTAATT | GAAATGTTGA | AAAAGTCGTT 2160 |
| AAAGCACCAA | GAAAACCAGT | CGTAATAGCT | TTTTTTAGGG | TCGGATGGTT | TGAAAAAAAT 2220 |
| GCAATTGTTA | AGGCTGTTAG | CAATCCCATT | ACAAGGCAC  | CAGTCAAATT | GGCTATCAGT 2280 |
| GTTCCGATTG | GAAAACCTCC | GTCAGTATTC | AGAAAAGAAA | TGAGGTAACG | TAATAAAGCG 2340 |
| CCTAAAGCAC | CACCGATAAA | AATATATACA | TATTGCATTT | GGTTCACCTC | GAAAAGAAGT 2400 |
| AGTTTGAATT | TAAAAAAGAG | GTTTTGGCAA | CACGACGACA | AAAATTGTCG | ATGCATTATC 2460 |
| AAACCTCATT | ATATGTTATA | TCTTGTTGTA | TAACTATAGC | GATTAGATGC | ATAGTTATGA 2520 |
| TTTCGAAAAT | CTAATATTTT | TTATACGCAA | CAACGTCATC | AAATTGTTTT | ACTCATTATA 2580 |
| GCATGATACA | TTGTATTGTT | TTGTATTAAC | GCTACATTGA | CATTTATCT  | TTTTAAATA  2640 |
| AAACCGAATG | TACGACAATT | GAAAAGATAT | GTACTAAAAT | AACAATTAGA | ATAATCCAAG 2700 |
| GCAAACTTTT | ACTCGCAATT | CTAATCCAAT | CTGCATCAGG | CTTTAGTGAT | TTAATTGAAC 2760 |
| GATCTGCAAA | AATTATAGAC | AAAATTAGTA | CAATTGAGTT | AATAACACTG | CAGAAAAGTA 2820 |

-continued

```
TTAATTTAAT AAAAGAATTA AAAAATCCAC TTAGGAAAAC GTTATTTGTA TTAAAGAAAA        2880

AGCTT                                                                    2885
```

( 2 ) INFORMATION FOR SEQ ID NO:5:

( i ) SEQUENCE CHARACTERISTICS:
        ( A ) LENGTH: 2362 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 3

( x i ) SEQUENCE DESCRIPTION: SEQ ID NO:5:

```
AAGCTTCACA ACTTGAAAAT ATAGCACAAA CATTAAAGGA TTTAGGTAGA AAACGAGCAA          60

TTTTAATTCA TGGTGCAAAT GGGATGGATG AGGCCACGCT TTCTGGTGAA AATATCATTT         120

ATGAAGTTAG CAGCGAAAGA GCATTAAAAA AATATAGTTT AAAAGCAGAA GAAGTCGGTT         180

TAGCTTATGC AAATAATGAC ACGTTGATAG GTGGTCACC  TCAAACAAAT AAACAAATTG         240

CATTGAATAT CCTAAGTGGC ACGGATCACT CAAGTAAACG AGATGTAGTT TTGTTAAATG         300

CTGGAATTGC TTTATATGTT GCTGAGCAAG TGGAAAGTAT CAAACATGGC GTAGAGAGAG         360

CGAAATATCT CATTGATACA GGTATGGCAA TGAAACAATA TTTAAAAATG GGAGGTTAAG         420

TAATGACTAT TTTAAATGAA ATTATTGAGT ATAAAAAAC  TTTGCTTGAG CGTAAATACT         480

ATGATAAAAA ACTTGAAATT TTACAAGATA ACGGAAATGT TAAGAGGAGA AAGCTGATTG         540

ATTCACTTTA ACTATGATAG AACATTATCA GTTATTGCTG AAATAAAATC GAAAAGCCCA         600

TCTGTACCTC AATTACCGCA ACGTGATCTT GTTCAACAAG TTAAAGATTA TCAAAAATAT         660

GGTGCTAATG CTATTTCAAT ATTAACTGAT GAAAAATACT TTGGCGGTAG TTTTGAACGA         720

TTAAATCAGT TATCAAAGAT AACATCGTTA CCAGTTTTAT GTAAAGATTT TATTATTGAT         780

AAAATTCAAA TAGATGTTGC AAAACGAGCT GGTGCATCTA TTATTTATT  AATAGTAAAT         840

ATTTTAAGTG ATGACCAATT AAAAGAATTG TATTCATATG CAACAAACCA TAATTTAGAA         900

GCTCTAGTAG AAGTTCATAC AATTAGAGAA CTTGAACGTG CACACCAAAT TAACCCTAAA         960

ATTATTGGTG TTAATAATCG TGATTTAAAA CGATTTGAAA CCGATGTTCT ACATACAAAT        1020

AAATTACTTA AGTTTAAAAA GTCTAATTGC TGCTACATTT CAGAGAGTGG CATTCATACA        1080

AAAGAAGATG TTGAGAAAAT AGTAGATTCA AGTATTGACG GTTTACTTGT AGGGGAGGCA        1140

TTAATGAAAA CAAATGACTT AAGTCAGTTT TTTGCCTAGT TTAAAGTTAA AGAAGAATCT        1200

CTATGATAGT TAAATTTTGT GGTTTTAAAA CCGAAAGTGA TATTAAGAAA ATTAAAAAAT        1260

TAGAAGTTGA TGCAGTAGGG TTTATACATT ATCCCGATAG TAAGAGACAT GTCTCACTGA        1320

AACAATTAAA ATATTTGGCT AAAATAGTGC CAGATCATAT AGAGAAAGTA GTGTCGTAGT        1380

AAATCCTCAA ATGTCCACCA TAAAGAGAAT AATTAATCAA ACTGATATTA ACACAATCCA        1440

ATTACATGGA AATGAAAGCA TTCAATTAAT TAGAAATATT AAGAAACTTA ATTCAAAAAT        1500

AAGAATCATA AAAGCAATTC CAGCAACAAG AAATTTAAAT AATAACATTC AAAAGTATAA        1560

AGATGAGATA GACTATGTTT ATTATAGATA CACCATCAAT CACATACGGA GGGACAGGTC        1620

AAAGTTTTGA CTGGAAATTA TTAAAAAAAA TAAAGGCGTT GATTTCTCA  TTGCGGTGGT        1680

TTGGATTTTG AAAAGATAAA ACGATTAGAA ATATATTCAT TTGGACAATG TGGTTATGAC        1740
```

-continued

```
ATCTCAACTG GCATTGAGTC ACATAATGAA AAAGATTTTA ATAAGATGAC TCGAATATTA  1800
AAATTTTTGA AAGGAGACGA ATGATTAATG AAAATTCAAA CAGAAGTAGA TGAATTGGGC  1860
TTTTTCGGTG AATATGGTGG CCAATATGTA CCTGAAACAT TGATGCCAGC TATTATTGAA  1920
CTTAAAAAAG CATATGAGGA CGCGAAATCA GATACTCACT TCAAGAAAGA ATTTAATTAT  1980
TATTTAAGTG AATATGTTGG TAGAGAAACG CCTTTAACAT TTGCTGAATC ATACACAAAA  2040
TTGTTAGGTG GTGCCAAAAT ATATCTTAAA AGAGAAGACT TAAATCACAC TGGTGCTCAT  2100
AAAATTAATA ACGCGATAGG ACAGGCACTA TTAGCTAAAA GGATGGGGAA AACTAAATTA  2160
GTAGCCGAAA CAGGTGCTGG TCAACATGGT GTAGCAAGTG CCACCATCGC TGCTTTATTC  2220
GATATGGATC TTATTGTTTT CATGGGAAGT GAAGATATCA AACGTCAACA ACTTAACGTA  2280
TTTAGAATGG AATTGCTAGG AGCTAAAGTA GTGTCTGTGT CAGATGGGCA AGGAACACTA  2340
TCAGATGCTG TAAATAAAGC TT                                           2362
```

( 2 ) INFORMATION FOR SEQ ID NO:6:

( i ) SEQUENCE CHARACTERISTICS:
        ( A ) LENGTH: 8654 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 22

( x i ) SEQUENCE DESCRIPTION: SEQ ID NO:6:

```
AAGCTTGTTT TATTGCTTAG TTATATTTCC AATAACACTC ATTTTATATG TACGTATTGC    60
CAAAAAAAT TATCTATACA GTAATAAGTA TGAAATGAGA ACTGGAATAA TCATTGGTAT    120
TATTGCTTTA ATTCTAGTAA TTATGCAAGG GTTTCACTTT AACTGGGCTA TTATTCCTAT   180
TTCTATCTAT GGTCATCAGT TTGTATTTTT CGCTGGAATT ATTTTAAGTC TTGTTGGTAT   240
ATTCTTTAAA CGTATAGAAT TGTAGGAGT TGGCTTACTA TTTTGTCAAA AACATAGATG    300
CAATGGTAAC TGACCCGGAA ATTGCACAGT TTTTCTCTTT AGCAATTTGG ATTATACTTG   360
TTGTGCTAAT CATTTTTTAT ACGATACGTT TATCTGAACG CACTAAATCA TCATCATATA   420
CAAAGATTTA AACTCAGAAA ATATGCTAGA CATATCTTTC TGAGTTTTTT AATTTATTAA   480
AATATATCAT TTGTTTACCA TATAAGTTTG TTTTAGAAAA TGAATCACTA TTTTAATATA   540
CAAATAATTT AATTACACTG AAAATAACCT AAAAGCGTAA CACTATTTTA ATATGGGTAT   600
ATAAATGACT AAAGGGAGGT GCCAAGATGA ATAAAATTCA AATTTGTAAT CAGATTGAAC   660
TTAACTATAT TGATGAAGGC GAAGGCATCC CCATCATTTT AATTCATGGA TTAGATGGAA   720
ACTTGGCAGG ATTTAAAGAT TTAAAAAATG AACTCAAGAA GCAGTATAGA GTAATTACTT   780
ATGATGTCAG AGGTCATGGA AAATCTTCAC GAACAGAATC ATATGAATTA AAAGATCATG   840
TTGAAGATTT AAATGATTTA ATGGGAGCAT TAAATATCGA TTCTGCACAT ATTTTAGGAC   900
ATGATATGGG GGGCATCATT GCGAGTGAAT TTACTGAAAA ATATCAATAT AAAGTGATTA   960
CATTGACAAT TGTTTCGGCC AAAAGTGAAG ACATTGCAAA TGGTTTCAAC AAATTAATGG  1020
TTGATTACCA AGAAGAATTA GCAGGCTTTA ATAAATCTGA GGCAATGATT ATTTATTCT   1080
CTAAATTATT TAAAGAGAAA GATAAAGCAA TGAAATGGGT ATCAAAGCCA AAAATTATAC  1140
AATAGACCAA CTCCGGAAGA AAGTGCAATT GCAGTACGTG CATTGCTTAA TATTAAAGAT  1200
TTAACTCGTG TTCATCATAA TGTGTCCATA CCTACTTTAA TTGTGAATGG TAAGTATGAC  1260
```

```
CCACTCATAC  AAAATAAAAG  TCATTATGAT  ATGGATCAAT  ATTATGATCA  AGTTACAAAA  1320
ATTGTATTTG  ATAATTCAGG  ACATGCACCA  CATATCGAGG  AACCAGAAAA  ATTCCTGAAA  1380
CTCTACTTAG  ATTTTGTTAG  TTAAAAAATA  AGAACATAAA  TAAAAACCCT  TAAATGATTA  1440
TTGTCGGAAA  ATCATTGAG   GGTTTTGTAG  TAGCAGTAAA  GTTGGACTC   AGATCACTAT  1500
CGTATTAACT  TAATAAAAGA  GTAAAACAGT  CTTATCTTTC  ATAAGTGAAA  GAAATATCTG  1560
TTTNACTCCC  TAGCCATTAT  ACTTCATTTC  ATTATTTGCT  TCTGTGATAC  GGTTGTTTAC  1620
TCGTTTAAGT  AAATCATCGA  TTTTTTTACG  CTGCTTAGAA  TCTACTAAGA  TTAAAACAGT  1680
TCTTTCATCG  TGTTCATTAC  GTTTTTTATT  AAAGTAATTT  TCTTGAGATA  AATTTTTAAC  1740
AGCTTTAACA  ACTTGAGGTT  GTTTATAATT  TAAGTGATTG  ATAATATCTT  TAAGATAATA  1800
TTCCTCTTCT  TTATTCTCAC  TAATATAAGT  TAATACTGCA  AATTCTTCAA  AGCTGATTGA  1860
GAATTCTTTT  TTAATTATTC  CTTTTAATCT  GTCAGCATAA  GTGACCATAG  CTAATAATTC  1920
AAAGCAGTCA  TTGATTTTTG  AAATAGCCAT  TAATGAAACC  TCCCTATTTA  TATCATATCC  1980
ATAAATCTTA  AAACCCATCT  TTTTAAATTT  AAAGATAGTT  AATTATATTA  TTGAATTAAG  2040
ATTACTTGGA  TACTATACCC  TAATTTATTA  ATTTATATCT  ATTTTTCTTA  TGAAAATACG  2100
AAAGTGTCCG  TCATAATATA  GTATTAATTT  AAATTTAAAG  AATATATTTA  ATGCTATATT  2160
ATTAGTTAA   TTATAACTAA  ATAAAATTAA  GAAGTAAACA  AATAAGTGTT  TATAAAACAA  2220
ATTATCTTTT  AAAGTTTATA  CTTGAATTAG  CAATGTAGCA  TTTGCTATAT  TCAAAAAAAT  2280
AAGATTGTTT  CTAATTTTCC  TTAATTTAAT  AAAAATTATA  CTAAAAAGAA  TACTTTTTGG  2340
AAAGAATTTT  ACTAACATTT  TTTATATATA  AATGTTTATT  AATTTAGAAG  TAGGATTTTT  2400
AACAACTTTT  TCATCTATCA  ATAAGCCTTT  AGTTATATTA  ATATACCCAC  TTTTTAAACT  2460
CTTTTTGTAT  GTTACTTCTC  TTTTTGTAGA  ATTAAAACAT  AGCGTTTTTG  AACAATAGCT  2520
GACGTAGGTA  ACTCTATGTC  ATTTGAGGCT  AATTTGATTT  TAAAGTGTGT  TCCAATTTGA  2580
TGATTGGGTT  GTGTAGAAAG  TAAAATGTCG  TAATATGAGA  CGCCATTTTT  TATTTTTGAT  2640
GGTATATTCG  AAATTTCTTT  AATTTTACTA  GTAAATTGAG  TGTTGTCACT  AGATGTTACA  2700
GAAATATTTT  GATTTATTTT  TAATAAATTC  AACTCAGATT  CTGATATATT  AGCACGAATA  2760
ATACGTTCGT  TGCTATTAAT  TTGCACTATC  TTTCGTTTG   GTTTGAAGG   GATAGAATTA  2820
ATATATGAAA  TACTTCCATT  AATTGGTGAA  AATAAAGTGG  ATTTAATTGA  GGATTTAGTT  2880
TGAATCATTT  GTAATTTTAG  CTGATTAAGG  AATGAATAAT  AATGTAAATC  ATTTTTAGAA  2940
TTTAAAGTTT  TGTTGTTACG  TTCATTACTA  AGTGTATTTT  GGAGTTCCTC  ATATAAATGA  3000
TCTTTTTCAT  AATTGTAATA  TTCTAACACT  GGAGTGTTTT  TAGATACTTT  GCTATGATTT  3060
TTTACTAAAA  GTTTTGGAG   TTGTCCTAAA  GTGGGAGTGT  AGTAGAAAAT  ATAGCTGTTA  3120
AGAGGGGCTT  GTATACCAGT  TGTTGAAAGG  AGTAATTTGG  GCTTGCTTT   TATAGTTTTT  3180
ATATTTTAA   TATCTTCTGT  TTTAGAAGTT  AATTTAGAGA  AAGTAATGTA  ACTAAAACTA  3240
CAAGTTGTGA  GAATGAAAAT  GAATAGTAAT  GAAGAAATAA  CGATGCGTTG  CTTGGTCATG  3300
GATGTTCACC  TCATAATATT  ATTGTGAGGT  TATTATACAC  TATTATTTTA  AATGAAATAT  3360
ATTAATTTTA  AATAAGCATT  ACTTTGGTT   TGTATATTGT  TTTATTTCAA  AAAATAAAGT  3420
AAATCAATTT  AATAAATTGA  AAAATAGAAG  GCTATCTTTA  ATTTAAAAT   ATATGATTCT  3480
ACATAAATGT  TACTATAAGA  AGAATCACTC  ATAAAAACTG  CCAACAAAGA  CAAAATCTTT  3540
GTTGGCAGTT  CGAAATAGAC  ATTTATTTGT  ATGAGGAATC  TACATTAATA  TAAGCGGATA  3600
ATTTTTATTC  AGAATAAGGA  ATTTAAAAATA  ATCGTAATAA  AATAATACCT  ATAGCTATAC  3660
```

```
ATAATAATCC ACCTAACTTA CGTGATGTTA TTTTGTTTTT AGGTGAACCC AACAAACCGA    3720
AATGATCGAT AATAATACCC ATAATCATTT GGCCCATCAT AGCAATTATA GTAGTTAAAG    3780
CTGCTCCTAA GAAAGGCATT AAAATAATAT TAGATGTTAC GAATGCCATT CCTAGTATCC    3840
CTCCAATAAA ATAAATAGAT TTAATCTTAC CTAGTGTTTT ATGAGTAGAT GATATTTTCA    3900
GACTACGATT AAATACTAAT GTTAATATAA ATAACGCTAT TGTACCAACG CTAAATGATA    3960
TGAGTGAAGC AAATATGGAT GAGTGTGTGT GTTGAGCCAG TGTGCTGTTG ATTGTTGTTT    4020
GGATTGGCGG ACGAAACCAA ATACGAATCC AATAAGCAAC CAGAATACTA TTGGTGTATT    4080
CTTATGTCTA TTAACAGGAT GTCTACGAAC ATAATTCATA AATATAATTC CAGTAATTAA    4140
AAATATAATT CCAACACCTT TAAATAATGT AAAAGATTGT TGATGGGCGC CCAATAATCC    4200
AAATGTATCA ATGATTACAC CCATAATAAT TTGCCCTGTA ACCGTAATAA CAACAGTAAG    4260
TGCTGCGCCT AATCTTGGTA ATAATAATAA GTTCCAGTT AAATAGATAA CACCTAATAG    4320
TCCTCCTAGG ACCCAAGTAT AGTTAAGTGT TTGCTTAGAA AAGAATTCTG GTGTTAATAC    4380
TTGTGGATGA ATAATGATAT TAAGCACAAG TAAGCATATT GTTCCGACAG CAAAAGATAT    4440
GGTTGAAGCA TAAAAGATG AACGGGTAAA TTGGCTTAGC CTTGAGTTGA TTGAAGTTTG    4500
AATAGGAAGT AACATGCCAA CAAAAATTCC TAAAAGATAT AGAAAAAACA ATGATAAAAA    4560
CCAACTTTCT CAATTTAATA TGATTATCAT ACCATTCATA ATCATGTTTC TAAAATGATT    4620
GAGCCATAAG CAAAGTATAG AAATAAGTTG TGAATGTTCC GAGGTGTCAT ACAGCCGATA    4680
CTATTTGAT GAATCATTAT AATAAAATGC ACATTAAACA AGTTTAGAA TTAAAAAAG     4740
CGAGACATCA TTTTGAATTT GATATCTCAC TTCATATTAA TAAAAGAACA ATGTAAATTA    4800
AGTTCTTTTT TAGACTTGAA CAATTTAAA AAATTTGTTC TTCGATAAGT CTTTTTATG    4860
ATTTTAGTAC TTTAAATAAA GCGTCAAAAA TAATGTTTTA TGAATTAATT TTTATCTTCA    4920
AATATAACAG TTGTCCTTTT ATCAATAAGT TGTGCAGCAT AAATTTTGAC AGGCTTTCCC    4980
AAACTAAATC TTAAAATGTC TAATTCTAAA ATGTCTAATT CTAAAAGTTG GTTCATACTT    5040
TCTTTAATTA ATTGTTCTGT AGTAATAGCG TTAAAATCGG GTAATAGTAA TTTGACGGGT    5100
TTATTAAGAT TTGATTTAAA TACGAGTTCC AAAGTTTTTG ACATACTGAT GTATCCTCCT    5160
TAAATTAAAG ATTCTGTTTT AACGATCTCG ACTTTGTCAT ACTCTTCGCC ACTGAACGTT    5220
CAATGATGGA ACGAAAAGAT TTGATTTGAT CATTAGAAAC AAGCGGATTA ATGTTAGAAA    5280
AACGACGCTT ATGTTCGACT ACTTTACCTT CAGAATTATG TTTGATTTGA GTAAAGATAA    5340
TCGTCACTTG ATTGACTTCA TTCATAATAA AACCTCCTTT CACTATATAT ATCGAAATAG    5400
ATTGAAAAAA AAGGACACAT TTTTTGAAAA ATATAGGCAA ATGCCTTTGA TGTGATACAA    5460
ACGTCATTTA TCATTAATTA TGAAACCTGT TTTAGAAGGT ATATGAGGTA AGTAGAATTG    5520
TTAAGTTGTA AAAGAAAAAA TTGGAACCTG ATATTTAAAA TAACCAACTT AAAAGATTGA    5580
TCAGTGTCTA AAATTACTAT TTATATATGA ATTAAAATAT TAAGATCTCC CAATATGAGA    5640
ATGAATTAGT TTAAGTTTAT CGATGATTGA AAAATTATAG CCTCATGGAT TCTATCTTAT    5700
ATAAAATAAA GTTCTATTCC CTTTTGGATA TAAATAAGAA TAGTTACCTT TTTGTGATAT    5760
GCCAATTCAG AAAAAAAGCG ACAGTGCTTG AATCTATGTA TGCTCAATAA ACTCATTCAA    5820
ATCAACTAGC AATATCAAAT CATAAATCGT GTTGCACCAT AATAAGGATT AAAACCTGTT    5880
AGTTTAACTA ATTTAAGAAA AACATTTGAT TATCTTCTCT TTCAATCGGG AATATTAATT    5940
TCTATCATTC AACAATATTT TGGATATCAG ATAACTTAAG AAATATTGAG ATTTATTGAA    6000
ATACGATATG TTTCAAATCG CCATACAATG ATTACACTTA ATAAATGATT ACACTTAATA    6060
```

```
TAAATGTAAA AAGAAAAGGA GGGGTTAAAT GAGTTTAGTA TATCTTATGG CGACTAATTT    6120
ATTAGTCATG CTCATAGTTT TATTCACTCT GAGTCATCGT CAACTAAGAA AGGTTGCGGG    6180
CTATGTTGCA TTAATAGCTC CTATTGTGAC ATCTACATAT TTTATTATGA AAATACCAGA    6240
TGTGATTCGA AATAAGTTTA TTGCTGTTCG ATTACCATGG ATGCCTTCAA TTGATATTAA    6300
TTTAGATTTA AGATTAGATG GTTTAAGTTT AATGTTCGGC TTAATTATTT CGCTAATAGG    6360
TGTGGGTGTA TTTTTTATG CTACGCAATA TTTATCCCAC AGTACGGACA ATCTTCCTAG     6420
ATTTTTCATC TATTTACTAT TATTTATGTT CAGTATGATT GGCATTGTAA TAGCTAATAA    6480
TACCATCTTA ATGTATGTAT TTGGGAACT CACAAGTATT TCCTCATTCT TGCTTATATC     6540
CTATTGGTAC AATAATGGTG AAAGTCAATT AGGCGCCATT CAATCTTTCA TGATTACAGT    6600
GTTGGTGGG CTAGCGTTAT TAACAGGATT TATCATTTTA TATATCATTA CAGGAACAAA     6660
CACAATTACT GATATCTTAA TCAACGCAAT GCAATTTCAC GACATCCTTT ATTTATACCA    6720
ATGATTTTGA TGCTATTATT AGGTGCTTTT ACCAAATCTG CACAATTTCC GTTTCATATT    6780
TGGTTACCAA AGGCCATGGC AGCACCTACA CCAGTAAGTG CTTATCTTCA TTCGGCAACA    6840
ATGGTAAAGG CTGGAATCTT TTACTATTT AGATTACAC CTTTATTGGG ACTTAGTAAT      6900
GTTTATATTT ATACAGTGAC ATTTGTTGGT CTAATAACTA TGTTATTTGG ATCTTTAACT    6960
GCTTACGAC AATACGACTT AAAAGGTATA CTCGCTTATT CTACAATAAG TCAATTAGGT     7020
ATGATTATGA CAATGGTAGG TCTAGGTGGC GGTTATGCTC AGCACACATC AGATGAATTG    7080
TCTAAGTTTT ATATTTTAGT TTTATTTGCT GGCTTATTCC ATTAATGAA TCATGCGGTT     7140
TTTAAATGTG CATTATTTAT GGGCGTTGGT ATCATTGATC ACGAGTCCGG AACACGTGAT    7200
ATTCGTTTGC TAAATGGTAT GCGTAAAGTC TCCCCTAAAA TGCATATTGT CATGTTGCTC    7260
GCTGCATTAT CTATGGCAGG TGTTCCTTTT TTAAATGGCT TTTTAAGTAA GGAAATGTTT    7320
TTAGATTCGT TAACTAAAGC AAACGAACTT GATCAATATG GCTTCGTATT AACGTTTGTG    7380
ATTATTTCAA TAGGTGTCAT CGCGAGTATA TTGACTTTTA CTTATGCACT TTACATGATA    7440
AAAGAAACAT TCTGGGGAAA TTACAATATA GAAAAATTTA AACGTAAACA ATACATGAA     7500
CCATGGCTAT TTAGTTTACC AGCTGTGATT TTAATGTTAC TCATTCCAGT TATCTTCTTT    7560
GTTCCAAACG TTTTTGGCAA CTTTGTTATT TTGCCCGCAA CCAGATCTGT ATCTGGGATA    7620
GGGCGGAGGT TGATGCATTT GTGCCACATA TTTCTCAGTG GCATGGTGTG AATCTCCATT    7680
AATTTTAAGA TAGTGTATAT ATTGGACTAT TTAGCTCTA GTGTGATTGG AAAGAGGTTA     7740
CGCATCAAAT AATCAAAAGT GCTCGATTAC AGTGGCTATC GGAAATTTAT AGAGAATTTG    7800
AATTATACTC AGCCCGTGGT ATACGTGCAT TGATGAATAA TAAATTGAAT TATTACATCA    7860
TGATTACATT ATTTATTTT GTAGCTATTG TAGTTATGGA TATTTGACTG TGGGTTTTCC     7920
TCATGTACTC AGCTTCATAT TAGTTCTTTC GGACCGTTGG AAGTTATCTT ATCAGTTGTA    7980
ACATTGATTA TCGGCATTTC ATTAATCTTT ATCGTCAAC GACTAACGAT GGTGGTATTG     8040
AATGGAATGA TTGGATTCGC AGTTACATTA TATTTTATTG CAATGAAAGC TCCAGATTTA    8100
GCTTAACAC AGTTAGTTGT TGAAACTATT ACGACAATCT TATTTATTGT TAGTTTTTCG     8160
AGACTACCTA ACATCCCTCG AGTTAAGGCA AATTTAAAAA AAGAGACCTT CAAAATCATT    8220
GTGTCACTTG TTATGGCATT GACGGTGGTA TCACTTATTT TTGTTGCTCA ACAAGCAGAT    8280
GGTATGCCTT CAATTGCTAA ATTTTATGAA GATGCATATG AACTTACAGG TGGAAAAAAT    8340
ATTGTCAATG CTATACTAGG TGACTTCAGA GCTTTAGATA CTATGTTTGA AGGACTAGTG    8400
TTAATCATAG CTGGATTAGG TATTTATACG TTACTTAATT ACAAAGATAG GAGGGGGCAA    8460
```

-continued

| | | | | |
|---|---|---|---|---|
| GATGAAAGAG | AATGATGTAG | TACTTAAATC | AGTTACAAAA | ATTGTAGTGT | TTATTTTGTT | 8520 |
| AACATTTGGA | TTTTATGTAT | TTTTTGCTGG | CCATAATAAT | CCAGGTGGTG | GCTTTATTGG | 8580 |
| TGGCTTGATT | TTTAGCTCGG | CATTTATCTT | AATGTTTCTT | GCCTTTGATG | TAAATGAAGT | 8640 |
| GTTGAAAAAA | GCTT | | | | | 8654 |

( 2 ) INFORMATION FOR SEQ ID NO:7:

( i ) SEQUENCE CHARACTERISTICS:
      ( A ) LENGTH: 5024 base pairs
      ( B ) TYPE: nucleic acid
      ( C ) STRANDEDNESS: double
      ( D ) TOPOLOGY: linear ( i i ) MOLECULE TYPE: Genomic DNA ( v i ) ORIGINAL SOURCE:
      ( A ) ORGANISM: Staphylococcus epidermidis
      ( B ) STRAIN: Clinical Isolate SE- 32

( x i ) SEQUENCE DESCRIPTION: SEQ ID NO:7:

| | | | | | | |
|---|---|---|---|---|---|---|
| AAGCTTTTTG | ATTTTTAAAG | AAAAAATTAA | ACAAGGGGGC | ATTGCTTATG | GTCAATAGAA | 60 |
| GAAAGATATC | AATTATTGGC | GCGGGACATA | CAGGTGGGAC | TCTAGCATTC | ATTCTTGCAC | 120 |
| AAAAGGAATT | AGGAGATATT | GTGTTGATTG | AACGCCAGCA | ATCAGAGGGT | ATGGCTAAAG | 180 |
| GAAAGGCGTT | AGATATTTTA | GAAAGCGGAC | CCATTTGGGG | GTTGACACA | TCTGTACATG | 240 |
| GTTCAGTAAA | TATAGAAGAT | ATTAAAGATT | CAGACATAGT | GGTGATGACT | GCAGGTATAC | 300 |
| CTAGGAAATC | AGGAATGACA | AGGAGAAGAA | TTAGTTCAAA | CTAATGAACA | AATAGTACGA | 360 |
| GAAACTGCAT | TACAAATTGC | AACGTATGCA | CCTCATTCAA | TAATTATTGT | ATTGACTAAT | 420 |
| CCGGTTGATG | TTATGACATA | TACTGCATTT | AAAGCATCAG | GTTTCCTAA | AGAACGTATT | 480 |
| ATTGGTCAAT | CTGGAATTTT | AGACGCTGCA | AGATATCGAA | CTTTTATTGC | TCAAGAACTT | 540 |
| AACGTGTCTG | TCAAAGATGT | AAATGGGTTT | GTTTTAGGTG | GACATGGTGA | TACGATGTTA | 600 |
| CCTTTGATTA | ATAACACACA | CATTAATGGG | ATTCCAGTTA | AGCATCTTAT | TTCTGAAGAA | 660 |
| AAGATTGATC | AAATTGTTGA | ACGTACACGT | AAGGGTGGTG | CAGAAATTGT | TGCATTACTA | 720 |
| GGTCAAGGCT | CAGCATATTA | TGCACCAGCA | ACTGCTATAT | ATGAAACTAT | AGATGCAATT | 780 |
| TTAATGATC | GGAAACGGTT | ATTACCAAGT | ATTGCTTATC | TAGAGGGAGA | ATACGGTTGT | 840 |
| TCAGATATTT | GTTTCGGAGT | TCCTACTATA | ATAGGATATC | AAGGAATAGA | AAAGATTATA | 900 |
| GAGGTAGATA | TGAATAATGA | TGAGTATCAA | CAACTACAAC | ACTCTGCGCA | AGATGTGAGT | 960 |
| GAAGTCAAAA | ACTCACTAAA | ATTCAAATAA | ATAATTATGA | AGTTCTACAT | CTTAAATTGT | 1020 |
| TAGATTTTTG | TGAAAATTGT | GTAAGGGTA | TTTTTTCGTT | GATTTATAAA | AGCGCTTTCT | 1080 |
| TGATATAATG | AACATATATT | CATAGAATAA | GGAGACGATT | AAAATGGCTA | AGGGGACCA | 1140 |
| ATATCAAGCT | CATACTGAAA | AATATCATGA | GTAAAAAGTC | TAAAAAAAGT | TATAAACCTG | 1200 |
| TGTGGATTAT | CATTAGTTTT | ATTATTTTAA | TTACAATCTT | GTTATTACCC | ACACCAGCAG | 1260 |
| GATTACCTGT | AATGGCTAAA | GCAGCACTAG | CTATTTTAGC | TTTCGCTGTA | GTTATGTGGG | 1320 |
| TTACAGAAGC | AGTTACTTAT | CCAGTTCTG | CAACATTAAT | TTTAGGATTA | ATGATACTTT | 1380 |
| TACTAGGTTT | AAGTCCAGTT | CAAGATTTAT | CCGAAAAACT | TGGAAACCTA | AAAGTGGCGA | 1440 |
| CATAATACTA | AAAGGTAGCG | ATATTTTAGG | AACGAATAAC | GCGCTTAGTC | ACGCTTTTAG | 1500 |
| TGGTTTTTCA | ACCTCAGCCG | TAGCACTTGT | AGCTGCAGCA | TTATTTTTAG | CAGTAGCTAT | 1560 |
| GCAGGAAACC | AATTTACATA | AACGACTTGC | ATTATTTGTG | CTATCAATTG | TTGGAAATAA | 1620 |

| | | | | | |
|---|---|---|---|---|---|
| AACTAGAAAT | ATAGTCATTG | GTGCTATTTT | AGTATCTATT | GTTCTAGCAT | TCTTTGTACC | 1680 |
| ATCAGCTACA | GCACGTGCTG | GTGCAGTTGT | CCCAATATTA | CTGGGAATGA | TTGCTGCATT | 1740 |
| TAATGTGAGT | AAGGATAGTA | GACTTGCTTC | ATTATTAATT | ATTACTGCTG | TACAAGCAGT | 1800 |
| TTCGATATGG | AATATAGGTA | TTAAAAACGG | CTGCAGCACA | AAATATTGTA | GCCATCAATT | 1860 |
| TTATTAACCA | AAATTTAGGA | CATGATGTAT | CATGGGGAGA | GTGGTTTTTA | TATCTGCGCC | 1920 |
| GTGGTCAATC | ATTATGTCTA | TAGCTCTTTA | TTTTATAATG | ATTAAGTTTA | TGCCACCTGA | 1980 |
| ACATGATGCA | ATTGAAGGTG | GAAAAGAGTT | AATTAAAAAG | GAACTTAATA | AATTAGGACC | 2040 |
| AGTCAGTCAT | AGAGAATGGC | GACTAATTGT | GATTTCAGTG | CTTTTATATT | CTCTGGTCGA | 2100 |
| CTGAGAAAGT | ATTGCATCCG | ATTGATTCAG | CTTCGATTAC | ACTAGTTGCT | CTAGGTATTA | 2160 |
| TGCTAATGCC | AAAGATTGGT | GTTATTACTT | GGAAAGGTGT | TGAAAAGAAG | ATTCCTTGGG | 2220 |
| GGACGATTAT | AGTATTTGGT | GTAGGAATCT | CACTTGGTAA | TGTATTACTT | AAAACAGGAG | 2280 |
| CCGCTCATGG | TTAGTGATCA | ACATTTGTTT | GATGGGTCTT | AAACATTTAC | CGATCATAGC | 2340 |
| AACTATTGCG | TTAATTACCT | TATTTAATAT | ATTAATACAT | TTAGGTTTTG | CAAGTGCAAC | 2400 |
| GAGCTTAGCC | TCTGCGTTAA | TACCTGTGTT | TATTTCTTTG | ACTTCAACGC | TAAATTTAGG | 2460 |
| TGATCATGCT | ATTGGTTTTG | TATTAATACA | ACAATTTGTG | ATTAGTTTTG | GTTTCCTACT | 2520 |
| ACCTGTCAGT | GCACCACAAA | ATATGCTTGC | ATATGGTACT | GGGACTTTTA | CCGTAAAGGA | 2580 |
| TTTTTTAAAG | ACAGGTATAC | CTTTAACGAT | AGTAGGTTAT | ATTTAGTTA | TCGTATTTAG | 2640 |
| TTTAACGTAT | TGGAAATGGC | TTGGTTTAGT | GTAAGTAAAA | GATTAGGTA | TTAAAATGAT | 2700 |
| AATTATAAAT | GTCTCGTAAA | GTTAATATT | TTAACTTTAC | GACACATTTT | TTATAAACTC | 2760 |
| GTGGCAAGTT | AATCTTAATA | GTTGAAATGT | ATCGTATAAA | AAATATATGA | ATGTAAATAG | 2820 |
| AATTTAGTAT | TAGAGAATAA | CAAAAAATTG | ATGTTAGGTG | GTAAAATCTA | ATGGCTATAG | 2880 |
| GTGTCATATT | AAATAGAGTT | TTTAGGCTAA | ATAATAATCC | ATTATTTGAT | TATATATATA | 2940 |
| GTAATAAAGA | ATCTATAAAT | CATTGTTATT | TTATTATTCC | AACTGAAGAG | TTTGAAGAAG | 3000 |
| AAGCAAAAAA | GAAAGCACAA | TACTATTATG | GGTCCATACA | GAAGTTTATG | TATGAACTAC | 3060 |
| AACGATATGA | TATAGAACCC | TTTTTGATGT | CTTATGATAA | ATTAATAGAC | TTTTGTAAAA | 3120 |
| AACAAGCTAT | AGACAAAGTT | GTTGTTGCAG | GTGATATTAT | GAGTTATCAT | CACGAAGAAT | 3180 |
| ATGACATTTT | ACATCAAAGG | AAACGATTTA | AACAAGCTAA | TATTCAAGTA | ATATCATTAA | 3240 |
| GAGCAAATCA | TTATTTTAAC | CCCCGCAAAA | CACATAATAA | ACAAGGGGAA | CCATATAAAG | 3300 |
| TATTTACCAG | TTTTTATAGA | AAATGGCGTC | CTTACTTAAT | GATTAGAGAT | GAATATGACT | 3360 |
| ATCATTTAGA | AGATATTTCA | AAGGTTGTAG | TGAAATCTCA | ACATAAAATT | AAAGAAGATT | 3420 |
| ATCATTCATA | TGGTATAAGT | GAACGTGATG | TTCAAAATCG | TTGGTCTGAA | TTTTTATCTC | 3480 |
| AAGATATCGA | AAATTATAAA | GAAAACAGGG | AATACTTGCC | TGAAGTATTA | ACAAGCCAAC | 3540 |
| TAAGTATTTA | CTTAGCTTAT | GGAATGATAG | ATATTATACA | ATGTTTCAA | CGATTACTT | 3600 |
| CAAAATTATG | ATAAAAATGA | ACAAAATTAC | GAAACTTTTA | TACGTGAATT | GATTTTTAGA | 3660 |
| GAGTTTTATT | ATGTATTAAT | GACCAATTAT | CCCGAAACAG | CTCATGTTGC | TTTTAAAGAA | 3720 |
| AAATACCAAC | AATTGAAATG | GTCTTATAAT | GAAGAGAATT | TTAAACTGTG | GAAAGATGGG | 3780 |
| AATACTGGTT | TTCCAATTAT | TGATGCAGCA | ATGGAGGAAC | TTAAAACAAC | TGGATTTATG | 3840 |
| CATAATCGCA | TGAGAATGGT | AGTTTCTCAA | TTTTTAACTA | AAGATTTGTT | TATTGACTGG | 3900 |
| ATTTGGGGTG | AGTCATTTTT | CAAACAAAAA | TTAATAGATT | ATGATGCAGC | TTCAAATGTT | 3960 |
| CACGGATGGC | AGTGGTCAGC | TTCTACTGGA | ACAGATGCTG | TACCATACTT | TAGAATGTTT | 4020 |

-continued

| AATCCTATAA | GACAAAGCGA | GCGTTTTGAT | AATAATGCAC | GATATATAAA | AACTTACATT | 4080 |
| CCAAGATTAA | ATCAGGTAGA | TGCTAAGTAT | TTACACGATA | CTCATAAATT | CGAGCAACAA | 4140 |
| ATAAAGGGGC | AAGGTGTTGA | AATAGGTAAA | GACTATCCTA | AACAAATGAT | TGATCACAAA | 4200 |
| GAAAGTAGAC | AACGTGTAAT | GTCAGAATTC | AAAGCTATAG | ATTAAATAAA | AAAGATCTGA | 4260 |
| ACAACATGAT | ATAGGTGTTC | AGATCTTTAT | CTAGTTACAT | AAAAAAGCAA | ACATGAATTA | 4320 |
| AAATATATTC | TAACAAAGTT | AAAATATACA | TATATTTAAG | ATTTAATTTA | GTTTCAAAG | 4380 |
| GTACTTCCCA | ATTTGTATAA | CGGGGCTCAT | AATAAAATAA | TTGCATCAAA | TATAATCCTA | 4440 |
| TCCCTAACGG | TAAACACATT | AATAAAATAG | CTTTAGTATA | ACTCCATCCT | ATTTGATGCC | 4500 |
| ATAAATGACC | TATCATAAGT | TGAATAATGA | TGAGACATAC | CATTAAAATT | ACTTCAATTA | 4560 |
| TCATTGGTAT | AATCTCACCC | CTTTAATAAA | CAATATGACT | GTTGCTTGTA | TGAGCACCAT | 4620 |
| TAAAACGACA | AATAGTAACG | CTTTAACATC | TATGATTAAA | AAACCTCTT | TCACAATTTT | 4680 |
| TAAAGGTGCA | TTTAATAAAT | AGACAGTATG | TAATCTTAAG | AATCGACCGA | TGTAAATACC | 4740 |
| TAATCCATTT | AAGAACATTA | ATATAACTAT | CAATAGTCGA | TTTAACCATA | CATAAGACGT | 4800 |
| AAAATGTGCA | ATTTCTAAAA | ATATAAGAAT | TGTGAGGTAT | ATTGCTAAGA | GTACGCCAAG | 4860 |
| TATTAAATAG | GTGAAATAAA | TCCATTCTGT | GATGTTTAAT | CCAGCTAAAA | AGTTAAATTG | 4920 |
| AAATTGGTTT | AAGTGTATGA | GATCGGTAAT | CATATAAAAT | GTGTTTGGAA | CTAATAATAG | 4980 |
| AAATATGAGT | CCGAAAACAA | TAAATAAGGG | CCATTCAAAA | GCTT | | 5024 |

( 2 ) INFORMATION FOR SEQ ID NO:8:

( i ) SEQUENCE CHARACTERISTICS:
        ( A ) LENGTH: 3287 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 37

( x i ) SEQUENCE DESCRIPTION: SEQ ID NO:8:

| AAGCTTGCCT | ATTGATTTTA | AAAAATTAAT | GATTATAGGT | TCACTCATAT | CTGTTGCAAC | 60 |
| TGCATCAGTG | CCTATGTTTT | TTGGGAAGCC | ATTTTATAT | CAAACTGAAG | CAAATGTAAC | 120 |
| ATTTCCATTA | CTAGGACATG | TTCATGTTAC | TACTGTGACT | TTATTTGAGC | TTGGCATCTT | 180 |
| ATTAACAGTA | GTAGGTGTGA | TTGTTACAGT | TATGCTATCT | ATAAGTGGGG | GTAGATCATG | 240 |
| AATTTAATAT | TACTCCTTGT | GATAGGATTT | TTAGTGTTTA | TTGGAACTTA | TATGATTTTA | 300 |
| TCTATTAATT | TAATTCGTAT | TGTTATTGGT | ATTTCTATTT | ATACACACGC | CGGTAATTTA | 360 |
| ATTATTATGA | GTATGGGGAA | ATATGGACCT | CATATGTCTG | AACCGCTAAT | TCAAGGTCAT | 420 |
| GCTCAAAACT | TTGTTGATC | CTTTATTACA | AGCTATCGTT | TTAACAGCTA | TTGTGATTGG | 480 |
| ATTTGGTATG | ACTGCGTTTT | TATTGGTGTT | AATATATAGA | ACTTACAGAG | TAACTAAAGA | 540 |
| GGATGAAATA | AGTGCATTGA | AAGGTGATGA | AGATGATGAG | TAATTTAATA | ATATTGCCTA | 600 |
| TGTTGTTGCC | TTTTGTATGT | GCTTTAATTT | TAGTCTTCAC | TAAAAATAAA | AATCGTATTT | 660 |
| CGAAAATCCT | ATCCATTACA | ACTATGATTG | TTAATACAAT | GATTTCAATT | GCTTTACTTA | 720 |
| TTTATGTCGT | TAATCATAAA | CCGATAACAC | TTGATTTTTG | GGGGGATGGA | AAGCACCTTT | 780 |
| CGGCATTCAA | TTTCTAGGTG | ATTCACTGAG | TCTGCTTATG | GTGTCAGTAT | CATCTTTTGT | 840 |
| TGTTACGCTA | ATAATGGCAT | ACGGCTTTGG | TAGAGGGGAG | AAGCGAGTCA | ATCGATTCAC | 900 |

```
CTCCTACATT ATCTTTATTA ACAGTAGGTG TTATTGGTTC GTTTTAACT  TCTGATTTAT   960
TTAACCTATA CGTGATGTTT GAAATTATGC TTCTTGCTTC GTTGTACTT  GTTACATTAG  1020
GACAATCTGT TGAACAATTA CGTGCAGCGA TAGTATATGT TGTTCTGAAT ATTTTAGGTT  1080
CGTGGTTGCT TTTATTAGGA ATTGGCATGT TATATAAGAC AGTCGGAACA CTTAATTTCT  1140
CACATTTAGC GATGCGATTG AATCATATGG AAAATAACCA AACAATAACG ATGATATCTT  1200
TAGTATTTCT AGTTGCTTTT AGTTCAAAGG CAGCACTAGT GATTTTCATG TGGTTACCTA  1260
AAGCATATGC AGTGCTTAAT ACGGAACTTG CCGCGTTATT TGCAGCATTG ATGACAAAAG  1320
TTGGAGCTTA TRCGCTTATT CGTTTTTTA  CTTACTATT  CGACCATCAT CCAAGCGTCA  1380
CGCATACATT GCTCGTGTTT ATGGCTTGTA TCACAATGAT TATCGGTGCA TTTGGTGTCA  1440
TCGCTTACAA AGATATTAAG AAAATTGCGG CTTATCAAGT TATTTGTCT  ATTGGATTCA  1500
TTATTTTAGG TTTAGGTTCT CATACTATAT CAGGTGTAAA TGGTGCTATC TTCTATTTAG  1560
CGAATGATAT TATCGTTAAG ACATTATTGT TTTTTGTAAT TGGTAGTCTT GTTTATATGT  1620
CAGGCTATCG AAATTATCAG TATTTAAGTG GACTGGCAAA AGAGAACCAT TCTTTGGTGT  1680
TGCATTTGTC GTGGTAATTT TTGCTATAGG TGGCGTACCT CCTTTTAGTG GCTTCCGGG   1740
TAAAGTCTTA ATATTCCAAG GGGCTATTAC AAATGGTAAT TATATTGGTT TAGCACTTAT  1800
GATTGTGACA AGTTAATTG  CTATGTATAG TCTTTTTAGA GTGATGTTTA TAATGTATTT  1860
TGGTGATGCT GACGGAGAAC AAGTACAATT TAGACCACTA CCTATTTATC GTAAAGGTTT  1920
ACTTAGTGTT TTAGTTGTAG TGGTATTAGC GATGGGTATT GCAGCCCCTG TTGTTCTGAA  1980
AGTAACAGAG GATGCAACAA ATCTTAATAT GAAAGAAGAT GTCTTCAAA  AGAATGTAAA  2040
TACACATTTG AAGGAGGTTA ATCATAAGTG AAGCAAGTTG TATTAAATAT TGTTATCGCG  2100
TTCCTTTGGG TACCCTTTCA AGATGAAGAT GAATTTAAAT TTACAACCTT CTTTGCTGGA  2160
TTTTTAATTG GTTTAATTGT GATTTATATT CTGCATCGCT TTTTTGGTGA AGAATTTAT   2220
TTGAAAAAGA TATGGGTGGC TATTAAATTT TTAGCTGTAT ACCTATACCA GCTTATTACT  2280
TCTAGTATAA GTACCATAAA TTACATCTTA TTTAAGACGA ATGAAGTTAA TCCAGGTTTA  2340
CTCACATATG AAACTTCATT AAAAAGTAAT TGGGCTATTA CTTTTTAAC  GATTTAATT   2400
ATTATTACTC CAGGATCGAC AGTTATTCGA ATTTCTAAAA ATACTAATAA ATTTTTTATT  2460
CACAGTATTG ATGTGTCAGA AAAAGATAAA GAAAATCTTC TAAAAAGTAT TAAGCAGTAT  2520
GAGGATTTAA TTTTGGAGGT GACACGATGA TTGAAATGTT CACTCAAATA TTTATTATAA  2580
GTGCATTAGT GATTTTTGGT ATGGCACTAC TTGTTTGTCT AGTCAGATTA ATTAAAGGTC  2640
CCACTACTGC TGATAGAGTT GTATCATTTG ATGCCTCGAG TGCTGTTGTT ATGTCTATTG  2700
TTGGTGTGAT GAGCGTTATT TTTAACTCAG TGTCTTAATG TTAATTGCAA TTATTTCGTT  2760
TGTCAGTTCG GTCTCAATTT CAAGATTCAT CGGGGAAGGA CGTGTCTTCA ATGGAAATCA  2820
TAAAAGACAT CGTTAGTCTT ATTGCTTCGA TACTTATTTT CTTAGGAAGT ATTATTGCAT  2880
TAATTAGTGC AATAGGGATT GTAAAATTTC AAGATGTCTT TCTAAGAAGT CACGCCTCAA  2940
CGAAAGTTC  TACATTGTCA GTATTACTAA CTGTAGTTGG TGTACTGATC TATTTTATTG  3000
TGAATTCAGG TTTTTTCAGT GTCAGATTAT TATTATCACT AGTTTTATC  AATCTTACAT  3060
CTCCGGTTGG AATGCATTTG ATAAGTAGAG CGGCCTACCG TAATGGTGCA TATATGTACA  3120
GGAAAGACGA TGCATCTAGA CAATCTACTA TCTTATTAAG CCAAAAAGAG TTTAATACGC  3180
CAGAAGAATT AAAAAAACGT GCAAAACTAC GAGAAGAAAG ACGAGAAAAA TTATACTATA  3240
AAGAAAAAGA ATATATTAAT AAAATGGACG ATTGATTGTT TAAGCTT                3287
```

( 2 ) INFORMATION FOR SEQ ID NO:9:

( i ) SEQUENCE CHARACTERISTICS:
        ( A ) LENGTH: 2291 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus faecalis
        ( B ) STRAIN: Clinical Isolate S2- 1

( x i ) SEQUENCE DESCRIPTION: SEQ ID NO:9:

```
AAGCTTTAGA  TAATGATAAA  CGCGTGTATG  TGAATGTCCA  GCCGATTCAA  TCGCCTACTG     60
GAGAAACAGT  GATTGGTGTC  CTTTATGTGA  AAAGTAATTT  AGAAAATAAA  TACCAAGAAA    120
TTACTAACAC  AGCAAGTATC  TTTTTCACTG  CTTCTATTAT  TGCCGCAGCA  ATCTCGATTA    180
TTGTGACCCT  ACTGATTGCA  CGATCAATCA  CGAAGCCGAT  TGGTGAAATG  CGCGAGCAAG    240
CCATTCGAAT  CGCTCGTGGT  GATTACGCTG  GAAAAGTAGA  AGTCCATGGA  AAAGATGAAT    300
TAGGCCAATT  AGCAGAAACA  TTTAATCAAT  TATCAGAACG  GATTGAAGAA  GCACAAGAAA    360
CAATGGAAGC  AGAAGAATCG  TTTAGATAGT  GTCTTAACGC  ATATGACAGA  TGGTGTCATT    420
GCGACGGATC  GCCGCGGAAA  GGTGATTACG  ATTAATGAGA  TGGCCCTTTC  ATTATTAAAT    480
GTAAAAAATG  AAAATGTGAT  TGGGACCTCG  TTATTAGAGT  TGTTAGATAT  TGAAGAAGAT    540
TACACATTGC  GGAAGCTGTT  AGAAGAGCCA  GATGAACTGC  TGATTGATCG  CTCAACGTCT    600
GATCGTGAAG  AAGACCAAAT  GATTATCCGG  GTAGACTTTA  CGATGATTCG  TCGGGAATCA    660
GGATTTATTA  CTGGCTTAGT  TTGCGTACTT  CATGACGTCA  CAGAACAGGA  AAAAAACGAA    720
CGGGAAAGAC  GGGAATTTGT  TTCCAATGTT  TCTCATGAGT  TGCGACGCCT  TTGACAAGTA    780
TGCGTAGTTA  TATAGAGGCT  TTGAGTGAAG  GAGCTTGGGA  AAACCCTGAG  ATTGCGCCGA    840
ATTTCTTAAA  AGTCACGTTA  GAAGAAACCG  ACCGGATGAT  TCGTATGATT  AATGATTTGT    900
TAAATTTATC  TCGGATGGAC  TCTGGGAATA  CACATCTTCA  ATTAGAGTAT  GTGAATTTTA    960
ACGAATTGAT  TAATTTTGTC  TTGGATCGCT  TTGATATGAT  GATTGAAAAT  GAGCAAAAAA   1020
ATTACAAAAT  TCGCCGTGAA  TTTACTAAAC  GCGATTATG  GGTAGAGTTA  GATACAGACA   1080
AAGTAATTCA  GGTTTTTGAC  AACATTTTGA  ACAATGCGAT  TAAGTATTCG  CCAGATGGCG   1140
GCGTCATTAC  CTGCCGACTA  GTTGAAACAC  ATAATAATGT  CGTCTTTAGT  ATCTCGGACC   1200
AAGGTTTGGG  CATCCCTAAA  AAAGATCTCG  GGAAAGTCTT  CGAGCGTTTT  TATCGTGTGG   1260
ATAAAGCACG  TGCGCGAGCA  CAAGGTGGGA  CTGGTTTAGG  TTTAGCAATT  TCTAAAGAAG   1320
TAATTCGGGC  CCATAACGGG  AGTATTTGGG  TGGAAAGTAC  AGAAGGTGAA  GGATCAACTT   1380
TCTATATTTC  ACTACCATAT  GAACCTTATG  AAGAGGATTG  GTGGGAATGA  TGAAAAAATC   1440
AGAATGGATT  ACAAGAATTG  GCTTGATTTT  GATGGTCATT  TTAAGTATAT  ATTTTTCAGT   1500
CAATATCTGG  CTGAATTCTG  CCAAAAAAAT  ACCAGAAATG  AAGTCGGGAA  GCCAAGTCAC   1560
AACAGCTGTC  AATGAAAAAG  CCATTGGCGA  TGTCTATTTA  CCTTTGCAAT  TGATTCGAAT   1620
AGCCGATGGA  AAAGCGATGC  AAAGTAATCG  TGAAACATTA  ATTAGTAATG  TTCAAAATGA   1680
TATTAAAATG  GCTACGTTTG  GTAAATTGAC  ACAAGTTGTG  ACAAAAAATG  CAGAGCAACT   1740
TAAGCGCTAC  AACCAAATGG  AACAAGGCAT  TGAACTTCTT  TATCAAGGTC  CCTTTTTAAT   1800
CTCGGACTAT  GCTTCGATTT  ATAATCTATC  CATTAATTTT  ACTAACTTTA  ATGAGTTGAC   1860
```

-continued

```
GGACCAGTAT TTTACGAAAA TTCAATTGGA TTTTAACGAA AATAAGATAC GTTTTTTAGA        1920

TTATGATCAA TCCAACGTCT ATGAAGCGCC CATGACTGTT AATAAGGCGC GCTTAATGGG        1980

AATTATCAAT AAAGAGGGAT TGCAATATCA AGACGTTTCC GAAAATACGC TAACCAAACA        2040

AGGACAATGT TATTTAACCA ATGATATGAA GTTGAAAAAG TACAGTTATA TCTTANTTCG        2100

CAACCAGTTA CTCGTTTTAG GAATGCTTTT TTCAATGAAA CGGAAGATAT CCAAACCAAT        2160

GAAGACAGTC AAGACTTAAC CTATACGAGT AAAGAAGAAC GATTGTTTGC AGAAGAAAAA        2220

CTGGGGAAAA TCGATTTTAA AGGGACCTTG CCAGAAGAGA ATAAACGGGA CTCAATCTAT        2280

AATCAAAGCT T                                                             2291
```

( 2 ) INFORMATION FOR SEQ ID NO:10:

( i ) SEQUENCE CHARACTERISTICS:
        ( A ) LENGTH: 3719 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterococcus faecalis
        ( B ) STRAIN: Clinical Isolate S2-3

( x i ) SEQUENCE DESCRIPTION: SEQ ID NO:10:

```
AAGCTTCATT AGAGCGTCAA CTGTTTTTGG TGTTGGGTTC ACAATGTCAA TTAGACGTTT          60

GTGAGTACGC ATTTCGAATT GTTCGCGAGA ATCTTTGTAT TTATGAGTCG CACGAATAAC         120

TGTGTAAAGT GAGCGTTCTG TTGGTAATGG AATCGGACCT GATACGTCAG CTCCAGTTCT         180

TTTTGCTGTT TCCACAATTT TATCCGCTGA TTGATCTAAA ATACGGTGTT CATACGCTTT         240

TAAACGGATA CGAATTTTTT GTTTGCCAT  CTTGTTCCCT CCTTCGCCTA TTTTAAAAGT         300

AGACATAGCT CCACGAAAAT TTATCCGGCA TGCTCGTTCA TGGCAAAGCG TCCGAGCGTG         360

TCGCAACCTC TCGCTTCACA GCCGGCAAAT CAAATCGTTG ATCTACCAAT GCTTTTTACA         420

CTCCTGTAAA CAGCACCTTT TTGATTATAC TATGAAAGGA TAGTGTTAGC AAGGATTTTC         480

TGCGTTTTTT TAAAAGAATT TTTTCTTGTT TTGAAAAGCA TTTGTTTTGT TTTTCAATTC         540

TTTTCATTCT ATTTTTATAA AAAAAGAATT TGAGATTCTT TTTTTACCAG AATCTCAAAT         600

TCTTTCTTTT TTATTCTATT AACCAATCCG GCGCATTGGA ATATCATTGT TATCTGGATG         660

AACCAATAAA TATTGAATAA CATCAATATT GCTTGCTTGG AATGAGGCTG CACATGCTTG         720

CAAATATAAG TCCCACATTC GATAGAAGCG CTCGCCTTTT TCGTCAACAA TTTCTGTTTC         780

TATATTATGG AAGTTTTTTG TCCAATGTTC CAACGTCAAT TGATAATCTC TGCGCAAACT         840

TTCCAAGTCA ATCACTTGCA AGTCGTTTTC TGTCATATGG CCGACTAGCT CAGTGACACC         900

AGGAATATAG CCACCTGGGA AAATATAACG ATTAATCCAA GCATTTTTAG CCCCACCTTG         960

TTGGCGACTG ATCCCATGAA TCAACGCCGT ACCTTTAGGC GCTAAATTTC GCTGAACGAC        1020

ATCAAAATAT TCATGTAGAT TTTCCGCACC GACATGTTCA AACATCCCAA CACTCGTAAT        1080

ATGGTCAAAA GACTCTCCTT TTAAATCACG ATAATCCATC AATTTGACAG TCATTCGATC        1140

TTGTAGACCT TCTTTTTCTA TAATATGGCG AATATGATGA AATTGCTCTT CACTTAATGT        1200

AATCCCAGTT GCTTTGGCTC CATATTCTTT CACCGCAGTT AAAATTAACG TGCCCAGCC         1260

GCAGCCAATA TCCAGTAAAG TGTCGCCCTC TTTGATAAAC AATTTATCTA AAATATGATG        1320

AACTTTATTC ACTTGCGCTT GTTCTAATGT ATCTTCAGGC GTTTAAAAT AAGCACATGA         1380

ATACGTCATT GTTTGGTCAA GCCATTTTTT GTAAAAATCA TTTCCTAGAT CGTAATGGCT        1440
```

-continued

```
GTGAATATCC TCTTGCGAAC GTTTTTTTGA ATGACTTTCT TTAGGAAGCC ATTTAATAAA    1500
TTTAGCATTG TGTAAAAAGC TATCCTTTTG GTTATACACA TCATAAATCA GCGCTTGGAT    1560
ATCGCCTTCG ATTTCAATTT TGCGATCCAT GTAGGCTTCC CCTAAAGTTA ACGAAGCGTT    1620
ATTCAGTAAA TCCTTCACAG GAATTTTTTC ATTGAATACA ATTTTAAAAA CCGGATCCCC    1680
CGACCCTTGC CCATACTCTT TGACGGTACC ATCCCAGTAT GTGACTTGTG TCTTTTTTGA    1740
AAAAGACCAT TTAAACAGTT GACTGTACGT TTCTTTTTCT AACATTGCAT TCCCTCCATT    1800
AAATACCATT TGAAGCCAAA ACAAAAGAA  GTCGCTTTCC GGTAGTTCGT CAAAACAAAC    1860
ACCACAGTCC GTTCTAAACT GAAGCACAGA AAAGTTATCA CCCCTTCTAT GTTCCGCTTC    1920
TTTTTTGCAA TTACAGTTCT ATTCTACTCC TCTTTTAAAA ATTTGAACAT TCTTTTAACG    1980
TAATACCTAC TATTGTTATT CTTTATCACA AAAAAACTAG AGCCAGTCCT TGACAGACTC    2040
CTCTAGTTCT AAATATTATG CTTTCTTACG CATCCGTTGT TCCGCATGAG TGTAAGCGCC    2100
ATGCCACACG TGCCCCACAT AAGGATTAAC TTGAATACCG TGTTTAATCG CCGCTGCTAC    2160
AAATTTTTCG CTAAAGTTAC TGCTTCTAAC ACCGAATAAC CTTTCGCCAA GCCAGCTGTG    2220
ATTGCCGCTG AAAAAGTACA ACCTGCACCA TGATTATAAT CAGTTGGATA TAATTCATTT    2280
TCCAAAAGAT GCGCGGTGTG ACCATCGTAA AATAAGTCCA GTGCTTTTTC ACCAGCTAAG    2340
CGATGTCCCC CTTAACCAC  GACATGCTTG GCTCCATTT  GTACAATTCG TTTGCCGCT    2400
TCTTCCATCT CCGCCACGGA AGAAATTTCG CCTAAACCAG ATAAGATGCC CGCTTCAATT    2460
AAATTAGGCG TGGCAACTAA TGCTAATGGC AGTAAATCGT TTTAGGCCT  TCCACACTTT    2520
TGGGTTGCAG AATTTGTGCC GTTCCCTTAC AAGCAATGAC TGGGTCAATC ACGACTTTTT    2580
GAATTTTTTC TTGTTTAATG TACTTACTAG CCATTTTAAT ATTTTGTTCA TTACCCCATC    2640
ATCCCTGTT  TTCAAAGCCG CTACTGGACC GCCTGCAAAA ACCGAAATCA ATTGTTTTTC    2700
TAAGAGCGTT TCTGGCAATT CAGTTACTTC ATGTGACCAA CCTGTCGTAG GATCCATCGT    2760
CACAATCGAG GTTAAACTTG AAAATCCAAA AACTCCATAC TCTTCAAATG TTTTTAAATC    2820
TGCTTGAATC CCTGCCCCTC CAGTTGAATC GGAGCCTGCA ATCGTCAATA CTTTTTCCAT    2880
TAAATCACCT AACCTTTTTC TCCAAGTATA CGGAAGAAAC AAGTCTGCTA AAACAGCCAA    2940
TTGGCTTATT TTTTAGCCAG CCAATTTCTA AACAAAAAAA AGACCAGAGA ATAAATTCTC    3000
TGGTCTTACG TCCGAATACC CCAGTTTTTC ACGCTGGTTA AAGCTATAGT TAAAAAGTTA    3060
ATTATTTAAC GATTTCAGTA ACAACGCCTG AACCTACAGT ACGTCCGCCT TCACGAATAG    3120
AGAAACGAGT TCCGTCTTCG ATAGCGATTG GGTGAATTAA TTCAACGTCC ATAGCAACGT    3180
TATCACCAGG CATTACCATT TCAGTACCTT CTGGCAATTC TACAACACCA GTAACGTCTG    3240
TTGTACGGAA GTAGAATTGA GGACGATAGT TAGTGAAGAA TGAGTGTGAC GTCCGCCCTC    3300
TTCTTTTGAT AATACGTATA CTTCAGCTTT GAATTTGTG  TGTGGAGTGA TTGTAGCTGG    3360
TTTAGCTAAT ACTTGTCCAC GTTCGATATC TTCACGTGCA ACACCACGTA ATAAAGCACC    3420
GATGTTGTCG CCTGCTTCAG CGTAGTCTAA TAATTTACGG AACATTTCAA CACCTGTAAC    3480
AGTTGTTTTA GATGTTTCGT CTTTAATACC AACGATTTCA ACTTCGTCAC CAACGCGAAC    3540
TTCACCACGT TCAACACGGC CTGTAGCAAC AGTACCACGT CCAGTGATTG AGAATACGTC    3600
TTCGACTGGC ATCATGAATG GTTTGTCAGT ATCACGTTCT GGAGTTGGGA TATATTCGTC    3660
AACTGCAGCC ATTAATTCTA AGATTTTTTC TTCATAAGAC TCGTCGCCTT CTAAAGCTT    3719
```

( 2 ) INFORMATION FOR SEQ ID NO:11:

( i ) SEQUENCE CHARACTERISTICS:
   ( A ) LENGTH: 3480 base pairs
   ( B ) TYPE: nucleic acid
   ( C ) STRANDEDNESS: double
   ( D ) TOPOLOGY: linear ( i i ) MOLECULE TYPE: Genomic DNA ( v i ) ORIGINAL SOURCE:
   ( A ) ORGANISM: Enterococcus faecalis
   ( B ) STRAIN: Clinical Isolate S2-7

( x i ) SEQUENCE DESCRIPTION: SEQ ID NO:11:

```
AAGCTTCTAG CGTTTCGGAT TGGCGCCTAT GATGCACCAG GAGAGCGACG AATCAATACC      60
AAAAATATGC CTACAGCAGG AGGACTTGCA ATCTACATTG CTTTGCTAG  TTCATGTTTA     120
TTGATTTTTC GTTCGATTAT CCCACAAGAT TATATTTGGC CGATTATTTT GGCTGGTGGA    180
ATGGTTGTTT TGACAGGCCT CATTGATGAT ATTAAAGAGA TTACTCCAAT GAAAAAAACA    240
ATCGGTATTT TGTTAGCAGC ATTAGTTATT TTATTTGTT  GCTGGAATTC GGATAGATTT    300
TGTGACGTTG CCAGTTGTTG GAATGATTGA TTTGCGCTGG TTTAGTTTAC CACTAACTTT    360
ATTGTGGATT TTAGCGATTA CGAATGCAGT AAATTTAATT GATGGTTTGG ATGGTTTAGC    420
ATCAGGCGTA TCCATTATTG GATTAACCAC GATTGGTATT ACAGGGTATT TTTTCCTACA    480
TGCTAAAACG GTCTATATCC CAATTGTTAT TTTTATTTTA GTTGCGAGCA TTGCGGGATT    540
TTTCCCATAC AATTTTTATC CGGCTAAAAT ATTTCTAGGA GATACCGGGG CGTTATTCCT    600
CGGGTTTATG ATTGCAGTAA TGTCGTTACA GGGCTTGAAA AATGCTACGT TTATTACGGT    660
AATTACGCCA ATGGTGATTT TAGGTGTGCA ATTACGGATA CGGTTTATGC AATTATTCGA    720
CGGCTATTGA ACAAGAAGCC CATTTCCTCA GCAGATAAAA TGCATTTACA TCACCGCTTG    780
TTATCTTTAG GTTTACCCA  TAAAGGGGCG GTCATGACTA TTTATGCATT AGCGTTAGTT    840
TTTTCCTTTG TCTCTTTATT GTTCAGCTAT TCAAGTACAG TAGCATCAAT TTTATTAATT    900
GTCTTTTGTT TAATTGGCTT AGAACTATTC ATTGAACTAA TCGGTCTAGT TGGCGAAGGG    960
CATCAACCGT TGATGTATTT GTTACGGATT TTAGGGAATC GTGAATATCG TCAGGAGCAA   1020
ATGAAAAAGC GACTTGGCAA GCATTCTAAG AGAAAGTAAA GAAATCTTTA GGTTGCTTTG   1080
CGAGAGCTAA ACCTATGATA TAATTCCATT AAACTTAAAA AAGTATATGT GTGAAACATA   1140
TGCTTTTTTT TTAAGACGAT GTTCAGTAG  TAAGGAGAAA TGAGCATGCA AGAAATGGTA   1200
ACAATCTCGA TTGTCACTTA TAATAGTCGT TACATTTTA  ATGTACTAGA CCAATTAAAA   1260
GCCGAACTAG GTACTGATAG TATCTATGAT ATTCATATCT ATGACAATCA TTCTGAAACA   1320
GCGTATCTTG AAAAATTAAC AACATATGAA CCATTTATTA CTATCCATCG CGCTGAAGAA   1380
AATCAAGGGT TTGGTCATGG TCATAATCAA GTGTTATTCA ATGCTTCGAC AAAGTATGCA   1440
ATTATTTTTA TCCCGATGTG TTGGTTACTA AAGACGTGCT TGATCGTTAT TAGACGTATC   1500
AAATAGATAA GAACATTGCA GTCGGTAGCC CTAAAGTTGT TAAATGAAGA TGGCACGACG   1560
CAATATTTAG TTCGTCAAAA ATTAGATGTC TTCGATTATA TGTTACGTTT TATTCCCTTT   1620
CAATTTGTAA AGAAAATTTT TGATAAACGT TTGAGTATTT ATGAATGTCG CGATTTGTCG   1680
GATACAGAAA CAACGGATAT TAAAATGGGC TCAGGCTGTT TTATGTTGAT TGATCGTGAA   1740
AAATTCGTTG AAATTGGTGG GTTCGATGAA CGTTCTTCA  TGTACTTTGA AGACAACGAT   1800
TTATGTTTAC GCTTTGGCAA AGCAGGCTAT CGGATTCTCT ATACGCCTTT TGAAACGGTT   1860
GTTCACATGT ATGAAAGGG  CGCCCATAAA AGTCGAAAAT TGTTTAAAAT CTTTATGCAA   1920
TCAATGGGGA AATTTTTTAA CAAATGGGGC TGGAGGTTCT TTTAATGAGT CAAAGATTAG   1980
```

-continued

```
CGGTAGTCAT CGTCTTATAT CAAATGAAAA TGGCTGATAC GCCGAATTAT TTGTTATTAA    2040

AAGAAGTGGT AGACCACCCC CAATTGCACT TATTTATTTA TGACAACAGT CCACTTCCTC    2100

AAGAAGATGC ATTATTTTTA CAACCAAATG TTACTTATCG ACATAATCCT GATAATCCAG    2160

GACTAGCGAC CGCTTATAAT GAAGCGATTG CTTTTAGTCA AGCGAATCAA TGTGAATTAT    2220

TGTTGCTCCT TGACCAAGAC ACAGAAGTGC CAGCCTCTTA TTTTGATACG TTGATCATCA    2280

TGCCATTAGA TCCGACTGTG GCAGTCTATG TTCCAATTGT AGAAGCAAAT GGACAACAAA    2340

TTTCGCCAGT ATATAGTGAT CAATACGTTG GGCTTAAAGG AGCAAAGCCA ACAGCAGGGA    2400

TAGCCAACCA ACCGTTGATG GCTATCAATT CTGGTACAGT TATTACGGCA GAAACGCTAC    2460

GCTGGTTGGA AGGATTTTCG GAAGAATTTC CTTTGGACTA TTTAGACCAT TGGTTCTTTT    2520

ATCAATTAAA TCAAGCCAAT AAAAAGATTG AAGTCTTACC AATCCACCTA AAACAAGAAT    2580

TGTCTGTTTT AGATTATCGT ACAATGAGTC CTCAACGTTA TCGCTCTATT ATTGAAGCAG    2640

AAACGTTATT TTATCGTCGA TATGATCAAG AAAAGTTTTC CCATCATCGA CGCCATTTAT    2700

TTTTACGCAG TAGTAAGCAA TTTTTAACTG TCAAAAATCG CCAAATTTGG CGGCAAACAT    2760

TGGCAGAATT TCTCAAGTTA ATGAAAGGAT AATCTATGAT CTCAGTTTGT ATTGCGACAT    2820

ATAATGGAGA AAAATATCTC GCGGAACAAT TAGATAGTAT TCTTTTACAA GTCAGTGAAG    2880

AAGATGAACT AATTATTTCA GATGATGGTT CTACTGATCA TACGTTGGAA ATTTTGAGGA    2940

CGTATGCAGC GAATTATCCC CAAATTCAAT TGTTACAAGG TCCCAGGGCA AGGAGTGATT    3000

GCTAATTTTG CATTTGCCT TACGCATACG AAAGGCGAAG TAATATTTTT AGCAGATCAA    3060

GATGATGTTT GGTTGCCAAA TAAAGTAACG ACGGTGACAG AATATTTTGA AGCGCACCCT    3120

GACATCCAAG TGGTTATTAG TGACTTGAAA ATTGTTGATG CGGATTTACA AGTTACCAAT    3180

CCCTCTTATT TAAGTTTCGA AAAGTCAAAC CAGGGTTTTG GCGAAATGCG ATAAAAAGTG    3240

GCTATATTGG GGCAGGTATG GCCTTTCGTC AAGAAATGAA AAACGTCATT TTACCCATTC    3300

CGCCAGAAGT TCCTATGCAT GATATGTGGA TTGGCTTATT AGCTGCACGG AAGAAGCAAA    3360

CGGGTCTCAT TAAAGAACCA TTAGTGCTTT ACCGAAGACA TGGAGCGAAT GTCAGCCCCA    3420

TTATTACCAA AACAAGTTTC CAACAAAAAT TAAATTGGCG TGTGAATTTA TTAAAAGCTT    3480
```

( 2 ) INFORMATION FOR SEQ ID NO:12:

( i ) SEQUENCE CHARACTERISTICS:
        ( A ) LENGTH: 2441 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterococcus faecalis
        ( B ) STRAIN: Clinical Isolate S2- 27

( x i ) SEQUENCE DESCRIPTION: SEQ ID NO:12:

```
AAGCTTCTGC GCTAGGAACC AGCCCTTTAA TTACATCTCC CCATACTGGA TTTGACAATG      60

CCACTTGATA AGCAAAAATC ACAAAAATAA CAACAATTAA AGCAACAACA ATAGCTTCAA     120

TTTTTCTAAA ACCAATTTTT GTCAATAACA ACAAAAGTAA AACATCAAAT ACCGTAATGA     180

AGACAGCCAG ACCTAAAGGA ATATGAAATA ATAAATATAA GGCAATTGCG CCCCCGATAA     240

CTTCAGCGAT ATCTGTAGCC ATAATTGCTA ACTCTGTTAA AATCCATAAT ACAATACCTA     300

ACGTCTTACT AGTTCTAGCA CGAATCGCTT GTGCTAAATC CATCTGTGAA CAATGCCTAA     360

TTTAGCAGCC ATATATTGGA GCAACATTGC AATCAAACTG GAAATTAAAA TAATCGACAT     420
```

```
CAATAAATAT TGAAAATTTT GTCCCCCAGT AATTGAAGTA GACCAGTTTC CTGGATCCAT      480
ATACCCCACT GCTACCAATG CTCCTGGACC TGAGTAAGCA AATAACGTTT TCCAAAAACT      540
CATATTTTTA GGCACGTCGA TGGTGCCATT AATTTCTTCA AGCGAAGGAC CATTTGCATA      600
TTCAATCAAA TGATGTCTTT GCTTTGGTTC ATGTTCTTCT GAATTTTTCA ATTCAATTCC      660
TTCTTTCGTT TTGCAATAAT TTAAAAGGC CCTTCCCGTT AGAAGGTTAA CCTCTAGTAT       720
ATTTTAGGTA CACCTAAAAT ATACTGCTAA AAATAACAAA ATGCAAGACT GAAAGAAAA       780
TTTTGACAGT GTAAAATAG ATTGTCGTAA ATGTGCGATC TTAAAGTTTG AAGAAATCAG       840
GGTAGCTGGT AGTTGATTAT CTTAAGAAGT AGAAAATAAG GACCTAAGT CATTTCGGCT       900
TAGGTCCCTT ATTTTATTTT TATTCGGTTA TTCTATTAAG AATGGATGCT ACAATTTCTG      960
TCGTGTCAGC TGAATGATTT CTAAAATCTC GTAAACTTAA TCTGACGAAA ACCTTCAAGT     1020
ACTTCGGGCA ACTTATTTTN CCCCCATTCA AAAGTTCCAT CATTTCTTTT CAATAATCTT     1080
TGTAAAATTT CTTCTTTCTC GACCGCTAAC AAAAAATGAT AAACGTCAAT GCCTGCTCGT     1140
CTCAGATATC CAATCAGCTC TTCTTCATAT TCATTTTTAT AAAGGGTCAT TGTAACAATA     1200
ATCGGCCGTC CAGACTCTTT GGACATTCGT TTTAATAAAT GAGCATTCCA GCAACGCCAT     1260
TCCTGATACT CCTGAAAATC ATTTTCTTTC ATTTCTTCGG GAACTAGCTC CATCAATGCA     1320
CTACCAATAA TTTCTGGATC ATAAATGATT GCGTTGGGAA GTTTTGTTG TAACTCATGT      1380
GCAATGGTCG TTTTTCCGGA TCCAAACGCA CCGTTTAACC AAATAATTAT CATAATTTCC     1440
TTTCTTCTG AACAAATTTC TTTGTTGTTT AATTTAGGTG CTAGATTACT TTTAATTTTT      1500
TTAGCCATTC ACTTATAGTT ACTACTTACA TCTTTAACAG TAAACGAGAC AAACTAAAAA     1560
TACAACATCC TACGCTATTA ACCTCGGGTT ATATAACATA CTCATCTGAT AATTTCTCCC     1620
TAAAAAAACA GAATGTGGGC AATCTTTTA AGAATAATTG AATAGAATAA CAACAAACAG      1680
TAATTCAGGT ATAACCAGCT AGAAATTGTT TTATTTTTAG TCACGAGTAT GATAAGCATG     1740
TAAATCAAAT AGAATCATAT TAGGTGAGGT TACTCTGAAG AACACAGGTT ATCGCTCGGA     1800
AATGTCGAGA GACAGTAACG AGTAAAGCAG GGATTGTCGA ATTAAGGCTT CCTAAGATA     1860
ACTAGAATTT TTTTCTTACG TCTCAGAAAG CCAAAGCTCA ATTATTGTGA TTACCCTATA    1920
ATCTTCTTCT TTTATTCGGC GACCTCTTTA ATATGATTAA TTGGAGGTTT TTAAATTGAA    1980
AGCTGTCACT GCATCATCTA AGAAAAATAC CCTACTTGCT AAAAGTATCG GGAATCTTAC    2040
CTTGCTCATC ATTTAGGCA TTTTCATTTT TATCATCGTC TTCTCTTGGC TAAAAATGAA     2100
TCGCCCTCTC CACACCCTTC CCTCAGAAGA ATTCCTCGCA ACACCAAGTA AACAGATGA     2160
TTTCTTATCT CCATCAAATC TTTTTTACTT TCAATTCGA ACCATGTTTC GAATGATTGT     2220
GGGGATGGCT TGGTCCTTCC TGTTTTCCTT TGTTTTGGT ATTTAGCCG TAAAATATAA      2280
AACGGCACGA AGAGTCATTT TACCATTAGT TAATTTCCTT GAATCTGTTC CATTGCTAGG    2340
TTTTTTGACC TTTACAACTG CTTGGTTACT TGGTTTATTT CCAGGAAATG TGATGGGCGC    2400
AGAAGCGGTT GCTATTTTTG CCATCTTCAC AGGTCAAGCT T                        2441
```

( 2 ) INFORMATION FOR SEQ ID NO:13:

( i ) SEQUENCE CHARACTERISTICS:
        ( A ) LENGTH: 9515 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
  ( A ) ORGANISM: Pseudomonas aeruginosa
  ( B ) STRAIN: Clinical Isolate P2- 2

( x i ) SEQUENCE DESCRIPTION: SEQ ID NO:13:

| | | | | | | |
|---|---|---|---|---|---|---|
| AAGCTTTCCT | CCAGACCCTT | CACCGCCGTG | GAGATCGACG | GCTGGGCGAT | GTACAGCTTG | 60 |
| CGCGAGGCCT | CGGCCACGCT | GCCGCATTCC | ACGGTGGTCA | CGAAATACTT | GAGTTGCCGC | 120 |
| AAGGTATAGG | ACGCCACTGC | AAGACCTCAT | CGGCGCATCA | TCCTCCCCGG | GCCGGGCGTG | 180 |
| CGCGCCTCGA | TTGTTGTGTC | CGCCGCGCTG | CAAGCAAGTT | GCAGGCCGCT | GCCGAGCGTC | 240 |
| GCGCGCTGGC | CGCGGAACGA | TTGCCCGCCT | GCACGATAAC | CCAGCACGAC | GCACTTTGCC | 300 |
| GGGGCACGCC | TGGCCAGCTT | TTTCTTATGT | CCCGAGGACA | TTTTTAATAA | TTTTCCTTCG | 360 |
| CCGCGGCTTG | CGCGACCATC | CTTCCCCATC | GACCCCATGG | ACAGCGGTTC | GCCTCCCGGC | 420 |
| GGTCCGGGCC | ATGCGTGCAG | AACCACGACC | GGCGCAGACC | GGCGAGATAA | CAAGGAGAAG | 480 |
| GTGGGGTGTT | CGAACTCAGC | GATTGGCAAC | GGCGCGCCGC | GACACAGCGC | TTCATCGACC | 540 |
| AGGCCCTGAT | CGGCGGCCGC | CAGCGTCCAG | CCGCCAGCGG | CGCTACCTTC | GACGCCATCG | 600 |
| ATCCGGCGAG | CAATCGCCTG | CTGGCGCGGG | TCGCGGCCTG | CGATGCGGCC | GACGTCGACG | 660 |
| CGGCAGTGGC | CGCCGCCCGC | CGCGCCTTCG | ACGAAGGCCC | CTGGGCGCGT | CTCGCCCCGG | 720 |
| TCGAGCGCAA | GCGCGTGCTC | TGCGCCTGGC | CGAGCTGATG | CTGGCCCATC | GCGAAGAGCT | 780 |
| GGCGCTGCTC | GACTCGCTGA | ACATGGGCAA | GCCGGTGATG | GACGCCTGGA | ACATCGATGT | 840 |
| ACCCGGCGCC | GCCCACGTCT | TCGCCTGGTA | TGCGGAAAGC | CTCGACAAGC | TCTACGACCA | 900 |
| GGTCGCGCCG | GCCGCCCAGC | AGACCCTGGC | CACCATTACC | CGCGTGCCGC | TGGGGGTGAT | 960 |
| CGGCGCGGTG | GTGCCGTGGA | ACTTCCCGCT | CGACATGGCC | GCCTGGAAGC | TCGCCCCGGC | 1020 |
| CCTGGCCGCC | GGCAACTCGG | TGGTGCTCAA | GCCGGCCGAG | CAGTCGCCGT | TCTCCGCCCT | 1080 |
| GCGCCTGGCC | GAGCTGGCCC | TGGAGGCGGG | GGTGCCGGAA | GGCGTGCTGA | ACGTGGTGCC | 1140 |
| GGGCCTCGGC | GAGCAGGCCG | GCAAGGCCCT | CGGCTTGCAC | CCGGAGGTGG | ACGCACTGGT | 1200 |
| GTTCACCGGC | TCCACCGAGG | TCGGCAAGTA | CTTCATGCAG | TATTCCGCGC | AATCCAACCT | 1260 |
| CAAGCAGGTC | TGGCTGGAGT | GCGGCGGTAA | GAGTCCGAAC | CTGGTGTTCG | CCGATTGCCG | 1320 |
| CGATCTTGAC | CTGGCGGCGG | AAAAAGGCGC | CTTCGGCATT | TTCTTCAATC | AGGGCGAGGT | 1380 |
| CTGTTCGGCG | AACTCGCGCT | TGCTGGTGGA | GCGTTCGATC | CACGACGAGT | TCGTCGAGCG | 1440 |
| CCTGCTGGCC | AAGGCCCGCG | ACTGGCAGCC | GGGCGATCCG | CTGGACCCGG | GCCAGCCGCG | 1500 |
| CCGGCGCCAT | CGTCGACCGC | CGGCAGACCG | CCGGGATTCT | CGCCGCCATC | GAGCGGGCGC | 1560 |
| AAGGCGAGGG | CGCGACCCTG | CTCGCGGTGG | CCGCCAGTTG | ACGATCAACG | GTTCGGACAA | 1620 |
| CTTCATCGAA | CCGACCCTGT | TCGGCGACGT | ACGCCCGGAC | ATGCAGCTGG | CCCGCGAGGA | 1680 |
| AATCTTCGGC | CCGGTGCTGG | CGATCAGCGC | CTTCGACTCC | GAGGACGAGG | CCATACGCCT | 1740 |
| GGCCAAGGAC | AGCCGCTACG | GCCTCGCCGC | CTCGCTGTGG | AGCGACGACC | TGCACCGTGC | 1800 |
| GCACCGGGTG | GCGCGGCGCT | TGAATGCCGG | AACGTGTCGG | TGAATACCGT | GGACGCGCTG | 1860 |
| GACGTCGCGG | TGCCTTTCGG | CGGCGGCAAG | CAGTCCGGCT | TCGGTCGCGA | CCTGTCGCTG | 1920 |
| CATTCCTTCG | ACAAGTACAC | CCAGTTGAAG | ACGACCTGGT | TCCAGTTGCG | CTGAAGACGC | 1980 |
| GACGGACGCG | ACACGACTCG | ATGCCGATAA | CGACAACAAG | AGGACGATCG | AATGAACGAC | 2040 |
| ACGCCGAACG | TGCGTGAGCC | GGCCCTGCGC | CGCGTGCTCG | GCTGGGACCC | GCTGCTGGCG | 2100 |
| GTGGCCATCG | GCCTGGTGGT | TTCCCAGGGC | GTGATGGTAC | TGATGCTGCA | AGGCGCCGGG | 2160 |
| ACGGCCGGCC | TGGGCTTCAT | CGTGCCGCTG | GGAGTGGCCT | ACCTGCTGGC | GCTGACTACG | 2220 |

-continued

```
CCTTTTCCTT TTCCGAGCTG GCCCTGATGA TTCCCCGCGC CGGTAGCCTG AGCAGCTACA    2280
CCGAGGTGGC CATCGGGCAT TTCCCGGCGA TCCTGGCGAC CTTTTCCGGC TACGTGGTGG    2340
TGGCGATGTT CGCCCTCTCG GCGGAACTGC TGCTGCTCGA CCTGATCATC GGCAAGGTCT    2400
ACCCCGGCGC GCTGCCGCCG ATGCTGGTGC TACGGCGTGC TCGGCCTGTT CACCCTGCTC    2460
AACCTGCTCG GCATCGACAT CTTCGCGCGC CTGCAGAGCG CGCTGGCGCT GCTGATGATG    2520
ATCGTCCTGC TGGTGCTCGG CCTGGGTGCG GTGAGCAGCG ACCACGCTTC CGCGCAGACC    2580
GCCCTGGCGA GCGGCTGGAA CCCGCTGGGG GTAAGCGCCC TGGCGCTCAC CGCGATGGCC    2640
GTGTGGGGCT TCGTCGGCGC CGAGTTCGTC TGCCCGCTGG TGGAGGAGAC GCGGCGTCCG    2700
GAGCGCAACA TCCCGCGTTC GATGATCCTC GGCCTGAGCA TCATCTTCCT GACCATCGCC    2760
CTCTACTGCT TCGGTGCGCT GCTGTGCATC CCGCAGGCGG AACTGGCCGG CGACCCGCTG    2820
CCACACTTCC TCTTCGCCAA CCGCGTGTTC GGCGAGTACG GCCAGCTGTT CCTGGTGATC    2880
GCCGCGATCA CCGCCACCTG CAGCACCCTC AACTCGTCGC TGGCGGCGAT CCCGCGGATG    2940
CTCTACGGGA TGGCGCAGAA CGGCCAGGCC TTCCCGCAAT TCAAGCAGCT CAGCCGGCGG    3000
GCGCGCACGC CCTGGGTGGC GGTGCTGTTC GTCGCCGCGA TCACCGGCCT GCCGATCCTG    3060
ATCCTCGGCC AGGACCCGGA CTCGATCAAC CTGCTGCTGC TCGCCGCCGC GCTGGCCTGG    3120
CTGCTGGCCT ACATCATCGC CCACGTCGAC GTGCTGGCCC TGCGCCGTCG CTATCCGCAC    3180
ATCGCCCGTC CGTTTCGCAC GCCGTTCTAC CCGCTGCCGC AACTGTTCGG CATCGCCGGG    3240
ATGATCTACG CGGTGGTCCA CGTCTCGCCG ACCCCGGAAA TGACCGGACG GATCTTCGCC    3300
AGCGCCGGCG TGGTGCTCGG CGTGGTCTCG CTGGTGGCGG TGGTGTGGAT CAAGGGCGTG    3360
ATGCGCAAGC CCCTCTTCGT ACCCGAACCG CTCGAGACGG CCGGTGAGAC TGCCCAGGGC    3420
AAGTCCGTCG CCCTCGATCC CCTGCAATCC CTTCGGCCTG ACGCGCCAAG GGAACAAGGA    3480
GAACACAGAC GATGACCGCT CAGCTCAACC CGCAGCGCGA CACCCGCGAC TACCAGCAAC    3540
TGGACGCCGC GCACCACATC CACGCCTTCC TCGACCAGAA GGCGCTGAAC CGCGAAAGGC    3600
CCGCGGGTGA TGGTCCGCGG CGATGGCCTG CAGCTCTGGG ACAACGACGG CAAGCGCTAC    3660
CTGGACGGCA TGTCCGGCCT CTGGTGTACC AACCTCGGCT ACGGCCGCCA GGACCTCGCC    3720
GCCGCCGCCA GCCGCCAGCT GGAACAACTG CCGTACTACA ACATGTTCTT CCACACCACC    3780
CACCCGGCGG TGGTGGAGCT TTCCGAGATG CTCTTCAGCC TGCTGCCGGA CCACTACAGC    3840
CACGCGATCT ACACCAACTC CGGCTCCGAG GCCAACGAGG TGCTGATCCG TACCGTGCGG    3900
CGCTACTGGC AGATCCTCGG CAAGCCGCAG AAGAAGATCA TGATCGGCCG CTGGAACGGC    3960
TACCACGGCT CGACCCTGGG CAGCACCGCG CTCGGCGGGA TGAAGTTCAT GCACGAGATG    4020
GGCGCATGCT GCCGGACTTC GCCCACATCG ACGAACCCTA CTGGTACGCC AACGGCGGCG    4080
AGCTGAGCCC GGCCGAAGTT CGGTCGCCGC GCGGCGCTGC AACTGGAGGA GAAGATCCTC    4140
GAACTGGGCG CGGAGAACGT CGCCGCCTTC GTCGCCGAGC CCTTCCAGGG CGCCGGTGGC    4200
ATGATCTTCC CGCCGCAAAG CTATTGGCCG GAGATCCAGC GCATCTGCCG GCAGTACGAC    4260
GTGCTGCTGT GCGCCGACGA AGTGATCGGC GGCTTCGGCC GCACCGGCGA ATGGTTCGCC    4320
CACGAACACT TTCGCTTCCA GCCGGACACC TTGTCCATCG CCAAGGGCCT GACGTCCGGC    4380
TACATCCCCA TGGGCGGCCT GGTACTCGGC AAGCGCATCG CCGAGGTGCT GGTGGAGCAG    4440
GGCGGGGTGT TCGCCCACGG CCTGACCTAT TCCGGCCACC CGGTGGCGGC GGCGGTGGCC    4500
ATCGCCAACC TCAAGGCTGC GCGACGAGGG CGTGGTCACG CGGGTCAGGG AGGAGACCGG    4560
CCCCTACCTG CAACGCTGCC TGCGCGAGGT CTTCGGCGAC CATCCGCTGG TCGGCGAGGT    4620
```

| | | | | | |
|---|---|---|---|---|---|
| CCAGGGCGCC | GGCTTCGTCG | CCGCGCTGCA | GTTCGCCGAG | GACAAGGTGA | CCCGCAAGCG | 4680 |
| CTTCGCCAAC | GAGAACGATC | TGGCCTGGCG | CTGCCGCACC | ATCGGCGGCT | TCGAGGAGGG | 4740 |
| CGTGATCATC | CGCTCCACCC | TCGGCCGCAT | GATCATGGCC | CCGGCGCTGG | TGGCCGGGCG | 4800 |
| TGCCGAGATC | GACGAACTGA | TCGACAAGAC | CCGTATCGCG | GTGGATCGCA | CCGCGCGCGA | 4860 |
| GATCGGCGTG | CTCTGACGCG | CCCCGGCGGC | CCGGCCTCGG | CCGGGTCGCC | TGCGACACGG | 4920 |
| AGCGTCCCCC | CATAACGACG | ATGCGGCGCC | TGGCGACCGC | GCGCGGAACC | GTTTCGGCCT | 4980 |
| CTGGCGGCAA | CTGCCTAAGC | AACATCACAA | CAATGCCAAT | CGGCTGTGGG | AGTGTTCCAT | 5040 |
| GTTCAAGTCC | TTGCACCAGT | ACGCACACGT | GTTTTCCCGG | TTGTCCCTGT | TCGTCCTGGC | 5100 |
| GTTCGCCGCG | GCGGCCCAGG | CGCAGAGCCA | GAGCCTGACG | GTGATCTCCT | TCGGCGGCGC | 5160 |
| GACCAAGGCC | GCCCAGGAAC | AGGCCTATTT | CAAACCCTTC | GAGCGAAGCG | GCGGCGGGCA | 5220 |
| GGTGGTCGCC | GGCGAATACA | ACGGCGAAAT | GGCCAAGGTG | AAGGCCATGG | TCGACGTCGG | 5280 |
| CAAGGTCAGC | TGGGACGTGG | TCGAGGTGGA | GAGCCCCGAA | CTGCTCCGCG | GCTGCGACGA | 5340 |
| GGGGCTGTTC | GAACGCCTCG | ACCCGGCGCG | TTTCGGCGAC | CCCGCGCAGT | TCGTCCCCGG | 5400 |
| CACTTTCAGC | GAGTGCGGGG | TGGCCACCTA | CGTCTGGTCG | ATGGTGATGG | CCTACGACTC | 5460 |
| GACGAAGCTG | GCCAGGGCGC | CGCAGTCCTG | GGCGGATTTC | TGGAACGTCC | GCGAGTTCCC | 5520 |
| CCGGCAAGCG | TGGCCTGCGC | AAGGGCGCCA | AGTACACCCT | GGAAGTGGCG | TTGCTGGCCG | 5580 |
| ACGGGGTGAA | GGCGGAGGAC | CTCTACAAGG | TACTCGCCAC | CCCGGAGGGG | GTCAGCCGCG | 5640 |
| CCTTTCGCCA | AGCTCGACCA | GCTCAAGCCG | AACATCCAGT | GGTGGGAGGC | CGGCGCCCAG | 5700 |
| CCGCCGCAAT | GGCTGGCGGC | CGGCGACGTG | GTGATGAGCG | CGGCCTACAA | CGGGCGCATC | 5760 |
| GCCGCTGCGC | AGAAGGAGGG | GGTGAAACTG | GCCATCGTCT | GGCCCGGCAG | TCTCTACGAT | 5820 |
| CCGGAGTACT | GGGCGGTGGT | GAAGGGCACC | CCGAACAAGG | CGCTGGCGGA | GAAATTCATC | 5880 |
| GCCTTCGCCA | GCCAGCCGCA | GACGCAGAAG | GTGTTCTCCG | AGCAGATCCC | CTACGGGCCG | 5940 |
| GTACACAAGG | GCACCCTGGC | GTTGCTGCCG | AAGACGGTGC | AGGAGGCGCT | GCCGACCCGC | 6000 |
| GCCGGCCAAC | CTCGAAGGCG | CGCGGGCGGT | GGATGCCGAG | TTCTGGGTGG | ACCACGGCGA | 6060 |
| GGAGCTGGAA | CAGCGTTTCA | ATGCCTGGGC | GCGCGCTGAG | CGCTGCGCGT | CGGCAAAAAA | 6120 |
| AATGACGGGC | CCCAAGTCGT | CCGGGCCCGT | CGGGTCAAAG | CGCTGACGGG | GTGATCAGCG | 6180 |
| CAGCTCTTCC | AACAACCCCT | GCAGATACCG | ACAGCCCTCG | GTATCCAGCG | CCTGCACCGG | 6240 |
| AAGGCGCGGC | GCCCCACCT | CCAGGCCGGA | GAGGCCCAGG | CCGGCCTTGA | TGGTGGTCGG | 6300 |
| CAGGCCCCGG | CGGAGGATGA | AGTCGAGCAG | CGGCAACTGC | CGGTAGAACA | GCGCGCGGGC | 6360 |
| CTTCTCCAGG | TCGCCGTCGA | GCACCGCCTG | GTAGAGCTGG | CCGTTGAGCG | TCGGGATCAG | 6420 |
| GTTCGGCGCG | GCGCTGCACC | AGCCTTTCGC | GCCGGCCACG | AAGGCCTCCA | GCGCCAGCGC | 6480 |
| GTTGCAGCCG | TTGTAGAAGG | GCACCCGGCC | TTCGCCGAGC | AGGCGCAGCT | TGTGCATGCG | 6540 |
| CTGGATGTCG | CCGGTGCTCT | CCTTGACCAT | GGTCACGTTG | TCCACTTCGC | GGACGATGCG | 6600 |
| CAGGATCAGT | TCCACCGACA | TGTCGATGCC | GCTGGTGCCC | GGGTTGTTGT | AGAGCATCAC | 6660 |
| CGGCACGCCG | ATGGCTTCGC | CAACCGCGCG | GTAGTGCTGG | AACACTTCCG | CCTCGTTGAG | 6720 |
| CTTCCAGTAG | GAGATCGGCA | GGACCATCAC | CGCCTCGGCG | CCGAGGGATT | CGGCGAACTG | 6780 |
| CGCGCGGCGC | ACGGTCTTGG | CGGTGGTCAG | GTCGGAGACG | CTGACGATGG | TCGGCACGCG | 6840 |
| ATGGGCGACG | GTCTTCAGGG | TGAAGTCGAC | CACCTCGTCC | CATTCCGGGT | CGCTCAGGTA | 6900 |
| GGCGCCTTCG | CCGGTGCTGC | CGAGCGGGGC | GATGGCGTGC | ACGCCGCCGT | CGATCAGGCG | 6960 |
| CTCGATGGAG | CGGCCGAGGG | CCGGCAGGTC | GAGACCGCCG | TCGGCGCCGA | AGGGGGGTGA | 7020 |

-continued

| | | | | | | |
|---|---|---|---|---|---|---|
| TGGTGTAGCC | GATGATGCCG | TGGATGGATG | CGGACATTGG | ATGTACCCGT | GACATTGAGT | 7080 |
| GGGAAATGCC | AGGACGGACC | TGGTGGGAAA | GGTCGTTCAG | CTCAGGCAGT | CGCTGTTGCG | 7140 |
| CGGCAGGCAG | CGCCGGGCGT | AGTAGTTGAA | TGCGGCGCCG | TGGCGCTTCG | GGGTGGAGAT | 7200 |
| CCAGTCGTGG | GCCTCGCGCG | CCAGGGCCGG | CGGGATCGGC | TTGATCTCTC | CGGCGGCCAT | 7260 |
| CGCCAGCAAC | TGCATCTTCG | CCGCGCGCTC | GAGCAGCACC | GCGATCACGC | AGGCCTCCTC | 7320 |
| GATGCTCGCA | CCGGTGGCCA | GCAGGCCGTG | GTGGGAGAGC | AGGATGGCGC | GCTTGTCGCC | 7380 |
| GAGGGCGGCG | GAGATGATCT | CGCCTTCCTC | GTTGCCTACC | GGCACGCCCG | GCCAGTCCTT | 7440 |
| GAGGAAGGCG | CAGTCGTCGT | ATAGCGGGCA | AAGGTCCATG | TGCGAGACCT | GCAGCGGTAC | 7500 |
| TTCCAGGGTC | GACAGCGCGG | CGATGTGCAG | CGGGTGGGTG | TGGATGATGC | AGTTGACGTC | 7560 |
| CGGGCGGGCG | CGATAGACCC | AGCTGTGGAA | GCGATTGGCC | GGATTCGCCA | TGCCGTGCCC | 7620 |
| GTGGAGGACG | TTGAGGTCTT | CGTCGACCAG | CAGCAGGTTG | CCGGCGCTGA | TCTCGTCGAA | 7680 |
| GCCCAGGCCC | AGTTGCTGGG | TGTAGTAGGT | CCCCGCCTCC | GGGCCGCGCG | AGGTGATCTG | 7740 |
| CCCGGCGAGC | CCGGAGTCGT | GGCCGGCCTC | GAAGAGAATC | CGGCAGGTCA | GGGCCAGCTT | 7800 |
| TTGCCGGTCA | GTCCACGTAT | TATCGCCGAG | GCTGCTTTTC | ATCTGCTTCA | GCGCGTGCTG | 7860 |
| GATCAGTTGA | TCCTTGGGTA | ATTCCAGTGT | CGTAACCATG | CGAGGTTCCT | TTGACGGAGC | 7920 |
| GAGTCGGGGG | AAACGCCAGG | CAGTTGCGCG | CCACGCAACG | ACCCGGCTGT | AAATGACACG | 7980 |
| GATCAAGTTA | TATGACACAA | AGTGTCATTT | AGCAAGAGAG | AAGTTTCATC | GCCATCGGGA | 8040 |
| GAAGGCTGTC | CTCAATGTCC | ATGCGCTTGA | AATTGCTGAG | AAAAAAACTC | GGGGTCACGC | 8100 |
| TGGAGACCCT | GGCCGACAAG | ACCGGCCTGA | CCAAGAGCTA | CCTGTCCAAG | GTCGAGCGCG | 8160 |
| GGCTGAACAC | GCCGTCCATT | GCCGCCGCGC | TGAAGCTGGC | GAAGGCGTTG | AACGTGCAGG | 8220 |
| TGGAGGAGCT | GTTCTCCGAG | GAAAGCGACG | GTGTCGACGG | CTACAGCATC | GTTCGTCGCG | 8280 |
| ACCAGCGCAA | GTCGCTGTCC | AGCGGCGACG | ACGGCCCGGC | CTACGCCTCC | CTCGTCGCAG | 8340 |
| CAGATCGGCG | CCCGCGCGCT | GTTGCCGTTC | ATCGTCCACC | CCCCGCGCGA | TTTCAGTCAC | 8400 |
| TCGACGTTCA | AGGAGCACCT | CGGCGAAGAG | TTCATCTTCG | TCCATGAGGG | CCAGGTCGAG | 8460 |
| GTCGACTTCA | TGAACCAGCG | GATCATCCTC | GAGCGCGGCG | ACGCCCTGCA | TTTCAACGCA | 8520 |
| CAGAAGCCGC | ACCGCATCCG | CTCCCTGGGG | GAGACCCAGG | CGGAATTGCT | GGTGGTGATC | 8580 |
| CACAGCGACG | AATGAGGCGA | CGGCTTCGGT | CGATCGGATG | CTTGCTAACG | TTCTGTTCGA | 8640 |
| TTATCGAACT | GTTAATCGAT | TATCGGATTG | TGAGCCCTCG | GACCCCGGCG | TAAGGTTCTC | 8700 |
| GTCACGTGCC | GTCCAGGCAG | CGCACAACAA | GACGAGACCC | GACCGATGGC | TGAAATCCTC | 8760 |
| TCCCTGCGCG | AACGGTGCGA | CGCTTCGTCC | ACGATGGCGA | CAGCGTCGCC | CTCGAAGGCT | 8820 |
| TCACTCACCT | GATCCCGACG | NCCGCCGGCC | ACGAGCTGAT | CCGCCAGGGC | AGGAAAGACC | 8880 |
| TGACGCTGAT | CCGCATGACT | CCCGACCTGG | TCTACGACCT | GCTGATCGGT | GCAGGCTGCG | 8940 |
| CGAAGAAGCT | GGTGTTCTCC | TGGGGCGGCA | ACCCCGGTGT | CGGTTCGCTG | CACCGCCTGC | 9000 |
| GCGACGCGGT | GGAGAAGGGC | TCGGCCGCAA | CCGCTGGAGA | TCGAGGAACA | CAGCCACGCC | 9060 |
| GACCTCGCCA | ACGCCTATTT | TGCCGGCGCC | TCCGGGCTGC | CCTTCGCGGT | NTGCGCGCCT | 9120 |
| ACGCCGGCTC | CGACCTGCCG | AAGGTCAACC | CGCTGATCCG | CAGCGTCACC | TGCCCGTTCA | 9180 |
| CCGGCGAAGT | GCTGGCGGCG | GTGCCCTCGG | TGCGTCCGGA | CGTCAGCGTG | ATCCACGCGC | 9240 |
| AGAAGGCCGA | CCGCAAGGGC | AACGTGCTGC | TCTGGGGCAT | CCTCGGCGTG | CAGAAGGAAG | 9300 |
| CGGCCCTGGC | GGCGAAGCGC | TGCATCGTCA | CCGTCGAGGA | GATCGTCGAC | GAACTGGACG | 9360 |
| CCCCGATGAA | CGCCTGCGTC | CTGCCGAGCT | GGGGCGCTCA | GCGCCGTGTG | CCTGGTGCCC | 9420 |

| | | | | | |
|---|---|---|---|---|---|
|GGCGGCGCGC|ATCCGTCCTA|TGCCCACGGC|TACTACGAGC|GCGACAACCG|CTTCTACCAG 9480|
|GACTGGGACC|CGATCGCCCG|CGACCGCGAA|AGCTT| | 9515|

( 2 ) INFORMATION FOR SEQ ID NO:14:

( i ) SEQUENCE CHARACTERISTICS:
        ( A ) LENGTH: 2471 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa
        ( B ) STRAIN: Clinical Isolate P2- 7

( x i ) SEQUENCE DESCRIPTION: SEQ ID NO:14:

| | | | | | |
|---|---|---|---|---|---|
|AAGCTTGTTC|CAGGCCCTCG|ACCGCTGCGA|TCTTCTGCGG|GTAGGCGGCG|ATGGTCTGTT 60|
|CGGAGTTCGC|CAACTGCAGG|CGACGCTGCG|CCAGCTGCGC|CGCCTGCACG|CCGGCAAGCA 120|
|TCAGGTCCTG|ATCGAGCGAG|GGGTTGAAGC|CGCGCACGAA|CTCGCTGAAC|TGGTCCACGC 180|
|CGAACAGGGT|GGCGATGAGC|TGGCGCTGAT|CGCTCGGGGT|CCGCGCGGCG|ATTCGGGCGA 240|
|AATCGTCGAG|GCGGTTCTTC|TCGATGAAGC|AGAAGCGATA|CTCAGCTTCG|TCGGGCTGGA 300|
|CGGCCTGCGC|CTCGCCCGCN|GCCGTAGACG|ACAGGACTGG|CGCGATGTGG|CGGCGCAGGC 360|
|GAGCGTTGTT|GCAGTACGTC|CGCTGGTCGA|CCGCTTGGCC|TGCGCTTCGC|TGATCGAACC 420|
|GAGCATCGCC|ACTTCCAAGG|CTTCGCAGAA|GCTGCTCTTG|CCGGTGCCGT|TGGCACGTNA 480|
|GACCAAGGTG|ATGTCATGGC|TGAGGTCGAA|CGTCTCCTGC|CGCATGAATC|CTCGAAACGG 540|
|CCCGACTTCG|AGCTGGTGCA|GTCGCCCGAG|CGCCGGCCCG|TTTTCGGGGC|CGCGCGCGTC 600|
|CCCGTCGTAG|GCGACAGGCA|TCTGCGCCAA|GATGCGCGAT|GGCCAGCGGC|GCCAAGCCGC 660|
|GTGGGAGCGC|CCCCCGGCGT|GCAGCACCGA|CCTCGGCCAG|TGGCTGCAGG|TGATCGAGCA 720|
|CCAGGGTGCG|CCAGCCGGCG|CACCGTTTCG|TCGTGCACGT|GCCGCTGCGT|CAAGTGCGCC 780|
|AGGAACCGGT|GGTACTCCGA|ACGTATGCTT|GCCACAGCGA|CCCCTCACTT|GGTCAACCAC 840|
|TGACCGTAAG|CCTCCACATC|GATCATGGGG|ACCGTTCCAC|TGAACTGAAG|CTGCGCGATC 900|
|AGCTTGAAAA|GAAACGCGGT|CGCCGGCTTG|TTTTCGTTGG|TGTAGCTGTA|CGCGCCGCTG 960|
|GCTTGGTCAT|AGAAAAAGTG|CCCGTGGGCG|GCAACGCATC|CGATGTCCAG|ACGCCCCTCG 1020|
|GTGAGGTTTG|CGTTCAGCGC|CTTGTCCATG|GATGGGCCCA|ATGCAGGACT|CCATTCGCTC 1080|
|TCGAAGGTGA|GCAAGCCACC|CAGAATCGGA|ATCAACGCTT|CGCTGGGTAG|GTCCCGCCAG 1140|
|CGTGCGGGAT|CGGCAGGCTC|GTGCGGTGCA|GCCTGCGCAC|ACTGGCGACC|TTCTCCTGGC 1200|
|ATAGCCACAA|GCCCCGCGTC|AGCCGTCTGC|TTGGCCTCGA|ACACGGCGTA|CACGCTTTCG 1260|
|GCTGGAATGA|TCGTCTCGTT|CTCGTAGGTG|AAGATAAAAG|GCGAATATTG|CCGATCAAAC 1320|
|ACCACCACAT|CGATCTGCTG|GCTGAAGTTC|CCCAGGCTGT|CCACCACATG|CGCCTTCGCC 1380|
|GCCTGGTACC|GTTTGGGCAG|ATAGGTATCC|AGCATGTCGA|TCCAGACGTT|CTCGCTCGCA 1440|
|TCCCCCTTCG|TACCCGGGTG|ACCGAAGGTC|TTGCGTACTA|CGGACAAGCG|CTGCTGGATG 1500|
|TCTTCATGCA|GGGACGACAG|GAGCTGGGAA|AGCGACCACT|GGGACATGCT|GTACCTCGAT 1560|
|GGGACGTGTA|TGGAAGCCGA|TGGAATCAGG|ACAGTGGGAA|CTTGGGGCCA|AACAGTGCGC 1620|
|GCCAGGGCGA|AGCGCTTCGA|TATTGCGACC|ACGACGCGTG|TGGTCGATGG|CGATGCTTGC 1680|
|GTCCTGGCTC|GCCTGGAACA|GCAGCTGCTN|GCGNGCGCTG|CTTGCGCGCG|GCATCCATAT 1740|
|CGTTGCTGAT|CGCCGGGCCA|AGTCCGGCGG|GATCCGGCCA|CTCGTCATGA|ACACGATCGG 1800|

-continued

| | | | | | |
|---|---|---|---|---|---|
|CAAGCGTGGC|AAAGAACGAC|TGGATCTCGC|GATCGAACGA|TCCTCCCCAG|CCGCCGTAAA|1860|
|GACACTCAAG|GGCCATTACC|TCGATCAGGA|ACGAGGGCTT|CACCGGCTTC|TGATCGCCGT|1920|
|GCTTGGGATT|GTTGTTCCAG|TACTTCACCA|TGCGCACGAG|ACCTTTCCAC|TCATTGCCAT|1980|
|AGGCTTGGTG|CGCTGCGGTC|GCCTTGTCCT|TATGGATCTC|CGGGTCCGTC|TTGATCCACT|2040|
|TTCCGGACGC|CGTATCGGGG|ATCTCATACT|GGTCGCCGGT|GTCGAATGCG|GGCACCGCAT|2100|
|CCACGCTGAC|CACCCGGTAG|TCCGTGTTGT|CCTCCGCGTC|GATGTGAACA|CCGAAATCCA|2160|
|CGTTGATCGA|GNGCGCCTGT|TTGCGCACGG|CCGCCGAACC|GTATTTCTCC|ACCAATGCAG|2220|
|AGTGGAAATC|ATCCAGCACT|ACCGATGCGG|CCTTGCCGTG|GTAATGCTTC|TCCGAGTCCT|2280|
|TCAGCACGAA|GAAGATGTCG|ATATCCTTGA|GCGGCTTCGT|CTTCGTGTAT|CGAGCATAGG|2340|
|ACCCGGTCAG|GAACTGCGCG|CAATGCCGAA|CTTGGTCTGC|AGGTAGTCCC|GCACTTCGTT|2400|
|CTGGCGTTGC|GAGGCATTCT|TCTGCTCGCG|TTCGTTGAGT|TCCAGACGCG|ACTTGAACTT|2460|
|GCGAAAAGCT|T| | | | |2471|

( 2 ) INFORMATION FOR SEQ ID NO:15:

( i ) SEQUENCE CHARACTERISTICS:
      ( A ) LENGTH: 5247 base pairs
      ( B ) TYPE: nucleic acid
      ( C ) STRANDEDNESS: double
      ( D ) TOPOLOGY: linear ( i i ) MOLECULE TYPE: Genomic DNA ( v i ) ORIGINAL SOURCE:
      ( A ) ORGANISM: Pseudomonas aeruginosa
      ( B ) STRAIN: Clinical Isolate P2- 17

( x i ) SEQUENCE DESCRIPTION: SEQ ID NO:15:

| | | | | | |
|---|---|---|---|---|---|
|AAGCTTCGAG|GGGGCTGGGC|GAGGATCGAC|CGGCCCCGCT|CGTGTCGGAA|GGGAAGGCCA|60|
|GGGCTGGCCT|GCCCGTTCGG|CGCTTCGGCA|GGCTGGCGCA|GAACGATGCA|AGGTCGTTCG|120|
|GGTCAGCATC|AGGGATGAAA|TGACTGACAG|GAGTCGGGAT|GCTGCGTTAC|GTCGTGGGTT|180|
|TTCTCGCGTT|CACCGTGCTG|GCGGCCTATC|TGTTGCTGGG|GGTTTCCCAG|CACGCCTTCC|240|
|TGCCGTGACC|GGTCGGCATG|GCGGCTTCAG|CTGCGTTGCG|GAAGAGGCTG|TGGCGGCCGT|300|
|GCGGGATGCC|GGTTTTCGGC|TTGCCGTGCC|TTGCGTTGCA|GGCGTCGCGC|CGACGCGGCA|360|
|CGCCAGGGAA|GGCCCACAGG|GTGACGCCGG|CGAGGCCCAG|CCAGGCGACG|ATCAGCAATG|420|
|TGACGAAGGA|TTCGGGAGTC|ATGGTTCGTC|CTCCTCTTAC|CCAAGGATAG|ACCCTGCGGG|480|
|AAGGGGAATT|ACTGCAATCG|GTCTTCGACC|ATGGTCTGAA|ACGCGGTCAC|TCGGGCCGG|540|
|CGCCGACCAG|GGCCAGGCAG|CCGGTGAGGC|TGGTCAGCAG|GGGCAGGGCG|AGCAGGAAAG|600|
|CCAGCCAGAT|GGCCTCCATG|CGCAACAGCG|TGGCGCCGAG|GAACAGCGCG|ACCAGGAGGA|660|
|TGGTCATGAG|CAGGGCGGTC|CAGCCGAAGT|ACATGGCGAA|GTTGTCGATG|CCCAGGCCGA|720|
|TGCCCCAGCC|CAGCAGCAGG|GCCCATACCC|CGGCCAGAGC|CAGGCCGAGG|GCCAGCATGC|780|
|TCGCCAGGGT|CCGGCGGAC|GGGGCATGCA|GCGGGTGGTT|GCGGAATAGC|TCGTAGAAGA|840|
|TCGGCGTATT|CATCGGCGTC|ACCTCCGCAG|GGGAACTTCC|AGCCTAGTCC|AGCGGGCGAG|900|
|ACGGCCCTAG|ACCTATTTGT|CATTACGAGG|CGTGACCTCA|GGCCGTTAAC|ATCCATCTTT|960|
|TTCCAGGCGA|TGCCGTGCAT|CGGGCTGCGG|GCCCGCTCAC|CGTTCGTCGC|GCTGAGTCGA|1020|
|AAAAGAAACC|GAAAGGGTTG|CGTGCATGAG|TTGGCGAACT|CGCCTCGTTC|GAGGTGGATG|1080|
|GGTATCAACT|GGTCTATCAG|GACCTGGGTG|AAGGCACGCC|GGTGCTACTG|GTCCACGGTT|1140|

-continued

```
CGCTGTGCGA CTACCGCTAC TGGCAATGGC AGTTGCGCAG CTCGGCAAGC ACCACCGGCT   1200
GATCGTGCCG AGCCTGCGTC ACTACTACCC CGAGCGCTGG GACGGGCAGG GTGCGGACTT   1260
CACCAGCGCC CGCCACGTCG CCGACCTGCT GGCGCTGGTC GAGCGGCTCG GCGAGCCGGT   1320
ACACCTGCTC GGCCATTCCC GTGGCGGCAA CCTGGCGTTG CGCCTGGCGC TGGCCGCTCC   1380
GGACGCCCTG CGTTCGCTGA GCCTGGCCGA TTCCCGGCGG CGACTATGCC GCCGAGGTCT   1440
ACGCCCACGC CGGCCTGCCT GCGCCCGAGG AACCATTGGA ACGCAACCAG TTCCGGCGCC   1500
AGGCGCTCGA ATTGATCCGT GGCGGCGAGG CGGAACGGGG ACTGGAACTG TTCGTCGATA   1560
CGGTGAGCGG CGCCGGGGTA TGGAAACGCT CGTCGGCGAC GTTCCGCCGA ATGACGCTGG   1620
ACAACGCCAT GACCCTGGTC GGGCAGGTGG CCGACCAGCC GCCGGCGCTG GCGCTGTCGG   1680
AACTGCGCTC GATCGACCTG CCGAGCCTGA TCCTCAATGG CGAACGCAGC CCGCTGCCAT   1740
TCCCGGCCAC CGCCGAGGCG CTGGCGGCGG CCCTGCCGCG CGCCGAGCTG CAACGCATCC   1800
AGGGCGCGTC CCATGGCCTC AATGCCACCC GTCCGGCGGC TTTCAACCGG TCGGTGCTGG   1860
AGTTCCTGGC GCGCGTCGAT GGCGTTGCGC CGGACGTGGA AACGTCCTGA AGCGAGGCCG   1920
GGCGAACTGA CCGCTCGTCA GCTCGCCGCG GATGCTTTAC CATGCGTTCG CGCCGGATCA   1980
GCTCCGGCGT TTTTCGTCAG TATCCATTCC CAGTGATCTC CGTCCGCGCG CTTCGGCGCA   2040
GGGGTGCCGC AAGGCGCCTG CCACTGTGAG GCAGGCCGGC CCGGCGGGCG ACGCTTACTG   2100
GCACATCCCA ACCCACGTGG CCTTTGGTAG GGTCACCACT AGAGAGAGCG CCATGCCCAT   2160
CATTACTCTT CCCGACGGCA GTCAACGTTC CTTCGATCAC CCGGTCTCCG TGGCCGAGGT   2220
GGCCCAATCC ATCGGCGCAG GCCTGGCCAA GGCGACCCTC GCCGGCAAGG TCGACGGCCG   2280
CCTGGTCGAC GCCTGCGACA CCATCGATCG CGACGCGACC CTGCAGATCA TCACGCCCAA   2340
GGACGAGGAA GGACTGGAGA TCATCCGCCA CTCCTGCGCC CACCTGGTCG GCCATGCGGT   2400
CAAGCAGCTC TATCCGACCG CGAAGATGGT CATCGGCCCG GTGATCGAGG AAGGCTTCTA   2460
CTACGACATC TTCTTCGAGC GCCCCTTCAC CCCCGAGGAC ATGGCGGCGA TCCAGCAGGC   2520
ATGCGCGAGC TGATCGACAA GGACTACGAC GTGATCAAGA AGATGACCCC GCGCGCCGAG   2580
GTCATCGAGC TGTTCAAGTC CCGTGGCGAA GACTAACAAG CTGCGCCTGA TCGACGACAT   2640
GCCGGACGAG AAGGCCATGG GCCTGTACTT CCATGAGGAG TACGTGGACA TGTGCCGCGG   2700
CCCGCACGTG CCGAACACTC GCTTCCTCAA GGCGTTCCAG CTGACCAAGA TTTCCGGCGC   2760
CTACTGGCGC GGCGACTCGA AGAACGAGCA GTTGCAACGC ATCTACGGCA CCGCCTGGGC   2820
CGACAAGAAG CAACTGGCGG CCTACATCCA GCGCATCGAA GAGGCCGAGA AGCGCGACCA   2880
TCGCCGCATC GGCAAGCAGC TCGACCTGTT CCACCTGCAG GAAGAAGCGC CGGGCATGGT   2940
GTTCTGGCAC CCGAATGCTG GAGCGTCTAC CAGGTGCTCG AGCAGTACAT GCGCAAGGTC   3000
CAGCGCGACC ATGGCTATGT CGAAGTGCGT ACCCCGCAGG TGGTCGACCG CATCCTCTGG   3060
GAGCGTTCGG GCCACTGGTC GAACTACGCC GAGAACATGT TCACCACCTC CTCGGAAAGC   3120
CGCGACTACG CGGTCAAGCC GATGAACTGC CCGTGCCACG TGCAGATCTT CAACCAGGGC   3180
CTGAAGTCCT ACCGCGACCT GCCNTGCGCC TCGCCGAGTT CGGCGCCTGC CACCGCAACG   3240
AGCCGTCCGG CGCGCTGCAC GGATCATGCG GTACGCGGCT TTACCCAGGA CGACGCGCAT   3300
ATCTTCTGCA CCGAAGAGCA GGTGAAGAAG GAAGCGGCCG ATTTCATCAA GCTGACTTGC   3360
AGGTCTACCG CGACTTCGTT TCACCGACAT CGCCATGAAG CTGTCGACCC GTCCGGCCAA   3420
GCGCGTCGGT TCCGACGAGC TGTGGGATCC CGAAGGCGCG CTGGCCGATG CGCTGAACGA   3480
ATCCGGCCTG GCCTGGGAAT ACCAGCCGGG CGAGGGCGCG TTCTACGGGC CGAAGATCGA   3540
```

-continued

```
GTTCACCCTG AAGGACTGCC TCGGCCGTAA CTGGCAGTGC GGCACCCTGC AGTACGACCC    3600
GAACCTGCCG GAGCGCCTGG ACGCCAGCTA CATCGCCGAG GACAACAACC GCAAGCGCCC    3660
GGTGATGCTG CACCGTGCGA TCCTCGGGTC CTTCGAGCGC TTCATCGGCA TGCTCATCGA    3720
GCACTACGCC GGAGCCTTCC CGGCCTGCTG GCGCCGACCC AGGCAGTGGT GATGAACATC    3780
ACCGACAAGC AGGCCGATTT CGCCGCCGAG GTGGTGCGGA TCCTCGGGGA AAGCGGATTC    3840
CGTGCCAAGT CCGACTTGAG AAACGAGAAG ATCGGCTTTA AAATCCGCGA GCATACTTTG    3900
CTCAAGGTTC CCTATCTCTT GGTTATTGGA GATCGGGAAG TTGAATCGAA GGCCGTCGCG    3960
GTGCGTACGC GCGAAGGGGA AGACCTGGGC TCCATGCCCG TCACCCAGTT CGCTGAGCTG    4020
TTGGCACAGG CGGTTTCCCG GCGTGGTCGC CAAGACTCGG AGTAATCATT ATTAAGCGTG    4080
AAATGAGACA GGATAAGCGA GCTCAACCGA AACCCCGAT  CAACGAGAAC ATCTCGGCTC    4140
GTGAGGTACG GTTGATTGGA GCTGATGGCC AGCAGGTTGG TGTTGTTTCG ATCGATGAGG    4200
CGATCCGCCT AGCCGAAGAG GCGAAGCTGG ACCTGGTTGA GATTTCGGCC GACGCGGTGC    4260
CTCCTGTCTG CCGCATCATG GACTACGGCA AGCACCTGTT CGAGAAGAAG AAGCAGGCTG    4320
CGGTCGCCAA GAAGAACCAG AAGCAGGCGC AGGTCAAAGA AATCAAGTTT CGTCCAGGGA    4380
CGGAAGAAGG GGATTACCAG GTAAAACTAC GCAACCTGGT ACGTTTCCTT AGTGAAGGGG    4440
ACAAGGCCAA GGTATCCCTG CGATTCCGCG GCCGTGAGAT GGCTCACCAG GAGCTGGGGA    4500
TGGAGCTGTT GAAGCGGGTC GAAGCCGACC TCGTGGAGTA CGGCACCGTC GAGCAGCATC    4560
CTAAGCTGGA AGGACGCCAG CTGATGATGG TCATCGCTCC CAAGAAGAAA AAGTAACCAC    4620
CAGGGCACTG GCAGGCCTTG CGGTTATGCG TAATCACTCA ATGCGGAGTA TCCGAACATG    4680
CCAAAGATGA AGACCAAAAA GTGGGCGCGG CCAAGCGCTT CAAGAAGACT GCTGGTGGCC    4740
TCAAGCACAA GCACGCCTTC AAGAGCCACA TCCTGACCAA GATGACCACC AAGCGTAAGC    4800
GTCAACTGCG CGGCACCTCG ATGCTGAACA AGTCTGACGT TGCGCGCGTA GAACGCTCCC    4860
TGCGTCTGCG CTGATTATTA AGGTAGAGGA TTAATTCATG GCTCGTGTTA AGCGTGGCGT    4920
TATCGCCCGT CGTCGTCACA AGAAAATTCT GAAGCTCGCC AAGGGCTACT ACGGTGCACG    4980
CTCGCGCGTG TTCCGCGTTG CCAAGCAGGC GGTGATCAAG GCTGGCCAAT ACGCCTACCG    5040
TGACCGTCGT CAGCGCAAGC GTCAGTTCCG CGCACTGTGG ATCGCCCGTA TCAACGCTGG    5100
TGCTCGTCAG AACGGTCTGT CCTACAGCCG CCTGATCGCC GGCCTGAAAA AGGCGGCCAT    5160
CGAGATCGAC CGTAAGGTCC TGGCCGATCT GGCAGTGAAC GAAAAGCGG  CGTTTACCGC    5220
GATTGTCGAG AAAGCGAAGG CAAGCTT                                        5247
```

( 2 ) INFORMATION FOR SEQ ID NO:16:

( i ) SEQUENCE CHARACTERISTICS:
        ( A ) LENGTH: 2812 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa
        ( B ) STRAIN: Clinical Isolate P4- 5

( x i ) SEQUENCE DESCRIPTION: SEQ ID NO:16:

```
AAGCTTTGGT GATCTTAACG TGACAAGCTC CTTAGAAAAA TTTTATGAGT TTATTAGCGG      60
GGTCTTTCTT GATCCGACTG TACCAAGACT TTCAACTCGT AAAATACGCA AGCACAAAAG     120
CACTGAAATG CACTCTGCAC GTTTGTCGCC GTCCACGGTA GCGGCATCCC TCAATCACAC     180
```

-continued

```
CGAAGCGGTG AATCTTTCTA CCTATGCAGA GGCAACACCT GAACAGCAGC AATCCGAGTT    240
CAGCCTGTTT TGGGATGCAA TACGCCACGC TGCTCATGTT GTGCGTGAGC GAAGCCGCAA    300
GGCTGTAGCA AGTAGTGTCG CAATAGCGGC GGGTCACTGC GAGGATTTCA ATAAGCCGAC    360
GTCTGCCACT GATGTGGGAT TGATTATAGA GCCGAACTGC CGCACCCAAT ATGGTTGTTT    420
GTACTGCGAA AACTATTTAT GTCACGGCGA TGAGGAGGAT CTGCATAAAA TTCTGAGTTT    480
GCAATACGTG GTCAATGCCG TGCGTAAATC GGCCCCGAT GCAGCGCATA CTGAGGCACT    540
TTTCAAAGAG TTATCTATCC GGATCGAGTT TATAGTCGAT GCTCTTAGTG AGCGCTCTAG    600
CTCGGTGAAA CAGACAGTCG AAAAGGTTAA AGCTAAGGTG TTTGAATACG GCGAGTTAAC    660
TAAGTTTTGG GAAGTCCGGT TGGGTCGCTA TGAAAAAATG GGGATCGTAT TTGAGTGCT    720
GCTGTTCAGT CGATAGGTAG TCTTTTTTCT AGCGGCCAGT TTCCAGTCAC CAGCCAGCCA    780
GATAGTGCGG CTCAGCTGTA TGGGAAGCCC GCGTCGGATT TTGTTATCTG TCGCACTGAG    840
TATGGCAATG CAACGGCAGT GTACGGCGAG TCTGTATGGG ACTTTAACCC GTACAGGCTG    900
AGTGCAAAAA AAATTGGCCG AATACGCTTC GATATGGTGT TCGGTGATTA TGGTCATGAT    960
CAGCAAGCGC TGATCGAAGA AGCCAAATAT CTTCTGTATT GTCTTATTTA TTTCGCTGGC   1020
GGTGGGCGGA TTGGTAAGCT GAGTGCATCT ACGATTATTT CATATTGGGT TGTGCTGCGC   1080
ATCGCTATGA AGTTCTGCTA TGCGCAGAAA AAGAAGTCAA TGGTTGGTGT GCTGTCCTTG   1140
CAGCAGCTTT TTACCGTGCC TGTTTATCTA GCGGCTTTTG TTAGTGAAAG TAATTTTGAC   1200
AAGACGGTTC TTAGTGGGAT ATTGCACGGA TTGATTAGTG TGGGCGAGGA ACGCCTAGGG   1260
TATGTTGTGC TGAATCCAAG AGTTTTTGAT TTGAGAAGAC CTGATTCTAA ACAGCATTCC   1320
GGTAATTCCG ACACGCCTTT ATTGAATTT AATAATATTG TGGCGACCTG CTCGATCATC   1380
TTACTTGGGT GTTGGGAATA TTGATTCATT TATATCGTGC TTTGCTGATG AGTATTTCGG   1440
TCTTACTCCG CACCGTCAAA AATCTTTGGG GGTTGGTGGT AAGTCGCGCT ATCGCCCCGG   1500
TATTCAGCAA GCAATAGAGG AATATGGTCT GGCTGCGGTT TTTGTCGGTG AGTTTGCCTG   1560
TTCCGAAAAG AGAAAGCTGC AGCGAGTCCT TCTCAAGATG CAGTATGTGG TGAGAATGGT   1620
GATACACCTA TATACCGGCA TGCGTGATCA AGAGGTGATG CGTATGTCTT ATAACTGCTT   1680
ATCTGATCAA GTCGTGAGAT GTTCAGTGGT TGATGATCAA GGTTTTATGC GCGATCAACC   1740
GCAATCAGTA CACATATTAT CGACTACCAC GAAGTTTAGC GGTTACAAGA AAGAAAGCGC   1800
ATGGTTCGCG GCAGGCGAAG TCGTCAAGGC GGTCGAGGTT GGCCAGGCGA TTTGTCGTGG   1860
TTTAGCCCGG CTCTATAGGA TTGAACTGGA TGATCGTTGT CCGCTATTCA TCAATCCGTC   1920
CGTCCTGTGT AAAACGAAGA ATTGTGCAGA AGTTGGTGTA ACAGACTTTA CATTGAGAGC   1980
AACGATGGCA GTGCTTTGAA ATCCTTATCG ATTCAATCAG AGGATTTACA AGAGTTGGCT   2040
CAGAGCGACC CTTCTCGTGA CTTTTACAAT GAGCCAGATT TTGCAGTAGG CCAGCCCTGG   2100
CCGCTGACTA GCCATCAATT CCGACGTTCG TTGGCCTTCT ATGGAAGCAG TAGCGGCTTT   2160
CTCTCGTTAC CGACTCTGCG AGCGCAGTTC AAGCATATGA CCCATTCAGA TGGCGCGCTA   2220
TTATGCGAAT GGCTTTGATA ACTTGCGCAC CATTTTTGGC TACTATGACG AGAAGAAAAT   2280
AGACTTCGTG CTACCATATA ACCACTTTGC TTTCGAGTTC CAGATGGCCA TGCCGATGTC   2340
GGTGGCCAAT CAGTTGATTG CAGATCTGCT GTTCAAAGAA GAACCGCTGT TGGTGGCAC   2400
CGGTTCATAC ATGCAGAGGC AGAAAGAACG TGTTGAAGCT GGCGAGATAA AGATTGAAGA   2460
TATTCGTGCC GATACAGAGC TTCGGGTGAA GAACGGTGCA ATTAGCTATC GGCCAACGCT   2520
ACTCGGTGGT TGCACCAAGG TGGGCCGCTG CGATTCCTTC ATGCTCGGTG ACTATACTGA   2580
```

| | | | | | |
|---|---|---|---|---|---|
| ATGTTTGTCC | TGCGAGGGTG | CGATTATCAA | GCCCTCCAGG | TTAAGTGCGG | CCATTGAGGA | 2640 |
| TGCGAAAAAC | GAGTTGTCAA | ACTACGCAGA | AGACTCAGGC | GAATATCAAA | TTGTGAAGGG | 2700 |
| CGATATTGAG | CGCCTAATGG | TTTTCAAGAC | TCGCCTGATC | GACACTGTGG | AGCTTTAGTC | 2760 |
| ATGAAGTCTG | GTGAAGGAAT | AAGCAAGGGG | GTTGGTGCCT | GTCAGGAAGC | TT | 2812 |

( 2 ) INFORMATION FOR SEQ ID NO:17:

( i ) SEQUENCE CHARACTERISTICS:
        ( A ) LENGTH: 3615 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Escherichia coli
        ( B ) STRAIN: Clinical Isolate EC- 24

( x i ) SEQUENCE DESCRIPTION: SEQ ID NO:17:

| | | | | | |
|---|---|---|---|---|---|
| AAGCTTTTCT | TGCGTGTTCT | TGTGAGGCTT | CCTTCGCCAT | TATCATCACG | ATCCACATAA | 60 |
| ATAAAGCCGT | AGCGCTTAGA | CATTTGTGAA | TGAGATGCAC | TGACTAAATC | AATTGGCCCC | 120 |
| CAACTGGTGT | ACCCCATAAT | ATCCACACCA | TCGGCAATCG | CTTCATTTAC | CTGTACCAGG | 180 |
| TGATCGTTTA | AATAGGCAAT | TCGATAATCG | TCCTGTATCG | AACCATCCGC | TTCAACGCTG | 240 |
| TCTTTTGCGC | CTAATCCGTT | CTCGACAATA | AATAACGGTT | TTTGATAACG | ATCCCAAAGC | 300 |
| GTATTTAACA | GAACCCGTAA | TCCAACCGGA | TCAATTTGCC | ACCCCACTC | TGAACTTTTC | 360 |
| AGATGCGGAT | TGGGGATCAT | ATTCAGTATG | TTGCCCTGCG | CATTTTTATT | AATGCTTTCG | 420 |
| TCGTGGGAAC | ACAACCAGTC | ATGTATAACT | AAAGAGATGA | ATCGACGGTA | TGTTTTAAAT | 480 |
| CTCTGCGTCA | CTTTCAGTCA | TCTCAATGGT | GATATTGTGG | TCGCGGAAGA | AACGCTGCAT | 540 |
| ATAGCCGGGA | TACTGGCCAC | GCGCCTGAAC | ATCACCAAAG | AACATCCAGC | GCCGGTTCTC | 600 |
| TTCCATGGCC | TGCAACATAT | CCTGTGGCTG | GCAGGTGAGG | GGGTAAACCA | GCCCACCGAG | 660 |
| AAGCATATTG | CCGATTTTCG | CTTCGGGGAG | CAGGCTATGA | CAGGCTTTAA | CTGCCCGCGC | 720 |
| ACTGGCAACC | AGTTGATGGT | GGATAGCCTG | ATAAACTTCC | GCCTCGCCAC | TCTCTTCTGC | 780 |
| CAGCCCCACG | CCCGTGAATG | GCGCGTGTAA | CGACATGTTG | ATTTCATTAA | ACGTCAGCCA | 840 |
| TAACGCCACT | TTATGTTGGT | AGCGAGTAAA | GACCGTGCGG | GCGTAATGTT | CGAAGTGATC | 900 |
| GATGACCGCT | CGATTAGCCA | ACCGCCGTAG | TTTTCACCA | GCCCATATGG | CATTTCGTAA | 960 |
| TGGGATAACG | TTACCAGCGG | CTTGATCCCC | GCCTGCGCCA | TTTCATCAAA | CAGCCGATCG | 1020 |
| TAAAACGCTA | ACCCCGCTTC | ATTCGGTTCG | ACTTCGTCGC | CCTGAGGGAA | AATTCGCGCC | 1080 |
| CAGGCAATGG | AAATACGCAG | ACAGGTGAAG | CCCATCTCGG | CAAATAACGC | GATATCTTCC | 1140 |
| GGGTAACGGT | GATAAAAATC | GATGGCGACA | TCTTTGATAT | TCTCTTTCCC | CAGGATGCGC | 1200 |
| GGTTCCATTT | TTCCCATTAC | GCATGAGGCT | GTAAATCTGA | GGTCGAGATC | CCTTTGCCAT | 1260 |
| CTTCCTGCCA | GGCACCTTCC | ACCTGATTGG | CAGCTGTTGC | GGCACCCCAA | AGAAATGTTT | 1320 |
| CTGGAAATGC | TTTCATAATT | AACTCCTTTT | ATCGTTAGCG | AATGATGGAT | AACAGCGGTT | 1380 |
| CACCTGCGCT | TATCTGCGCC | GTGCCGTGGG | GTAATACGTC | CGTAAAATCA | TCGCTATTAC | 1440 |
| TGATTAATAC | CGGCGTCGTC | AGATCAAATC | CGGCCTCGCG | AATAGCAGGG | ATATCAAAAG | 1500 |
| AAATCAGCCG | ATCGCCTGTA | TTGACCTTGT | CACCCACGTT | GACGTGAGCG | GAAAGAATT | 1560 |
| TGCCGTCCAG | TTTTACGGTG | TCGATACCGA | CATGAATCAG | GATCTCCACA | CCATCATCTG | 1620 |

| | | | | | |
|---|---|---|---|---|---|
| ACTCAATGCC | AATGGCGTGT | AATGTGGCGA | ACAACGAAGC | AATTCGACCC | GCAACCGGAG | 1680
| AACGCACTTC | ACCAACCGAG | GGCAGAATGG | CAATACCTTT | ACCCAACAGG | CCACTGGCAA | 1740
| ACGTGGTATC | AGCGACGTGA | ATGAGCGACA | CAATCTCTCC | CGTCATCGGT | GAACAGATAC | 1800
| CGCCCTGCTC | AGGTGGTGTA | ATAACCTCTG | GTGTTTTCTC | TTCGGGGCAC | CCTGCGCTGG | 1860
| CTGACGTTTA | GCGGTGATGA | AATGAAGCAT | CACCGTACCG | ACAAATGCGC | AACCGATGGC | 1920
| AATGACACCG | CCAATAACGC | TGGCCCAGAC | GGTGAAATCA | ATTCCGTTG | ACGGGATGGT | 1980
| TTGCATGAAG | GTGAAAATAC | TTGGCAAACC | AAAGGAGTAG | ACTTTCGTTT | GCGCGTAGCC | 2040
| AATAATGGTG | GCCCCAAAG | CCCCACTGAT | ACAGGCGATA | ACAAGGGGT | ACTTACGCGG | 2100
| CAGGTTGACG | CCATATACCG | CTGGTTCGGT | GATACCAAAC | AGACTCGTCA | ACGCCGCTGA | 2160
| TCCCGCCACC | ACTTTTTTCT | GCGCATCGCG | TTCGCAGAGG | AAGACGCCGA | GCGCCGCCCC | 2220
| GACCTGCGCC | ATAATGGCGG | GCATTAACAG | CGGGATCATG | GTGTCGTAGC | CCAGCACGGT | 2280
| GAAGTTATTG | ATACACACCG | GCACCAGGCC | CCAGTGCAGT | CCGAACATGA | CGAAGATTTG | 2340
| CCAGAAGCCG | CCCATTACCG | CGCCCGCAAA | TGCAGGAACC | GCCTGATAAA | GCCAGAGATA | 2400
| ACCGGCGGCA | ATCAGTTCGC | TTATCCAGGT | TGATAGCGGC | CCCACCAGCA | GAAAGGTGAC | 2460
| GGGTGTGATA | ACCATCAGAC | ATAGCAATGG | TGTGAAGAAA | TTTTGATTG | CCGACGGTAA | 2520
| CCACGCATTA | AGTCGGCGTT | CCAGAATGCT | GCACAACCAG | GCAGAAAAA | TAATGGGAAT | 2580
| AACCGATGAC | GAGTAATTCA | ACAATGTGAC | CGGAATACCC | AGGAAATCCA | GCCCCAGCGC | 2640
| ATCCGCTTTT | GCGCGTTCTC | GAAAAGCAGT | ACAGAATTAA | TGGATGCACT | AACGCTCCAC | 2700
| CAATCACCAT | GGCAGTAAAT | GGATTATCGC | CGAAGCGTTT | CCCCGCGGTG | TATCCCAGGA | 2760
| TTATCGGGAA | GAACCAAAAC | AAGGCATCAC | TGGCGCTGAA | TAAAATTAAA | TAAGTACCAC | 2820
| TTTGTTCGGG | CGTCCACTGA | AAAGTGAGCG | CCAGAGCCAG | CATACCTTTC | AAGATCCCCG | 2880
| GTTGCCCGCC | ATCAAACCGA | TACAGAGGCG | TAAAAATACC | TGAAATAACA | TAAACAAAGC | 2940
| GGTTTAGACA | GATTACCTTT | ATCATACATT | TTCCGGTGCC | TGTTGCGCTT | TTTCGTCAAG | 3000
| GCCTGCCACA | CTGTTAACCG | CCAGGAAGAC | ATCGGCCACA | TGGTTACCTA | TGACCACCTG | 3060
| AAACTGGCCA | CCGCTTTCCA | CCACCATAAT | AATACCGGGG | GTCTTTTTCA | GTACCTCTGC | 3120
| TTGCGCTTTG | CTTTCATCCT | TTAATTTAAA | AACGTAAATC | GCGTTGCGCA | ATGCATCAGA | 3180
| CTCACAATGT | TATCTGCGCC | CCCGACTCCT | GCGACTATTT | TTCTGGCTAA | CTCCGTCATA | 3240
| ACTTGCCCTC | TACGCTTTGC | GGCAAAACTC | CAAAAAAAA | CCTGAAAAA | ACGGCCTGAC | 3300
| GTGAATCAAG | CAATTTTTTT | CAGGTTTTGC | CCGCTTAGTG | CGGTAACAAT | CCTTTACTCA | 3360
| GTAATAATAT | TTCAGTGTTC | TTTGCGCACG | CGCTCTATAT | TTATGGCTAA | AAACATAATC | 3420
| TCTGCGGGTG | AAATTTTACG | TTGATACTGC | AAACCAATAA | AAATGGCGAT | CCGTTCCGCA | 3480
| CATTGCCATG | CTTGCGGGTA | ATTTGTTTT | ACTGCTTGTT | GTAATGATTC | ATCACTATCG | 3540
| TTAATTGAAG | CATGTTCAAG | AATACGCCAG | GATAAAAACT | TCAGATGTGT | AACCAGTCGC | 3600
| TGATAACTCA | AGCTT | | | | | 3615

( 2 ) INFORMATION FOR SEQ ID NO:18:

( i ) SEQUENCE CHARACTERISTICS:
        ( A ) LENGTH: 4954 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:

( A ) ORGANISM: Escherichia coli
( B ) STRAIN: Clinical Isolate EC-34

( x i ) SEQUENCE DESCRIPTION: SEQ ID NO:18:

| | | | | | |
|---|---|---|---|---|---|
| AAGCTTAACC | GCTCTCATCT | GTTGACCGCA | CGGCATAGCT | ATATTCTGCC | GGTCCTGGGA | 60 |
| CGTAGCGAGA | TTGACATGCA | AAAAAACGGT | GCGCAGGCGG | TAACCGTTGA | GGATTCAATG | 120 |
| TCGATGATTC | ATGCCTCGCG | TGGCGTGTTA | AAACCCGCCG | GTGTAATGCT | GAAATCAGAG | 180 |
| TGTGCAGTGG | TCGCGGGAAT | CGCGCAGGCA | GCACTACCCC | AGAGCGTGGT | AGCCTGGGAG | 240 |
| TATCTGGTGG | AAGATTATGA | TCGCATTCGC | AATGACATTG | AAGCTGTGCT | GCCAGAGTTC | 300 |
| GCCGACTATA | ACCAGCGCAT | CCGTCATCCC | GGTGGTTTTC | ACCTGATAAA | TGCAGCTGCT | 360 |
| GAAAGGCGCT | GGATGACGCC | GTCAGGTAAG | GCTAATTTCA | TTACCAGCAA | AGGGCTGTTA | 420 |
| GAAGATCCCT | CTTCAGCGTT | TAACAGTAAG | CTGGTCATGG | CGACAGTACG | CAGCCACGAT | 480 |
| CAGTACAACA | CGACGATTTA | TGGTATGGAT | GATCGCTATC | GAGGGGTATT | CGGTCAACGA | 540 |
| GATGTGGTCT | TATGAGTGC | TAAACAAGCT | AAAATTTGCC | GTGTAAAAAA | CGGCGAAAGA | 600 |
| GTTAATCTTA | TTGCGCTTAC | GCCAGACGGT | AAGCGCAGTC | ACGCCGCATG | GATAGATTAA | 660 |
| AAGTGGTCAT | TTACCCTATG | GCTGACCGCT | CACTGGTGAC | CTATTTTCCA | GAATCGAATC | 720 |
| ACATGCTAAC | ACTTGATAAC | CACGATCCAT | TAAGTGGCAT | TCCTGGCTAT | AAAAGTATTC | 780 |
| CGCTTGAATT | AGAACCATCA | AATTAATGTC | TCTTCTCATT | TCTTCTGCTG | TCATCCGCAC | 840 |
| AGCAGAAGAA | TTCCTCATTG | ACTATTATTT | CGCAATTTGC | TCACATGGAT | TAAATTAAAC | 900 |
| TACATACTAT | AAGATATAAA | CTTCTGCCTA | CAGCTGTAAG | AAACTCCGCT | CAGTACTGAA | 960 |
| GCACCAGTCC | TATTTCCTCT | TTTCTCCAGC | CTGTTATATT | AAGCATACTG | ATTAACGATT | 1020 |
| TTTAACGTTA | TCCGCTAAAT | AAACATATTT | GAAATGCATG | CGACCACAGT | GAAAAACAAA | 1080 |
| ATCACGCAAA | GAGACAACTA | TAAAGAAATC | ATGTCTGCAA | TTGTGGGTGT | CTTATTACTG | 1140 |
| ACACTTACGT | GATAGCCATT | TTTTCGGCAA | TTGATCAGCT | GAGTATTTCA | GAAATGGGTC | 1200 |
| GCATTGCAAG | AGATCTTACA | CATTTCATTA | TCAATAGTTT | GCAAGGCTGT | AAACAAACAG | 1260 |
| CAAATTATAA | ATATGAAATG | TTAAAAAAGT | ATCGATAAAA | ACTTTATTGT | TTTAAGGAGA | 1320 |
| TAAAATGTCG | CTCGTTTGTT | CTGTTATATT | TATTCATCAT | GCCTTCAACG | CTAACATTTT | 1380 |
| AGATAAAGAT | TACGCCTTCT | CTGACGGCGA | GATCCTGATG | GTAGATAACG | CTGTTCGTAC | 1440 |
| GCATTTTGAA | CCTTATGAGC | GGCATTTTAA | AGAGATCGGA | TTTACTGAAA | ATACCATTAA | 1500 |
| AAAATATCTA | CAATGCACTA | ACATCCAGAC | AGTGACGGTG | CCTGTTCCTG | CGAAGTTTTT | 1560 |
| ACGTGCTTCA | AATGTACCGA | CTGGATTGCT | TAATGAAATG | ATTGCTTATC | TCAACTCGGA | 1620 |
| AGAACGCAAT | CATCATAATT | TTTCAGAACT | TTTGCTTTTT | TCTTGCCTGT | CTATTTTTGC | 1680 |
| CGCATGCAAA | GGTTTCATTA | CACTATTAAC | TAACGGTGTG | CTATCCGTTT | CTGGGAAAGT | 1740 |
| GAGAAATATT | GTCAACATGA | AGCCGGCGCA | CCCATGGAAG | CTGAAAGATA | TTTGTGACTG | 1800 |
| CCTGTACATC | AGTGAAAGCC | TGTTGAAGAA | AAACTTAAGC | AAGAGCAAAC | GACATTCTCA | 1860 |
| CAGATTCTTT | TAGATGCAAG | AATGCAGCAC | GCAAAAAATT | TGATACGCGT | AGAAGGTTCA | 1920 |
| GTCAATAAAA | TTGCCGAACA | ATGTGGTTAT | GCCAGTACAT | CTTATTTTAT | TTATGCGTTC | 1980 |
| CGCAAACATT | TCGGCAACAG | TCCGAAGAGA | GTTTCTAAGG | AGTACCGTTG | TCAAAGTCAC | 2040 |
| ACGGGTATGA | ATACGGGCAA | CACGATGAAT | GCTTTAGCTA | TTTGATTATT | TGCTAACGAG | 2100 |
| TAGTCAACCA | CACACGCTGC | GTAAGAATTA | AATGGGGCAG | CCATTCCCTG | CCCCGCGTTG | 2160 |
| TTTTTAGGCG | ATATATTTAT | TGAAATAAAT | AAGTGACATC | CATCACATAT | TTATGCACTT | 2220 |
| GCATAACCTG | TTGCATGATT | ATTTATGATC | TCAATTCTGC | ATTTGTCAG | TAAAATGCAA | 2280 |

```
TAATTTATTA AATATCAATA AATTAGTTGT TTATCGGCGA GAAATTACTT AATAGAACAG    2340
AAAGTAATGT CAACGCTTTA TGGACTGTTT TTTCCCTTTT TTTAGCTAAA TCTGCTATCT    2400
CTTTATGTGA CTAACTTCAC TTACATCCAC TTATTTCTCT TCGTAAAATT ACTTTGGAAT    2460
TAAGTACAAT AAGAAGAGGA ACATTTATGA AGTCTGCATT AAAGAAAAGT GTCGTAAGTA    2520
CCTCGATATC TTTGATACTG GCATCTGGTA TGGCTGCATT TGCTGCTCAT GCGGCAGATG    2580
ATGTAAAGCT GAAAGCAACC AAAACAAACG TTGCTTTCTC AGACTTTACG CCGACAGAAT    2640
ACAGTACCAA AGGAAAGCCA AATATTATCG TACTGACCAT GGATGATCTT GGTTATGGAC    2700
AACTTCCTTT TGATAAGGGA TCTTTTGACC CAAAAACAAT GGAAAATCGT GAAGTTGTCG    2760
ATACCTACAA AATAGGGATA GATAAAGCCA TTGAAGCTGC ACAAAAATCA ACGCCGACGC    2820
TCCTTTCATT AATGGATGAA GGCGTACGTT TTACTAACGG CTATGTGGCA CACGGTGTTT    2880
CCGGCCCCTC CCGCGCCGCA ATAATGACCG GTCGAGCTCC CGCCCGCTTT GGTGTCTATT    2940
CCAATACCGA TGCTCAGGAT GGTATTCCGC TAACAGAAAC TTTCTTGCCT GAATTATTCC    3000
AGAATCATGG TTATTACACT GCAGCAGTAG GTAAATGGCA CTTGTCAAAA ATCAGTAATG    3060
TGCCGGTACC GGAAGATAAA CAAACGCGTG ACTATCATGA CACCTTCACC ACATTTCTG    3120
CGGAAGAATG GCAACCTCAA AACCGTGGCT TGATTACTT TATGGGATTC CACGCTGCAG    3180
GAACGGCATA TTACAACTCC CCTTCACTGT TCAAAATCG TGAACGTGTC CCCGCAAAAG    3240
GTTATATCAG CGATCAGTTA ACCGATGAGG CAATTGGCGT TGTTGATCGT GCCAAAACAC    3300
TTGACCAGCC TTTTATGCTT TACCTGGCTT ATAATGCTCC GCACCTGCCA ATGATAATC    3360
CTGCACCGGA TCAATATCAG AAGCAATTTA ATACCGGTAG TCAAACAGCA GATAACTACT    3420
ACGCTTCCGT TTATTCTGTT GATCAGGGTG TAAAACGCAT TCTCGAACAA CTGAAGAAAA    3480
ACGGACAGTA TGACAATACA ATTATTCTCT TTACCTCCGA TAATGGTGCG GTTATCGATG    3540
GTCCTCTGCC GCTGAACGGG GCGCAAAAAG GCTATAAGAG TCAGACCTAT CCTGGCGGTA    3600
CTCACACCCC AATGTTTATG TGGTGGAGAA GGAAAACTTC AACCCGGTAA TTATGACAAG    3660
CTGATTTCCG CAATGGATTT CTACCCGACA GCTCTTGATG CAGCCGATAT CAGCATTCCA    3720
AAAGACCTTA AGCTGGATGG CGTTTCCTTG CTGCCCTGGT TGCAAGATAA GAAACAAGGC    3780
GAGCCACATA AAAATCTGAC CTGGATAACC TCTTATTCTC ACTGGTTTGA CGAGGAAAAT    3840
ATTCCATTCT GGGATAATTA CCACAAATTT GTTCGCCATA CAGTCAGACG ATTACCCGCA    3900
TAACCCCAAC ACTGAGGACT TAAGCCAATT CTCTTATACG GTGAGAAATA ACGATTATTC    3960
GCTTGTCTAT ACAGTAGAAA ACAATCAGTT AGGTCTCTAC AAACTGACGG ATCTACAGCA    4020
AAAAGATAAC CTTGCCGCCG CCAATCCGCA GGTCGTTATA GAGATGCAAG GCGTGGTAAG    4080
AGAGTTTATC GACAGCAGCC AGCCACCGCT TAGCGAGGTA AATCAGGAGA GTTTAACAA    4140
TATCAAGAAA GCACTAAGCG AAGCGAAATA ACTAAACCTT CATGCGGCGG ATTTTCCGC    4200
CGCCTTATTG AGCGAGATAG CGATGCACGT TACAGCCAAG CCCTCCAGTT TCAATGTAA    4260
TCTCAAATGT GATTACTGTT TTTACCTTGA AAAAGAGTCG CAGTTACTC ATGAAAAATG    4320
GATGGATGAC AGCACTTTGA AAGAGTTCAT CAAACAATAT ATCGCAGCGT CTGGCAATCA    4380
GGTCTATTTT ACCTGGCAAG GCGGTGAACC CACTCTGGCT GGCCTGGATT TTTTCCGTAA    4440
AGTTATTCAC TATCAACAAC GCTATGCAGG CCAAAAACGT ATTTTAATG CATTACAAAC    4500
GAATGGCATT TTATTGAATA ATGAATGGTG TGCCTTCTCA AAGAACATGA ATTTCTGGTG    4560
GTATCTCGAT CGATGGCCCC CAGGAGTTAC ATGACCGTTA CAGACGCAGT AATTCAGGTA    4620
ACGGTACTTT TGCAAAAGTG ATAGCAGCCA TCGAGCGTCT GAAATCATAT CAAGTAGAGT    4680
```

-continued

| | | | | | |
|---|---|---|---|---|---|
| TTAATACGTT | AACCGTCATT | AATAACGTTA | ATGTCCATTA | CCCTCTTGAG | GTTTATCATT | 4740 |
| TTTTAAAATC | TATCGGCAGT | AAACATATGC | AATTTATCGA | ATTGCTAGAA | ACCGGGACGC | 4800 |
| CGAATATTGA | TTTCAGTGGT | CATAGTGAGA | ACACATTCCG | TATCATTGAT | TTTTCTGTGC | 4860 |
| CTCCCACGGC | TTATGGCAAG | TTTATGTCAA | CCATTTTTAT | GCAATGGGTT | AAAAACGATG | 4920 |
| TGGGTGAAAT | TTTCATCCGT | CAGTTTGAAA | GCTT | | | 4954 |

( 2 ) INFORMATION FOR SEQ ID NO:19:

( i ) SEQUENCE CHARACTERISTICS:
        ( A ) LENGTH: 3796 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Escherichia coli
        ( B ) STRAIN: Clinical Isolate EC- 39

( x i ) SEQUENCE DESCRIPTION: SEQ ID NO:19:

| | | | | | |
|---|---|---|---|---|---|
| AAGCTTAATC | GCGTGAATCA | GGAGTAAAAA | AATGACAACC | CAGACTGTCT | CTGGTCGCCG | 60 |
| TTATTTCACG | AAAGCGTGGC | TGATGGAGCA | GAAATCGCTT | ATCGCTCTGC | TGGTGCTGAT | 120 |
| CGCGATTGTC | TCGACGTTAA | GCCCGAACTT | TTTCACCATC | AATAACTTAT | TCAATATTCT | 180 |
| CCAGCAAACC | TCAGTGAACG | CCATTATGGC | GGTCGGGATG | ACGCTGGTGA | TCCTGACGTC | 240 |
| GGGCATCGAC | TTATCGGTAG | GTTCTCTGTT | GGCGCTGACC | GGCGCAGTTG | CTGCATCTAT | 300 |
| CGTCGGCATT | GAAGTCAATG | CGCTGGTGGC | TGTCGCTGCT | GCTCTCGCGT | TAGGTGCGCA | 360 |
| ATTGGTGCGG | TAACCGGGGT | GATTGTAGCG | AAAGGTCGCG | TCCAGGCGTT | TATCGCTACG | 420 |
| CTGGTTATGA | TGCTTTTACT | GCGCGGCGTG | ACCATGGTTT | ATACCAACGG | TAGCCCAGTG | 480 |
| AATACCGGCT | TTACTGAGAA | CGCCGATCTG | TTTGGCTGGT | TGGTATTGG | TCGTCCGCTG | 540 |
| GGCGTACCGA | CGCCAGTCTG | GATCATGGGG | ATTGTCTTCC | TCGCGGCCTG | GTACATGCTG | 600 |
| CATCACACGC | GTCTGGGGCG | TTACATCTAC | GCGCTGGGCG | ACAACGAAGC | GACAACGCGT | 660 |
| CTTTCTGGTA | TCAACGTCAA | TAAAATCAAA | ATCATCGTCT | ATTCTCTTTG | TGGTCTGCTG | 720 |
| GCATCGCTGG | CGGGATCATA | GAAGTGGCGC | GTCTCTCCTC | CGCACAACCA | CGGCGGGGAC | 780 |
| TGGCTATGAG | CTGGATGCTA | TTGCTGCGGT | GGTTCTGGGC | GGTACGAGTC | TGGCGGGCGG | 840 |
| AAAAGGTCGC | ATTGTTGGGA | CGTTGATCGG | CGCATTAATT | CTTGGCTTCC | TTAATAATGG | 900 |
| ATTGAATTTG | TTAGGTGTTT | CCTCCTATTA | CCAGATGATC | GTCAAAGCGG | TGGTGATTTT | 960 |
| GCTGGCGGTG | CTGGTAGACA | ACAAAAAGCA | GTAATAACGA | CTACAGGCAC | ATCTTGAATA | 1020 |
| TGAACATGAA | AAAACTGGCT | ACCCTGGTTT | CCGCTGTTGC | GCTAAGCGCC | ACCGTCAGTG | 1080 |
| CGAATGCGAT | GGCAAAGAC | ACCATCGCGC | TGGTGGTCTC | CACGCTTAAC | AACCCGTTCT | 1140 |
| TTGTATCGCT | GAAAGATGGC | GCGCAGAAAG | AGGCGGATAA | ACTTGGCTAT | AACCTGGTGC | 1200 |
| TGGACTCCCA | GAACAACCCG | GCGAAAGAGC | TGGCGAACGT | GCAGGACTTA | ACCGTTCGCG | 1260 |
| GCACAAAAAT | TCTGCTGATT | AACCCGACCG | ACTCCGACGC | AGTGGGTAAT | GCTGTGAAGA | 1320 |
| TGGCTAACCA | GGCGAACATC | CCGGTTATCA | CTCTTGACCG | CCAGGCAACG | AAAGGTGAAG | 1380 |
| TGGTGAGCCA | CATTGCTTCT | GATAACGTAC | TGGGCGGCAA | AATCGCTGGT | GATTACATCG | 1440 |
| CGAAGAAAGC | GGGTGAAGGT | GCCAAAGTTA | TCGAGCTGCA | AGGCATTGCT | GGTACATCCG | 1500 |
| CAGCCCGTGA | ACGTGGCGAA | GGCTTCCAGC | AGGCCGTTGC | TGCTCACAAG | TTTAATGTTC | 1560 |

```
TTGCCAGCCA GCCAGCAGAT TTTGATCGCA TTAAAGGTTT GAACGTAATG CAGAACCTGT    1620
TGACCGCTCA TCCGGATGTT CAGGCTGTAT TCGCGCAGAA TGATGAAATG GCGCTGGGCG    1680
CGCTGCGCGC ACTGCAAACT GCCGGTAAAT CGGATGTGAT GGTCGTCGGA TTTGACGGTA    1740
CACCGGATGG CGAAAAAGCG GTGAATGATG GCAAACTAGC AGCGACTATC GCTCAGCTAC    1800
CCGATCAGAT TGGCGCGAAA GGCGTCGAAA CCGCAGATAA AGTGCTGAAA GGCGAGAAAG    1860
TTCAGGCTAA GTATCCGGTT GATCTGAAAC TGGTTGTTAA GCAGTAGTTT TAATCAGGTT    1920
GTATGACCTG ATGGTGACAT AAATACGTCA TCGACAGATG AACGTGTAAT ATAAAGAAAA    1980
GCAGGGCACG CGCCACCCTA ACACGGTGGC GCATTTTATG GACATCCCGA ATATGCAAAA    2040
CGCAGGCAGC CTCGTTGTTC TTGGCAGCAT TAATGCTGAC CACATTCTTA ATCTTCAATC    2100
TTTTCCTACT CCAGGCGAAA CGTAACCGGT AACCACTATC AGGTTGCATT TGGCGGCAAA    2160
GGCGCGAATC AGGCTGTGGC TGCTGGGCGT AGCGGTGCGA ATATCGCGTT TATTGCCTGT    2220
ACGGGTGATG ACAGCATTGG TGAGAGCGTT CGCCAGCAGC TCGCCACTGA TAACATTGAT    2280
ATTACTCCGG TCAGCGTGAT CAAAGGCGAA TCAACAGGTG TGGCGCTGAT TTTTGTTAAT    2340
GGCGAAGGTG AGAATGTCAT CGGTATTCAT GCCGGCGCTA ATGCTGCCCT TCCCCGGCG    2400
CTGGTGGAAG CGCAACGTGA GCGTATTGCC AACGCGTCAG CATTATTAAT GCAGCTGGAA    2460
TCACCACTCG AAAGTGTGAT GGCAGCGGCG AAAATCGCCC ATCAAAATAA AAACTATCGT    2520
TCGCTTAACC CGCTCCGGCT CGCGAACTTC CTGACGAACT CTGCGCTGTG GACATTATTA    2580
CGCCAAACGA AACGGAAGCA GAAAAGCTCA CCGGTATTCG TGTTGAAAAT GATGAAGATG    2640
CAGCGAAGGC GGCGCAGGTA CTTCATGAAA AAGGTATCCG TACTGTACTG ATTACTTTAG    2700
GAAGTCGTGG TGTATGGGCT AGCGTGAATG GTGAAGGTCA GCGCGTTCCT GGATTCCGGG    2760
TGCAGGCTGT CGATACCATT GCTGCCGGAG ATACCTTTAA CGGTGCGTTA ATCACGGCAT    2820
TGCTGGAAGA AAAACCATTG CCAGAGGCGA TTCGTTTTGC CCATGCTGCC GCTGCGATTG    2880
CCGTAACACG TAAAGGCGCA CAACCTTCCG TACCGTGGCG TGAAGAGATC GACGCATTTT    2940
TAGACAGGCA GAGGTGACGC TTGGCTACAA TGAAAGATGT TGCCCGCCTG GCGGGCGTTT    3000
CTACCTCAAC AGTTTCTCAC GTTATCAATA AAGATCGCTT CGTCAGTGAA GCGATTACCG    3060
CAAAGTGAGC GCGATTAAAG ACTCAATTAC GCGCCATCAG CTCTGGCGCG TAGCCTCAAA    3120
CTCAATCAAA CACATACCAT TGGCATGTTG ATCACTGCCA GTACCAATCC TTTCTATTCA    3180
GAACTGGTGC GTGTCGTTGA ACGCAGCTGC TTCGAACGCG GTTATAGTCT CGTCCTTTGC    3240
AATACCGAAG GCGATGAACA GCGGATGAAT CGCAATCTGG AAACGCTGAT GCAAAAACGC    3300
GTTGATGGCT TGCTGTTACT GTGCACCGAA ACGCATCAAC CTTCGCGTGA AATCATGCAA    3360
CGTTATCCGA CAGTGCCTAC TGTGATGATG GACTGGGCTC CGTTCGATGG CGACAGCGAT    3420
CTTATTCAGG ATAACTCGTT GCTGGGCGGA GACTTAGCAA CGCAATATCT GATCGATAAA    3480
GGTCATACCC GTATCGCCTG TATTACCGGC CCGCTGGATA AAACTCCGGC GCGCTGCGGT    3540
TGGAAGGTTA TCGGGCGGCG ATGAAACGTG CGGGTCTCAA CATTCCTGAT GGCTATGAAG    3600
TCACTGGTGA TTTTGAATTT AACGGCGGGT TTGACGCTAT GCGCCAACTG CTATCACATC    3660
CGCTGCGTCC TCAGGCCGTC TTTACCGGAA ATGACGCTAT GGCTGTTGGC GTTACCAGG    3720
CGTTATATCA GGCAGAGTTA CAGGTTCCGC AGGATATCGC GGTGATTGGC TATGACGATA    3780
TCGAACTGGC AAGCTT                                                   3796
```

( 2 ) INFORMATION FOR SEQ ID NO:20:

( i ) SEQUENCE CHARACTERISTICS:

( A ) LENGTH: 5541 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Escherichia coli
( B ) STRAIN: Clinical Isolate EC- 625

( x i ) SEQUENCE DESCRIPTION: SEQ ID NO:20:

| | | | | | | |
|---|---|---|---|---|---|---|
| AAGCTTAAGC | CTGCATTTGC | TCAATGAAGC | GCAGAATGAG | CTGGAACTGT | CAGAAGGCAG | 60 |
| CGACGATAAC | GAAGGTATTA | AAGAACGTAC | CAGCTTCCGT | CTGGAGCGTC | GGGTCGCCGG | 120 |
| AGTGGGTCGT | CAAATGGGCC | GCGGTAACGG | CTATCTGGCA | ACCATCGGCG | CGATTTCTCC | 180 |
| GTTCGTTGGT | CTGTTTGGTA | CGGTCTGGGG | CATCATGAAC | AGCTTTATTG | GTATCGCGCA | 240 |
| AACGCAGACC | ACTAACCTGG | CAGTCGTTGC | GCCGGGTATC | GCAGAAGCTC | TGTTAGCAAC | 300 |
| GGCAATCGGC | CTCGTGGCAG | CGATTCCTGC | GGTCGTTATC | TATAACGTAT | TGCACGCCA | 360 |
| GATTGGCGGC | TTTAAAGCGA | TGCTGGGTGA | TGTTGCAGCG | CAGGTATTGT | TGCTGCAAAG | 420 |
| CCGTGACCTG | GATCTGGAAG | CCAGCGCCGC | TGCGCATCCG | GTTCGTGTCG | CACAAAAATT | 480 |
| ACGCGCAGGA | TAATATCCGA | TGGCAATGCA | TCTTAACGAA | AACCTCGACG | ATAACGGCGA | 540 |
| AATGCATGAT | ATCAACGTGA | CGGCGTTTAT | CGACGTGATG | TTGGTTCTGC | TGATTATCTT | 600 |
| TATGGTGGCG | GCACCGTTAG | CGACGGTAGA | TGTGAAGGTG | AACTTGCCTG | CTTCTACCAG | 660 |
| CACGCCGCAG | CCGCGGCCGG | AAAAACCGGT | TTATCTGTCG | GTGAAGGCAG | ACAACTCGAT | 720 |
| GTTTATCGGT | AACGATCCGG | TCACCGATGA | AACAATGATT | ACGGCGTTGA | ATGCGTTAAC | 780 |
| CGAAGGCAAG | AAAGACACCA | CCATCTTCTT | CCGAGCGGAT | AAAACCGTCG | ATTACGAGAC | 840 |
| GTTGATGAAG | GTAATGGATA | CGCTGCATCA | GGCGGGTTAC | CTGAAGATAG | GTCTGGTCGG | 900 |
| CGAAGAAACC | GCCAAAGCGA | AGTAAAGTAG | AATTGCCTGA | TGCGCTACGC | TCATCAGGCC | 960 |
| TACAAAATCT | ATTGCAACAT | GTTGAATCTT | CGTGCGTTTG | TAGGCCGGAT | AAGGCGTTCA | 1020 |
| CGCGCATCCG | GCATTAGGTG | CTCAATGCCT | GATGCGCTAC | GTTTATCAGG | CCTACAAAAT | 1080 |
| CTATTGCAAC | ATGTTGAATC | TTCATGCGTT | TGTAGGCGGA | TAAGGCGTTT | CGCACATCA | 1140 |
| GGTAAGAGTG | AATTCACAAT | GATGCCCGGT | TGCTTTTCAC | AACCGGGCAT | TTTTTAACC | 1200 |
| TAAATGCTCG | CCGCCGCACA | CACCGTGCAC | TTCTGCGGTG | ACGTAGCTCG | ACTCCTGACT | 1260 |
| TGCCAGATAA | ACATATACTG | GGGCCAGTTC | CGCCGGTTGC | CCCGCACGCT | TCATCGGCGT | 1320 |
| TTTCTGACCA | AACTGCGGGA | TCTTATCCTG | CGTTTGTCCG | CCGGAAATTT | GCAGTGCCGT | 1380 |
| CCAGATAGGG | CCTGGCGCGA | CAATATTCAC | CCGAATACCT | TTCTCCGCGA | CCTGTTTTGC | 1440 |
| CAGGCCACGG | CTGTAGTTCA | GAATCGCCGC | CTTCGTAGCC | GCATAGTCCA | GTAAATGCGG | 1500 |
| ACTTGGCTGG | TATGCCTGGA | TTGACGAAGT | GGTGATAATA | CTTGCACCTT | TCGGTAGCAG | 1560 |
| GGGATCGCT | TCCTGGGTTA | GCCAGAACAG | CGCGAAAACG | TTAATGGCAA | AGGTCTTTTG | 1620 |
| AAACTGTTCG | CTGGTGAGGT | CTGCAATATC | AGGAATGGCA | ACCTGTTTCC | CGGCGACCAG | 1680 |
| CGCCATAATA | TCCAGCCCGC | CTAACGCCTT | GTGCGCTTCG | TGAACCAGCG | AACGGGCGAA | 1740 |
| TTTCTCATCG | CTTAAATCGC | CTGGCAGCAG | AACGGCTTTG | CGTCCGCATT | CTTCAATGAT | 1800 |
| CTTTTTCACA | TCCTGAGCGT | CTTCTTCTTC | CACGGGAAGA | TAACTGATCG | CCACGTCAGC | 1860 |
| CCCTTCACAC | GCGTAAGATG | GCGGCAGCGC | GACCGATTCC | GGAATCGCCC | CCTGTCACCA | 1920 |
| GTGCTTTACG | ATCTTTCAGG | CGACCGCTAC | CAACATAGGT | TTTCTCGCCG | CAATCCGGTA | 1980 |
| CCGGTGTCAT | CTTCGCCTGG | ATGCCTGGCG | TCGGTTGTTT | CTGTTTGGGA | TATTCACCAG | 2040 |

```
TGTAATACTG CGTGGTCGGG TCTTTTAAAT GAGACATCGT TTTTCTCCCT TCAGGTTCAA    2100
CGTCCTTTAA GGGTAGACGC TCTCGATGCG TTGATAAGGG AACCAGGAAG ATCCCTAACC    2160
CTCAGAATTA TGCGACAAAG GTTAACGGA TATGTTGATT TGCTGTTGCG CGCTGTTTAC    2220
TCAATTGCGA TATACTGTTG CCCGTTTTAA CTACACGACA GGAATGTATG AACGTTTTC    2280
TTGAAAATGC AATGTATGCT TCTCGCTGGC TGCTTGCCCC CGTGTACTTT GGCCTTTCGC    2340
TGGCGTTAGT TGCCCTGGCG CTGAAGTTCT TCCAGGAGAT TATTCACGTA CTGCCGAATA    2400
TCTTCTCGAT GGCGGAATCA GATTGATCC TCGTGTTGCT GTCGCTGGTG GATATGACAC    2460
TGGTTGGCGG TTTACTGGTG ATGGTGATGT TTTCCGGTTA TGAGAATTTC GTCTCGCAGC    2520
TGGATATCTC CGAGAACAAA GAGAAGCTGA ACTGGCTGGG GAAAATGGAC GCAACGTCGC    2580
TGAAAAACAA AGTAGCAGCG TCGATTGTGG CAATTCTTC CATTCACTTA CTGCGCGTCT    2640
TTATGGATGC GAAAAATGTC CCTGATAACA AACTGATGTG GTACGTCATT ATCCATCTGA    2700
CGTTTGTGCT CTCTGCATTT GTGATGGGCT ATCTTGACCG ACTGACTCGT CATAATCACT    2760
GATCTTATGC GGGCGCGGTT CTCGCGCCCG TTATTAACAG GTCATTTATC GGAAGACGCC    2820
TGCCACAGAT TCAGCTCGCC ATCGGCGATA TGCTGATCAA TCTGCGCCAG CTCCTCGGTG    2880
CTAAATGTCA GATTATTCAG CGCCTGCACG TTCTCCTCAA GTTGTCCGCG CGGCTGGCAC    2940
CAATCAATAC CGACGTCACG CGATCATCTT TCAGCAACCA GCTTAACGCC ATTGCGCCA    3000
TTGATTGTCC ACGCTGCTGT GCCATTTCAT TCAATAAGTG TAGGCTGTTG AGGTTGGCTT    3060
CGGTAAGCAT TTTCGGCGTC AGACCACGAA CTTTATTCCC TTCACGATGC ATCCGTGAAT    3120
CTTGCGGAAT GCCGTTGAGA TATTTTCCGG TCAGCAATCC CTGAGCCAGA GGAGTAAAGG    3180
CAATACAGCC CACGCCGTTA TTTTGCAGGG TATCCAGCAG GCCGCTTTTA TCCACCCAGC    3240
GGTTCAGTAA ATTGTACGAA GGTTGATGAA TTAACAGCGG AATTTTCCAC TCGCGCAGCA    3300
ACTCAACCAT TTTTTGCGTC CGCTCTGGCG AGTAAGAGGA GATCCCGACA TAAAGCGCCT    3360
TACCGCTTTG TACCGCATGA GCCAGCGCAG AGGCGGTTTC TTCCATCGGC GTATTTTCAT    3420
CGACGCGATG AGAGTAAAAG ATATCGACAT ACTCAAGCCC CATACGCTTC AGGCTTTGGT    3480
CGAGGCTGGA GAGCAGGTAT TTACGTGAAC CGCCAGAGCC GTAAGGGCCG GGCCACATAT    3540
CGTAGCCAGC CTTGGTAGAG ATAATCAGTT CATCGCGATA AGCGGCAAAA TCCTCCCGCA    3600
GCAGGCGACC AAAGTTCTCT TCTGCGCTTC CTGGAGGCGG CCCGTAATTG TTGGCTAAAT    3660
CAAAGTGCGT AATGCCTAAA TCAAACGCTT TACGCAGGAT TGCACGCTGT GATTCCAGCG    3720
CGTTAACGTG ACCGAAATTG TGCCATAAAC CGAGCGATAA CGCGGGCAGG CGTAAACCAC    3780
TTTTTCCGCA ATAGCGGTAC TGCATCTGCC CGTAACGTTC GGGTTCGCTA ACCAGACCAT    3840
GACCTCTCCT TTCCACCGTT CAATTTCGAA ACAATGTTTC TAGTTTAGCG ATTCGCCAGC    3900
GCGTATCCCG TAGTCTGGCT CACAGAGTGA CGAAAAATTG GCAAAACAC GCGCTTATGC    3960
TTTGCTTAAA AAAACACCAG TTGAGGAGTG CAACGATGCC GCGTTAACC GCCAAAGATT    4020
TCCCACAAGA GTTGTTGGAT TACTACGACT ATTACGCTCA CGGGAAAATC TCGAAACGTG    4080
AGTTCCTCAA TCTTGCGGCG AAGTATGCGG TGGGCGGGAT GACGGCATTA GCGTTGTTTG    4140
ATTTGCTCAA GCCAAATTAT GCGCTGGCGA CTCAGGTAGA GTTACCGAC CTGGAGATTG    4200
TTGCTGAGTA CATCACGTAT CCTTCGCCAA ATGGTCACGG CGAGGTACGG GGTTATCTGG    4260
TGAAACCCGC AAAAATGAGC GGCAAAACGC CAACCGTGGT GGTGGTGCAT GAGAATCGTG    4320
GACTGAATCC GTATATCGAA GATGTGGCAC GGCGAGTGGC GAAGGCGGGG TATATCGCCC    4380
TGGCACCTGA CGGCTTAAGT TCCGTTGGAG GTTATCCGGG AAATGATGAT AAAGGTCGTG    4440
```

-continued

```
AGCTGCAACA GACAGGTTGA TCCAACCAAA CTGATGAATG ATTTCTTTGC CGCAATTGAG    4500
TTTATGCAAC GCTATCCGCA AGCGACAGGC AAAGTGGGTA TTACCGGATT TTGCTATGGC    4560
GGTGGCGTAT CGAACGCGGC GGCTGTCGCG TATCCGGAAC TGGCCTGCGC GGTGCCGTTT    4620
TATGGTCGTC AGGCACCCAC TGCCGATGTG GCGAAGATTG AAGCGCCTTT ACTACTCCAC    4680
TTCGCGGAAC TGGACACCCG AATCAACGAG GGCTGGCCTG CTTACGAGGC GGCGTTGAAA    4740
GCCAATAATA AGGTTTATGA GGCGTATATC TATCCGGGGG TTAATCACGG ATTCCATAAT    4800
GATTCCACGC CCCGTTATGA CAAATCTGCC GCCGATCTTT CCTGGCAAAG GACACTGAAA    4860
TGGTTCGATA AATATCTCTC CTGATAGGTT TATCTCTTAC GGGATTACGT CTTAAACAAG    4920
CATGAAAAAA TAGCGTGCGC AAAAGTCGTT CTTTGCCTAA AATATCGCTA TATATAACAA    4980
TATATAGCGA ATGAGGTGAA CGATGAATAA CCATTTGGT AAAGGCTTAA TGGCGGGATT     5040
AAAAGCAACG CATGCCGACA GTGCGGTTAA TGTGACAAAA TACTGTGCCG ATTATAAACG    5100
CGGTTTTGTA TTAGGCTACT CACACCGGAT GTACGAAAAG ACCGGAGATC GCCAGCTTAG    5160
CGCCTGGGAA GCGGGTATTC TGACGCGCCG CTATGGACTG GATAAGAGA TGGTAATGGA     5220
TTTCTTTCGT GAGAATAATT CCTGTTCTAC GTTGCGCTTT TTTATGGCCG GTTATCGCCT    5280
CGAAAATTGA TCAAACATAC GTATTATCTT GCTTTAATTA ATTACACTAA TGCTTCTTCC    5340
CTTCGTTTTA GCGCCCCGCC GCAGTATCAT GATATCGATA ACCATAATAA ATGTGTGGTA    5400
AATGGCGCAT CGATCGCATT ATTGATTTTG CGATTGAGGC AAAATATATG CCAGGTCTTC    5460
GCAACGGAAT AACTATAAAT GACTGGAGAT AACACCCTCA TCCATTCTCA CGGCATTAAC    5520
CGTCGTGATT TCATGAAGCT T                                              5541
```

( 2 ) INFORMATION FOR SEQ ID NO:21:

( i ) SEQUENCE CHARACTERISTICS:
        ( A ) LENGTH: 6317 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterobacter cloacae
        ( B ) STRAIN: Clinical Isolate ET- 12

( x i ) SEQUENCE DESCRIPTION: SEQ ID NO:21:

```
AAGCTTGCCC GCATCATTCA GGAGCAGGGG CGTCGCGACC AGTTAGGTGT GAAGTTTGGC      60
AGCGGTGACA GCCCGGACTG CCGGGGGATC ACGGTTCCGG AACTGCAGAG TATCGACTTC     120
GACAAAATCA ACTTCTCTGA CTTCTACGAG GATTTGATGA AGAACCAGAA AATCCCCGAT     180
ACCAGCGCGC AGGTCAAGCA GATTAAGGAT CGCATCGCCG CGCAGGTGAA CCAGCAGGGA     240
GGTGGCAAAT GAAGCGTGTC CTCTGTGGCC TGCTTATGGC GCTGGCGAGC CATACGGCAC     300
TGGCCGATGA GATTGTGACG CCGGCTGAGC CGTTCACCGG CTGGTCCTGG TACAACGAAC     360
CGAAAAAGCC CCCTGAGCAG CCCCGGAAAC CGCAGCAGCC AGCACCGCAG CCATTCCGGA     420
TCTCAGCAAA ATGTCCCCGA TGGAGCAGGC CAGGGTGCTG AAAGGGTATA CACAGGAGGC     480
GCTTAACCGC GCCATCCTGT ACCCCTCAAG GGAAACACG GCGACGTTCC TGCGCTGGCA      540
GAAGTTCTGG ACGGACCGGG CATCGATGTT CAGCCAGTCC TTTGCGGCGG CGCAGCTGAG     600
CCATCCGGAC CTCGACTACA ACCTGGAGTA CCGCACTAC AACAGCATGG CGCCGTTTAT      660
GCAGACCCGT GACCAGCAGA CGCGGCAGAG CGCCGTGGAG CAGCTTGCGC AGAGTACGGT     720
```

```
CTGTTCTACT TCTACCGGGG CAGTGACCCG ATTGATGTGC AGATGGCGGG CGTGGTGGCT   780
GACTTTGCGA AAACCAACGG GATCTCACTC ATTCCGGTCT CGGTTGACGG ACAGGTGGCG   840
GCCACCCTGC CGCAAAGCCG TCCGGACACC GGACAGTCCC GGTCGATGAA TATCACGCAC   900
TTTCCGGCGC TCTTCCTGGT TGACCCGCGC AACCAGAACT ACCGTGCCCT GTCCTATGGC   960
TTCATGACCC AGGATGACCT GTCAAAACGA TTCCTGAACG TGGCCACCGG CTTTAAACCC  1020
AATTCCTGAG AGCCTTTTAT GACAAAAACA CTGTTTACCT CATCCGCGAT GCAGGGCGGG  1080
CTGCCCTGTA TTCCTTCGTC CTCGGCCCGG CACTGGTGCT GTATGTGTTT GTGATGCTGG  1140
CGGCATCAGA CGGCTCACTT TCCCGGCAAT TCCTGACGAC CTTTCATCAC CTGACTGAGG  1200
GTGCGCCTGC CGGCAAGGTG ATGGGATGTG TTAATGAACA TGAGATGGCA GGGCGTTTCT  1260
CGCCACCTGA ACCCGGAGAG TCGTTAAAGC CCGTGCCTTC CGTTTTAGAT AAAGCACCGC  1320
CTGAAGTGTT ATGTCAGCTC GGGCCCGTTG ACAGCGATTC GTGGGCGCGT ACGACAGATG  1380
CAACGTTGCT CAACACCTGG ATTATCTCGG TGATGTTTGG CTTTGGTGTG TGGTTTGTTT  1440
TATATGGCCT GTCCCGGGCC GCTCAGCGTC GCATTTCACC AGACACACAT TCTGTACTGG  1500
TACGGCAGAA CAAGGAGACA CAGGAATGAA ACCAACTCTT CTCGCAGGAC TGATTTTCTG  1560
GGGCATGATG GCGCGCCGTA CTGAGCGAGC TGATGACCTG GTCCGTGGAG CATACACAGC  1620
AGGGCCTGCT GTGGCTGTGC AATGGGATGT GGGCCGGGGC GGCTGGCATG GTGATTTATG  1680
CAGGTTATCG CTGGTACCGT GACGAAAGAG GGCAAACGCA TAAGGAAGGC GATCATGAAC  1740
ATTAAAACCG GACTCACGGC TCTGCTGATG TGCCTGCCCC TGCTGGCGAA CGCGGGGGCG  1800
CGCGAGGAGT TAATGGCGCT TGAAGCGACA AAAACAACCT CTGCTGACGC TGCAGCCATC  1860
ACCGCCTCCA CCATTCCGGT ACCTGCGCCG GCCAGCCTGA TGGCGCTGCC GGACGGACGT  1920
CGGGCTAACA TGAAAGATTA TGCCGTGGTG CTTTTTATGC AGGCACACTG CCAGTACAGC  1980
GCGAAGTTTG ACCCGCTGCT GAAGGGCTGG GCTGATGAGC ATTCTGTCAG GGTTTATCCA  2040
TACACCCTGG ACGGCGGCGG TGATGTGTCT TACCGACGCC GATGATCCCG CGCAAGACGG  2100
ACCCGAATTC TCCCATTGCA GACGAGATTG TCACCTTCTT CGGAAACGGG CTGCCGATTG  2160
CGACACCAAC GGCCTTTATG GTCAACGTTA ACACCCTGAA AGCCTACCCG CTGACCCAGG  2220
GTGTGATGGA CATCCCCGCT CTTGAGAGCC GTATGGCCAG CCTGATTCAG GCTGACATGG  2280
ACAACGTCGA TCCGAAAACG CTGCCGCCCA TGCCGGCAAG TGCGCAGGTC ACCCCTCAGT  2340
AATACAAACG GACTACAAAA TGACGACAAA TACGTATGCG TTATCGCGTA CCGAGCGCGT  2400
GTGGCTGTTA TTCAGCGTGA CGCTGCTTGT GTCCGCAGCT TTCTATGGGG TACTGGCCCA  2460
CCGGGTGGTC AGCGTCTGAC CGTCAGACTG ACAACTGTTT GCAGGACTTT CCGGTGCTCC  2520
TGCTTATCTC GCTGAGTATC GGATTCTTTT TCACCGTCAC CGGGCTGTAC GTCTGCCGGC  2580
AGACCCTGGT CAGGAAACCC CGGGAGGAGA TTGCATGAGG CACATCAGAC TGAAGACGTT  2640
TATCCGAAAC CAGGCTATCG GGATACTGAA AGACAGTAGT GAGGATACGG AAACCCGAAA  2700
ATGGACGGAT TTGTTAACCC TGAAACTGTT TTTATGCCTT AATTTTTACC GCCGTAGTCG  2760
AAAGGGTATA CGTGAAGTGC GCCATCACAA CGCTCAGTGC GATCTCCGTT GACCGCTCCG  2820
AACAGTTTAC GCTCTCGCTT CTCATCCACT ATCCACAGTA CCTGTTGTGG GGCGTTATGG  2880
CCGCGATTAT CGCGCTCATT GCGGTGAATT TACTCGTCTG CGGCTGGTTC TGTCTGGCCA  2940
CATATCTTTG CCGCAAACTG AACCGGACTG ACATCCCGGC AGGCAAGGAT ATGCAAGCTG  3000
TGGAGGTGCC TAATGATTAA GGCGCTTATT ACGGCAGGGG TTGTGTTCTT CTCAGGTCTG  3060
GCAGCGCTGC CTGCTCAGGC GGACGTCAAT GGTGACTCAA CGGCTTCTTT GGCAAGCTGG  3120
```

```
GCTACAGCGG CAACGTCTCT CAGGCGCAGG CCTGGCAGGG GCAGGCGGCC GGGTATTTCT    3180
CCGGCGGGTC GGTCTACCTG CGAAACCCCG TCAAAAACGT TCAGCTGATC TCGATGCAGC    3240
TGCCGTCCCT GAACGCCGGC TGCGGCGGTA TCGATGCCTA CCTGGGGTCA TTCAGCATGA    3300
TCAGCGGTGA GGAAATTCAG CGATTCGTGA AGCAAATCAT GAGTAACGCG GCTGGCTATG    3360
CATTCGACCT GGCACTGCAG ACGATGGTCC CGGAGCTGAA GCAGGCGAAA GATTTCCTGC    3420
AGAAGCTGGC CAGTGATGTT AACTCCATGA ACATGAGTTC GTGCCAGGCC GCTCAGGGCA    3480
TCATAGGCGG GTTGTGGCCC GTAACGCAGG TGTCACAGCA GAAAATCTGC CAGGACATTG    3540
CCGGCGAAAC CAACATGTTT GCTGACTGGG CGGCCTCCCG CCAGGGCTGC ACCGTCGGAG    3600
GACAGGGGGA TAAAGTCACG GCCAAAGCCG GCGACGCAGA AAAAGACCCC AGGTACTGAA    3660
AAACAAAAAC CTTATCTGGG ACACGCTCAG TAAGAACGGG CTGCTTGGTA CGATCGCGC    3720
CCTGAAGGAG CTGGTCATGA GTACTGTCGG CTCCATCATT TTCAACAAAA CCGGAGACGT    3780
GACATCCTGA CGCCGCTGGT CGATACCGCG ACCTGATTAA AGTTCTGATG CGCGGGGGAA    3840
CAGCGAAGGT CTACGGGTGC GATGAGGCAA CACTCTGTCT GGGGCCTGTC GTTACTAACC    3900
TGACGATTAC TGAGTCCAAC GCTCTGGTCA CACTGGTCAA AAAACTGATG CTCTCGATGC    3960
AGAACAAACT TGTCGATGAC AAACCGCTGA CCGATCAGGA AAAAGGCTTC GTGAACACCA    4020
CCTCTGTGCC GGTACTGAAA TACCTGACCA ACGCCCAGAG TATGGGGATG AGCGCCACGT    4080
ACCTCCTGCA GGTTCCGAC TTCATCGCGC AGGACCTGAT GATCCAGTAC CTCCAGGAAC    4140
TGGTGAAACA GGCAAGCCTG TCTCTGGCTG GTAAGAACTT CCCGGAAGAG GCCGCTGCGA    4200
AGTGCGCGAC AACATCATTC ATGCCCAGGG ACTGCTGGCC GACATGAAGC TGCAGTCTGC    4260
GGCAGACCAG AACGCACTGG ACGGCATCGA CCGCAACATG CAGTACTGCA GCAGCAGGTG    4320
TCCACCATTG TTTCAGGCTC CTATCAAAGC AACTATCACT GGGGTGATCG CTGATGCTTG    4380
AGATATACAC CATTTATGGC GGGGGAATGT GGAAAAACGC GCTGGACGCC GTTGTCACCC    4440
TTGTCGGTCA GAATACCTTC CACACCTTAA TGCGTATTCG CCCGGCACCT TCGGGGTGCT    4500
GGCTGTATTG CTCACTTTCA TCAAACAACG TAACCCGATG GTCTTCGTCC AGTGGCTGGC    4560
GATCTTCATG ATCCTGACGA CCATCCTGCT GGTACCGAAA CGTTCAGTAC AGATAATTGA    4620
CCTCTCAGAC CCCGGCTGCG GTGTGGAAAA CCGATAATGT ACCGGTCGGT CTGGCTGCCA    4680
TCGCGTCACT GACGACCAGC ATCGGTTACA AAATGGCATC GGTGTACGAC ATGCTGATGG    4740
CCAGACCTGA CTCGGTAACC TACAGCAAGA CCGGTATGCT GTTTGGCTCG CAGATTGTGG    4800
CGGAAACCAG TGACTTCACC ACGCAAAACC CGGAACTGGC TCAGATGCTG CCGGACTACG    4860
TGGAAAACTG TGTGATCGGC GACATTCTGC TGAACGGTAA ATACACCATC AATCAGCTGC    4920
TCAATTCCAC TGACCCGCTG ACGTTGATAA CCAGTAACCC AAGCCCGCTG CGGGGCATCT    4980
TTAAGATGAC CTCCACCTCG CGCCAGTTCC TGACCTGTCA GCAGGCGGCA ACGGAGATTA    5040
AGACGCTGGC GAATACCGAC GTCAATCCGG GCAGTGCGAC GTTCACCTGG CTGACGCGGA    5100
AGGTATTCGG CAACAAGCTG AATGGTGCCT CGCTTCTGCC AACGCTATGG GTGAGAGCTA    5160
CGGATTCTTC TATGCCGGGG GAATGACGGC TGCGCAGATC ATGAAGAACA ACATCACGAA    5220
CAGTGCAGTT CGGCAGGGGA TTAAGGGTTT CGCCGCTCGC TCATCCGACA CGGCTAACCT    5280
GCTGAACCTG GCCACCGAGA ACGCTGCAAC CAAACAGCGT CTCAGCTGGG CTGCGGGTAA    5340
TGAGCTTGCC ACCCGAACTC TGCCGTTTGC ACAGTCCCTG CTGATGCTTA TCCTGGTGTG    5400
CCTGTTCCCG TTGATGATTG CGCTGGCCGC ATCAAATCAC ACTATGTTTG GGCTGAACAC    5460
CCTGAAAATA TACATTTCCG GTTTTATCTA TTTCCAGATG TGGCCGGTGA TGTTCGCCAT    5520
```

-continued

| | | | | | |
|---|---|---|---|---|---|
| CCTTAACTAT | GCTGCCAACT | ACTGGCTGCA | GAGTCAGTCC | GGGGGCACGC | CTCTGGTGCT | 5580 |
| GGCCAACAAG | GATGTAGTGG | CACTGCAGCA | TTCGGACGTG | GCGAATCTGG | CAGGGTATCT | 5640 |
| GTCGTTGTCC | ATTCCGGTGC | TGTCGTTCGT | ATCTGACCAA | GGGGGCTGCG | GCGATGGGCT | 5700 |
| CTCAGGTGGC | AGGCAGTGTC | CTCAGTTCGG | GCGCCTTCAC | GTCGGCAGGT | GTGGCAGCAA | 5760 |
| CCACGGCGGA | CGGGAACTGG | TCGTTAACA | ACATGTCAAT | GGACAATGTC | AGCCAGAACA | 5820 |
| AGCTGGATAC | CAACCTGATG | CAGCGTCAGG | CCAGCAGACG | TGGCAGGCAG | ATAATGGTTC | 5880 |
| CACGCAGACG | CAGACGCCGG | TGGCCATACG | GTATCGACGG | CTCAGGCGCA | ATGTCGAATC | 5940 |
| TGCCGGTGAA | CATGAAGCTC | AGCCAGCTGG | CCAGCAGTGG | TTTCCAGGAG | TCTGCCCGCC | 6000 |
| AGTCGCAGGT | CCAGGCGCAG | ACGGCGCTCG | ATGGCTACAA | CCACAGTGTC | ACCAGTGGCT | 6060 |
| GGTCGCAGCT | CTCACAGCTG | TCTCACCAGA | CCGGTACCAG | CGACAGCCTG | ACCAGCGGCA | 6120 |
| GTGAAAACAG | CCAGGCCACT | AACTCAACGC | GCGGCGCGAG | CATGATGATG | TCGGCCGCTG | 6180 |
| AAAGCTATGC | GAAAGCTAAC | AATATCTCGA | CGCAGGAAGC | CTATAACAAG | CTGATGGATA | 6240 |
| TCAGTAATCA | GGGTTCTGTA | TCTGCAGGCA | TTAAAGGTAC | GGCCGGAGGG | GGACTTAATC | 6300 |
| TGGGCGTTGT | TAAGCTT | | | | | 6317 |

( 2 ) INFORMATION FOR SEQ ID NO:22:

( i ) SEQUENCE CHARACTERISTICS:
        ( A ) LENGTH: 6914 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterobacter cloacae
        ( B ) STRAIN: Clinical Isolate ET- 49

( x i ) SEQUENCE DESCRIPTION: SEQ ID NO:22:

| | | | | | |
|---|---|---|---|---|---|
| AAGCTTTTCG | AGTTCGCCAT | CCGGCAACAG | CTCACTGAGC | TTTTACGCGC | CCAGGGTGCC | 60 |
| TTTGAACTCA | ATTCCCAGCT | CAGTAAGGCG | GTCCTGAATA | ATCTCTTTGC | GAGATTTTTC | 120 |
| ACTGGTACCG | GCATCAGGTG | TTGCAGGTTT | CAGCTCGCCA | CCAGCCTCGC | CCTTCATCAG | 180 |
| CCGGACGTTA | GACTTCAGCG | CCGGGTGAAG | ATCTTTCAAC | TCCACCACGT | CGCCAACCTT | 240 |
| TACGCCGAAC | CATGGGCGCA | CAACTTCGTA | TTTAGCCATG | CTGTTTCCTT | ACGCCAGGTT | 300 |
| AGCGCCGTAG | ACAACGCCAG | ACAGGCCTGA | TCGTCTGCAG | TAATTTGCAG | GCCTTCAGCA | 360 |
| GACATGATCT | GGAAGTTGTA | GTTAACGTTA | GGCAGTGGGC | GCGGCAGTGG | CACAACGCCA | 420 |
| ACAGCCATAC | CCACCAGTGG | GGAGATCACG | TCACGACGAC | GAACGTACGC | GATAAACTCG | 480 |
| TTACCGGTCA | GCGCGAAGTC | ATGCGGATTT | CTTTCACCGG | TGCGAATGGC | AGAACAGCCT | 540 |
| GCAGGAGAGT | GCCGCTCACC | ACACCATTAA | CTACGTATGG | CTGAGCCATA | TTTGCCCAGA | 600 |
| TCTCAGGGGA | AACCCACATC | ACATCATACT | GAGCTACTTT | GTTGGTGCGT | GCGGTGGTAC | 660 |
| CGAATGCTCC | TTTACCAAAG | AACTCAAAAT | ATTGAGTCGT | GGTTGCGCTG | GTCAGGTCGA | 720 |
| TGTTCGCACC | ACCAGCACCA | GAACCGAGGT | TAATCTTCTT | GGTGTTGCGG | TGGTTCTTGA | 780 |
| TGCCCTGCGC | CGGGTAGGAC | TGAACCTGAA | TTTTGAATC | GCCGTTCAGG | TAGTAGTTGA | 840 |
| CGCGCTTCTG | GTTGAACTTG | CGCATCTTCG | CCATCTGCGA | ATCCAGAACC | AGATCAATGC | 900 |
| CTACAGAGTT | AAGGCCAGCA | GCATGACGCC | AGTTAACACC | GTAGCCAGCA | GTGAACACCG | 960 |
| GAATCGGGTC | GCCATCGCTC | GCGTAGTCAG | TGTGGTCGAA | GGAGAATGGC | GCCTGACCAT | 1020 |
| CGATGCTTAC | TGACACGTCG | TCAGCGATGT | CGCCGACCAC | GTTATACAGC | TTGGCGGTTT | 1080 |

```
TACCAACCGG CAGCACGGTC TGAACGCCGA TCAGGTCGTT TACGATTTCC ATGCCAACTT  1140
CCTGATCCCG CAGCTGCAGC ACCTGGTTGT CAATCTCAGC CAGAAGTCA  CGGGAGAAAC  1200
CGCCAACAGC GTTACAAGCC AGCATGTCAG GCGTCATCAT TGCGCGGTTA GCTGCAATGA  1260
TGGAATCGTT CTGTAGGTTC CACATGTTGC GGTTTGCCCA CAGCTCACTC CAGTGCCCGC  1320
CGAGGCGGGA GTTAGTCGCC AGCGTCTCTT TAGAGAAGTA CATATGTGTT TGTCCTTTTG  1380
TTACGCGCCA GCTGCGGCGA CAGTGCCAAC GCGCATACGC ACGCGAATGA AGTCAGTGGT  1440
GCTGGCCGCG ATGGTGTATT CATCCTGGCT GTAGCCGATC ACTGAATCAG TGTCGGATGT  1500
GGCAAGGGTA AACTGACCGG CAGTTCCAG  CTTGATCGGG CTGTCTTTTT TATACGCACC  1560
AGGCAGGCAG CGCAGCGCCA GCTCACGACC TTCTTCGACG TAGTTACCTA CTGCCGAATC  1620
CCCGGCAGGG ATTTCTTCGG TGATTGTCAG GCCCTGGTGA TAACCGACAT CGATGATGTA  1680
CAGGCGGCCG GTTAGCGCGG TGGCCTGAGC GAATTTATCG GATGAGTTGA TGGTTGCGGC  1740
GGTGCCAGGA AGCAACCCGG CGGCCGTTGT GCGGGTTTCG GTCTTGTACA GAGACTGACC  1800
GTCGATATTA ACGCGACGAT AACGTGGCAT TATTCCGGCT CCTTACTTGA AGTGTTCGTC  1860
TGCGGCTGGT GCGCCGGTTT CTTTGTGCTG CTGAGCATTG TTGGTGCCCA GCGACTTGAA  1920
CATCGCGTCC AGAGCTTCGC CTGACAGAGC GTTCGCGAGC GATATCGCCA TGGACCTTCG  1980
CAACCGCTTC GCGCTTTGCT TTCTCTTCGG CACGGGAGTT CGCGGTAAGG GTTTCCGCGA  2040
GTTGCTTCTG ATTGGCCTGC AGCGCATCAA CCTTTTCCGC GAGAGGCTTA ATAGCCGCTT  2100
CAGTATTGGT CGCAACAGCC TGGCCGATCA TGCTGCCGAT TTGTTCCAGT TCTTCTTTGG  2160
TTAAAGGCAT GTCGCCTCCG TTTTGTGGTT TGGTGCAGGC TGTTCCTGCG GTGTGAATAG  2220
AGCTTTGAAT TGTTAGCGAC GACTGCCACC CACGACTCCT GGCGCGCTAC TGCGGTTCCG  2280
GTATCGTCGA TTGTGATCTT CCCGCCATCA GCGAATACCG TAAACCTGAG CATCACCGCC  2340
ATTTCGCACG ATGACCACCT GCGAGTCAGT GAGTCAGCAA CCCAGGCATA TTCATCCGTG  2400
CCCGGCGCAA ACTTGGCTTT GGCTGCCCGA TCGAGACGCT GCTCGCGCTC CCGGTAGGAT  2460
TCACCCACCA GCGCGCCGGA GTTCGCTTTA AGCGGCTGCG CCAGATCGGC GTTTACCATC  2520
AGGCCAACGC CCTGCTCAGG GGTGGCGGCT CCGACTTCGT GCAGTAGGAT CGCGTCGTGG  2580
TCCATGCTGT GAATCTTCGC CACCCACTCG GCACCCGTAG CTCTCTGTTG TTCGTTAGGC  2640
TCAAGCTGGT CGAGGAAAGC GGCGACACTG GTATGAATCG GCGGAACGTC ATCGCCGCGC  2700
TCGATGGCTG CGACGCGCTC AAGTAGTTCT CGGCCACCTT CAGACTCACC GGCGCGGGCA  2760
ACATCAACCC ACTTTTCGAG GTAGATACGA TTACCGGACT TCTTAACGTT GCGGTTCCAC  2820
GCGCCGATAT GGCCTGCGTT AATCCCCTCC GGGGAGAAAG CAGACACGAA CTGACCATTA  2880
ACCTGAGGGT GGCCCAGCGG CGCCAGGGTA CCTTCCAGCC CCTTATAGTG GGCGTCGATT  2940
TGCTCTTGCG TGTACAAGCC GCCATTCATG ACGACGTTAG CTGGAAGTGT GTAGCTCGGC  3000
AGCACCAGGT GCTCACGCCC GTTGTATGTT TCGCGCCGGA TAGACTGGCT GTTCACCTTT  3060
GTGGTGATGT TGACCTGAAT ATGCTCACCA TGTTTCGGTG CCTGGATTGG ACGCTGTGCT  3120
TCGTGGTTTA CCTGGAATTT CATGAGTTAT TTCTCCGCCC AGGCGTAACC GCTCGCCTGC  3180
ATCGATTTAT ATTCCTGTTT GAGTTTCGTG ATGGTGTCCG GGTATTCCGG CTTGCCGTCC  3240
GCATCCACCA GCACCGACTG CTGGCTGCAT TTGCAGTTGA TGGAGTTGCC ATCTTTGCTG  3300
TACCAGTCAC GCACCTCTTC GTTGGTGTAG AGGTGGGCAT GGGCGCACTG CGTGGGTATG  3360
TCGCGTTGTC GGCGACAGAG CTGAGATGTG AACCAGCAGC GTTTAAGGC  CGAACAGGTC  3420
ATTCGCCTCT TGGTCTTCAT CCCACTTGGC CCGGCGCAGC GCGGTAGTCA CTTCAGTGCG  3480
```

-continued

| | | | | | |
|---|---|---|---|---|---|
| TGCTATCCGG | TTAGCCCGGC | GTTTCTCGAT | GCCGGTCTGG | TCTGTCAGGT | TGCGGGCAAT | 3540 |
| GTCCAGAGGA | TTGAGCCCGC | GCCCAACACC | ATCAGTAAGA | CACGCGCCAT | GTCGCGCTTA | 3600 |
| ACGTCAGCCG | TCAGCCCCTT | CATTTCCTCA | AATACACGCG | CATGCACCAG | CGCCATGCGT | 3660 |
| TTCTGATACT | GGTCGCTTGC | GAGGATGGAG | CCAGCGACT | CACGCCCGGC | TGCGTACACC | 3720 |
| GGGGATTGCT | GACTGAGGTT | GTAGAACGAC | TGCCCGGTCC | CTTTTTCCGA | AGCCAGATCG | 3780 |
| ATGTACTCGT | AAAACCACAG | GTCGTAATCG | CCACCTTCAA | GCAGTACCTG | ATCAACCAGG | 3840 |
| TAACTGGCAT | CGTTCAGGAT | GATGGAGAGT | AGCATTGGGT | TTAGCTGGTA | TTCGTATCTG | 3900 |
| GCGTTTACTG | CGAGGGAGGA | AGGTATTTTG | TTGAGTGCTG | ATTTGTACGC | CTTGCCAATC | 3960 |
| TTATTCATCC | GCCTGGCGAA | GTCTTTCATT | GCCCGGCGTT | CCAGCGCATC | GGCTCCGGTC | 4020 |
| GGATCCTGAT | AGTTACGCGG | CAGAATCGGT | GGCTTCGTCT | TCTTCGTCGC | CATCCTCTTC | 4080 |
| TCCTAATGGA | AATTCATCGA | CGTTTTCATA | ACCGGCAGCA | GTGCGGAATT | TCTTCACGAC | 4140 |
| TAAAGGCTGG | TTTTTCTCCG | CTCCCCTGGA | ACGTCTGGTT | AATCTCTGCC | ATGGTTTTGG | 4200 |
| CATTTGCGAG | TTTCTCAGTT | CCAGTCTGTT | CGTTGAGGTC | ATCCCAGATA | ACCGTCTTCT | 4260 |
| CGCTGACTGC | ATCAATAATT | TTCAGGTCGA | TGAGCTTGTC | ACTGAAGTCT | TCAATTTCGA | 4320 |
| ATGACAGGTC | ACCGCGCCGT | GACTGGCAGC | GCGCGTTGAA | ATATTTCTGA | TCCTCGGTGC | 4380 |
| TTGCCCTTTC | ACCCGTCTGC | ATCCCAACCA | GAACCTTCAC | AGGGATATCA | ACAGATGCAG | 4440 |
| CGAAGGTTTG | CAGGTTGACG | TTATAGGTCG | CTGACGGATC | CGCTACAGCT | GTGACCAGTG | 4500 |
| GTGTGACTGT | AGCCCCTTGG | GTTGTCATCA | GAACATCGTT | ACCACGGTTC | ATTTCCCCGG | 4560 |
| CAACTTCGTT | AAACTTATCC | TGCAACTCGT | CCATGTCACG | CCATAAAGTG | ACGCGAGATT | 4620 |
| GTTGAAATCG | ATTTCCTTCT | CAAAGTTGAC | ATTAAGCTGC | CGCGCGGCGT | TCTTTAGGAA | 4680 |
| TGACTCACCA | GAACCACCCT | CGACCTTCTC | AAGGCTGACG | CAGGCGTTAT | AGCCAGGCTC | 4740 |
| AAGGAAGCCA | ATAGCATCAT | TAGAATAGTC | ACCAAGGATA | AAGACGCGAT | CGGGATGTAC | 4800 |
| GAAGCGCTGA | TTAGTTCCAC | CGCTTGGAAG | GCTCTCAACA | TATTTCCACT | GCTTTGGCTG | 4860 |
| CCCGTAGCCT | GCCGATTTCT | GGTCAGTTAC | CCACTCGCTG | ACTGTTAATG | ACCCAGCCCA | 4920 |
| TGCGATCGTA | ACCTTTTTTA | GTGACTTGCC | ACGAACAACA | GGCTGATCCC | ATGTTCTGGA | 4980 |
| ATCATTGATA | TGCAGCAGGA | TACCCGCATA | ACGTCCGACC | TGTCGGCGGC | GGTCTGCTTC | 5040 |
| AGCAAAAGCC | CGCCAAAGGC | GCTTTGTGAA | AACCTTTTTG | GTGTTCTTCT | CCCAGGCAGT | 5100 |
| TTCATCCTTA | CTCTCGTCGG | CATCATCACC | CTCGATGATT | TCCGGGTTGG | TCTGCCAGCA | 5160 |
| CTTGCCCACC | AGCTTCTCTA | CTGCGCCGTG | GGCTATTCCA | CCGCGACGAT | ACAGTGCGTA | 5220 |
| GAGGTTTTCG | TAAGTGACCT | GCTCAGGGAA | TCCATACTCG | CACCATGCGG | AATGGCGCTT | 5280 |
| ATTGTCCAGC | CCCATTGTAG | GCGCCAACAG | CCCCATACGG | GCACGGGCCA | TCCGCGCATC | 5340 |
| GTTCAACGCA | TGGTTGACGG | CGAGAGTTAA | TTTGTCAGTC | ATGGTTTGTC | CGTTGGTGGA | 5400 |
| TTTAAGGCAT | AAAAAAAGGC | CGCTTTGGCG | ACCTTGTGGC | TATTTAAAAA | GCTAAACTCT | 5460 |
| GTTGAACGAA | ATAAACATAA | TCTGCTCAGG | CTTAACGCCA | TAATCACTTG | CCAACTTCTG | 5520 |
| AGTGCACTCA | ATTAAGACAG | TTGATGCAGA | TTTCGAAGAG | CTTGCACCAT | AAATTTCGAA | 5580 |
| GTTTTCAAAT | ACTCCGCCGT | TGGTGTGGTA | AATCTTATAT | GACATAAACC | AATCATTCAT | 5640 |
| AATATCTACT | CCCTTACAGA | ATTGAGTAGA | TATTATCGGC | AAGTGCATAT | GTTTCTTTAA | 5700 |
| ATTATCTCAA | CCTTTTCGGG | ATCATCATCC | CGGCCATCTG | GCCCTTACGT | TTAATGTGTC | 5760 |
| CGTCGAGGCT | GTAGCGAATA | CCGTCCCAGC | AGTGTTCGTA | ACCGTCTGCC | AGTTTAGGCA | 5820 |
| ATACCTCGCC | GGTGATGCGG | TCCGTTTTGT | AGGACCACAT | GCGGGCCTCT | CTCGCCACAT | 5880 |

-continued

| | | | | | | |
|---|---|---|---|---|---|---|
| TCTTGCAGCG | AGGATGGATA | ATGATTTCGT | CAAAGCCGCG | AAGATGCGCG | ATACCGTCCT | 5940 |
| CAACACTCCC | CTGCCATTTC | TCGGCAGCCG | AGATGTTGAA | GCCCTGGCGC | TTGAGATAGC | 6000 |
| TGATAGTCTC | GGGTCGGGCG | GAGTCGGCCT | TGATGGGCCA | GTCACGCGAT | CCGGGGATTG | 6060 |
| TGTCGTATAG | CTCTGGCATA | TGGTCGAGCT | CTGTCTGCTG | ACCGTATGCC | TCGTATTCGA | 6120 |
| TGTACAGCCG | GTTGTGCAGG | ATGAACGAGC | GCACCAGCGT | GTTAGGGTCT | TTGGCGAAAC | 6180 |
| CGAAGTCAGC | ACCGAAGAAA | AGGCGATCGG | CCTCTTTCCA | TAGCTGGTCC | GAGAACTCAG | 6240 |
| CGATCCGGTA | TTTACCGGCC | AGCACCTGCT | TATCAGAGTT | TTCGAGGTAA | GCACCTTCCC | 6300 |
| AAACCCACGC | GTATGTTGCC | GGGTCAAGGC | GGCGCTGATC | GTTCTGTCGC | TCACCTTCCA | 6360 |
| GCACGTCGGG | GAACCATGGA | TTATCCGTGT | AGTTCATCTC | AACGTGATAC | AGTCGTCGCC | 6420 |
| AGCCTCTTTA | CGGAAACGCT | TATCCGTGCG | CTGCCGTCGC | GCTCCGGGTT | CCATGTCACC | 6480 |
| CAAATCTCTG | AACCTTCCTC | ACGAACGGTC | GGGCTCAGCT | TCTGCCAGGC | TATTTCGCTG | 6540 |
| ACTGATTCAG | CCTCATCAAC | CCAACAGAGC | AAGATGCGCG | CTTTCGACTT | GATGCTGTCG | 6600 |
| AGGTTATGCC | GCAGACCGCA | GAACACGTAG | TTAACGCTCT | TGTCGATGGT | GCGGATGTAC | 6660 |
| TTCTCGCCGA | TATCAAAGTT | GGAAGCCAGC | CAGGGAACAG | ACAGGATAGC | CTGTTTCACC | 6720 |
| TCCTGCATAC | TCGACTCTTC | CAGTGAGTTC | ATGAATTCAC | GCGCACAGAG | CACCACGCCG | 6780 |
| CTTTCACCGT | TCATCATCGA | CTGATACGCC | TTTACGGCTG | TCATCAGCGC | AAAAGTGCGC | 6840 |
| GTCTTGGCAC | TACCACGCCC | ACCATGCGAG | CACCGGTAAC | GCTTATTCTC | GGCGATGAAC | 6900 |
| AGTGGCGCAA | GCTT | | | | | 6914 |

( 2 ) INFORMATION FOR SEQ ID NO:23:

( i ) SEQUENCE CHARACTERISTICS:
        ( A ) LENGTH: 5975 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Klebsiella pneumoniae
        ( B ) STRAIN: Clinical Isolate Kl- 50

( x i ) SEQUENCE DESCRIPTION: SEQ ID NO:23:

| | | | | | | |
|---|---|---|---|---|---|---|
| AAGCTTATTC | CACGCTGGAG | GCGTCCGGGA | TTATCGGCGT | CAACGCTATC | GCCGGCATCG | 60 |
| CCGGGACCAT | CATCGCCGGC | ATGCTCTCCG | ACCGCTTTTT | CAAACGCAAC | CGCAGCGTGA | 120 |
| TGGCCGGATT | CATCAGCCTG | CTGAACACCG | CCGGCTTCGC | CCTGATGCTC | TGGTCGCCGC | 180 |
| ACAATTACTA | CACTGATATT | CTGGCGATGA | TTATCTTCGG | GGCCACCATT | GGCGCTCTGA | 240 |
| CCTGCTTCCT | TGGCGGGCTG | ATCGCCGTCG | ATATCTCTTC | GCGCAAGGCC | GCCGGGGCCG | 300 |
| CGCTCGGCAC | CATCGGCATC | GCAGCTACGC | CGGCGCCGGC | CTGGGCGAGT | TTCTCACCGG | 360 |
| GTTCATTATT | GATAAAACGG | CTATCCTTGA | AAACGGCAAA | ACGCTGTATG | ATTTCAGCAC | 420 |
| GTTGGCGCTG | TTCTGGGTGG | GTACGGTCTG | GGTTCNGCGC | TACTCTGTTT | TACCACTGCC | 480 |
| GCCATCGTCG | CCCGGCGCCA | TGCCGTCGAA | CGGCAGACCT | CGTTCTCCTC | ATAACCGATT | 540 |
| AACGAATAAG | GAAGAAGATA | TGATGCCTGC | AAGACATCAG | GGGCTGTTAC | GCCTGTTTAT | 600 |
| CGCCTGCGCG | CTGCCGCTGC | TGGCGCTGCA | ATCTGCCGCC | GCCGCGGACT | GGCAGCTGGA | 660 |
| GAAAGTGGTC | GAGCTCAGCC | GCCACGGTAT | TCGTCCGCCG | ACGGCCGGCA | ACCGGGAAGC | 720 |
| CATCGAGGCC | GCCACCGGCC | GACCGTGGAC | CGAGTGGACC | ACCCATGACG | GGGAGCTCAC | 780 |

-continued

| | | | | | |
|---|---|---|---|---|---|
|CGGCCATGGC|TATGCCGCCG|TGGTCAACAA|AGGGCGTGCG|GAAGGCCAGC|ATTACCGCCA 840|
|GCTCGGCCTG|CTGCAGGCCG|GATGCCCGAC|GGCGGAGTCG|ATATACGTGC|GCGCCAGCCC 900|
|GCTGCAGCGG|ACGCGAGCGA|CCGCCCAGGC|GCTGGTGGAT|GGCGCCTTCC|CCGGCTGCGG 960|
|CGTCGCTATC|CATTATGTCA|GCGGGGATGC|CGATCCCCTG|TTTCAGACCG|ACAAGTTCGC 1020|
|CGCCACGCAA|ACCGACCCCG|CCCGCCAGCT|GGCGCGGTGA|AAGAGAAGGC|CGGGGATCTG 1080|
|GCGCAGGTCG|GCAGGCGCTG|GCGCCGACCA|TCCAGCTATT|GAAACAGGCG|GTTTGTCAGG 1140|
|CCGATAAGCC|CTGCCCGATC|TTCGATACCC|CGTGGCAGGT|CGAGCAGAGC|AAAAGTGGGA 1200|
|AGACCACCAT|TAGCGGACTG|AGCGTGATGG|CCAATATGGT|GGAGACGCTG|CGTCTCGGCT 1260|
|GGAGTGAAAA|CCTGCCTCTC|AGCCAGCTGG|CGTGGGGCAA|GATCACCCAG|GCCAGGCAGA 1320|
|TCACCGCCCT|GCTGCCGCTG|TTAACGGAAA|ACTACGATCT|GAGTAACGAT|GTGTTGTATA 1380|
|CCGCGCAAAA|ACGCGGGTCG|GTGCTGCTCA|ACGCTATGCT|CGACGGCGTC|AAACCGGAGC 1440|
|GAATCGAACG|TACGCTGGCT|GCTGCTGGTG|GCCATGACAC|CAATATCGCC|ATGGTGCGCA 1500|
|CGCTGATGAA|CTTTAGCTGG|CAGCTGCCGG|GCTACAGCCG|GGAAATATC|CCGCCGGGCA 1560|
|GCAGCCTGGT|GCTGGAGCGC|TGGCGCAACG|CGAAGAGCGG|AGAACGCTAT|CTGCGGGTCT 1620|
|ATTTCCAGGC|CCAGGGCCTC|GACGACCTGC|GTCGTCTGCA|GACGCCGGAC|GCGCAGACCC 1680|
|CGATGCTGCG|TCAGGAGTGG|CATCAGCCGG|GCTGCCGTCA|GACCGATGTC|GGTACGCTGT 1740|
|GTCCCTTCCA|GGCGGCTATT|ACCGCCCTCG|GTCAGCGTAT|CGACCGATCA|TCCGCCCCGG 1800|
|CGGTAGCATG|GTCCTGCCGT|AGCGGCGCGG|TGTTTGTCCG|GGCCCGGGAA|AACCTTTTT 1860|
|TCCAGGCCGG|CACGACGTCC|GTTATCCGTT|GTCCGGCGCA|AACGCCCCGG|CGGCGACCTG 1920|
|CGCCGGGGTG|ACACCCGCTG|TCCAGCACCC|AGCCGCTTAT|CAGCCCAGCA|GGCGTGACGT 1980|
|CGAACGCCGG|ATTGTAAACG|GTGGCCCCCG|TCGGCGCCCA|CTGTACCGCG|CCGAAGCTGC 2040|
|CCGCCACTCC|GGTCACTTCC|GCCGCCGCGC|GCTGCTCAAT|GGGGATCGCC|GCCCCGTTCG 2100|
|GGCAATGGCG|GTCGAGGGTG|GTCTGCGGGG|CAGCGACGTA|AAACGGGATC|TGGTGATAAT 2160|
|GGGCCAAAAC|CGCCAGAGAA|TAGGTGCCGA|TTTTATTCGC|CACGTCGCCG|TTGGCGGCGA 2220|
|TACGGTCGGC|GCCGACCCAC|ACCGCATCCA|CCTGCCCCTG|CGCCATCAGG|CTGGCGGCCA 2280|
|TTGAATCGGC|GATCAGCTGA|TAGGGCACGC|CCAGCTCGCC|CAGCTCCCAG|GCGGTTAAAC 2340|
|GACCGCCCTG|CAGCAGCGGC|CGGGTTTCAT|CAACCCATAC|GTTGGTCACT|TTTCCCTGCC 2400|
|GGTGCGCCAG|CGCGATAACG|CCGAGGGCGG|TCCCTACCCC|GGCGGTCGCC|AGGCCACCGG 2460|
|TGTTGCAGTG|GGTCAGCAGT|CGACTGCCGG|GCTTCACCAG|CGCACTGCCC|GCCTCAGCGA 2520|
|TGCGGTCGCA|CAGCTGTTTA|TCTTCTTCGA|CCAGACGCAA|GGCTTCCGCT|TCCAGCGCCT 2580|
|GCGGGTAATC|TCCGGGCCAG|CGCTGCTTCA|TGCGATCAGA|TTATTCATCA|GGTTGACCGC 2640|
|CGTCGGCCGC|GCCGCGCGCA|GTCTCCAGCG|CCTGCTGGAG|TGCATCCCGG|TTCAGGCCGC 2700|
|GCTGGGCCAG|CAGGGCCAGC|AGCAGGCTGG|CGGACAGGCC|AATCAGCGGC|GCGCCGCGCA 2760|
|CCCCGCAGGT|ATGAATATGG|TCCACCAGCA|GCGCAACGTT|ATCCGCCGCC|AGCCAGCGTT 2820|
|TTTCCTGCGG|CAAGGCCTGC|TGGTCGAGAA|TAAAAAGCTG|ATTTTCACTC|ACCCGCAGGC 2880|
|TGGTGGTCTG|TAATGTCTGC|ATGTCGTTAA|ATCCCTGTTG|CGTTGTTGTA|TCACATTGTG 2940|
|TCAGGATGGA|ATCCAGAAGT|ATAGACGTCT|GAACGGCTTA|ATCAGAATTC|GAGGATCGAG 3000|
|GCAATGTCGC|AATACCATAC|CTTCACCGCC|CACGATGCCG|TGGCTTACGC|GCAGAGTTTC 3060|
|GCCGGCATCG|ACANCCATCT|GAGCTGGTCA|GCGCGCAGGA|AGTGGGCGAT|GGCAACTCAA 3120|
|TCTGGTGTTT|AAAGTGTTCG|ATCGCCAGGG|CGTCACGGGC|GATCGTCAAA|CAGGCTCTGC 3180|

-continued

| | | | | | |
|---|---|---|---|---|---|
| CCTACGTGCG | CTGCGTCGGC | GAATCCTGGC | CGCTGACCCT | CGACCGCGCC | CGTCTCGAAG | 3240 |
| CGCAGACCCT | GGTCGCCCAC | TATCAGCACA | GCCCGCAGCA | CACGGTAAAA | ATCCATCACT | 3300 |
| TTGATCCCGA | GCTGGCGGTG | ATGGTGATGG | AAGATCTTTC | CGACCACCGC | ATCTTGCGCG | 3360 |
| GAGAGCTTAT | CGCTAACGTC | TACTATCCCC | AGGCGGCCCG | CCAGCTTGGC | GACTATCTGG | 3420 |
| CGCAGGTGCT | GTTCACACC | AGCGATTTCT | ACCTCCATCC | CCACGAGAAA | AAGGCGCAGG | 3480 |
| TGGCGCAGTT | TATTAACCCG | GCGATGTGCG | AGATCACCGA | GGATCTGTTC | TTTAACGACC | 3540 |
| CGTATCAGAT | CCACGAGCGC | AATAACTACC | CGGCGGAGCT | GGGAGGCCGA | TGTCGCCGCC | 3600 |
| CTGCGCGACG | ACGCTCAGCT | TAAGCTGGCG | GTGGCGGCGC | TGAAGCACCG | TTTCTTTGCC | 3660 |
| CATGCGGAAG | CGCTGCTGCA | CGGCGATATC | CACAGCGGGT | CGATCTTCGT | TGCCGAAGGC | 3720 |
| AGCCTGAAGG | CCATCGACGC | CGAGTTCGGC | TACTTCGGCC | CCATTGGCTT | CGATATCGGC | 3780 |
| ACCGCCATCG | GCAACCTGCT | GCTTAACTAC | TGCGGCCTGC | CGGGCCAGCT | CGGCATTCGC | 3840 |
| GATGCCGCCG | CCGCGCGCGA | GCAGCGGCTG | AACGACATCC | ACCAGCTGTG | GACCACCTTT | 3900 |
| GCCGAGCGCT | TCCAGGCGCT | GGCGGCGGAG | AAAACCCGCG | ACGCGGCGCT | GGCTTACCCC | 3960 |
| GGCTATGCCT | CCGCCTTTCT | GAAAAAGGTG | TGGGCGGACG | CGGTCGGCTT | CTGCGGCAGC | 4020 |
| GAACTGATCC | GCCGCAGCGT | CGGACTGTCG | CACGTCGCGG | ATATCGACAC | TATCCAGGAC | 4080 |
| GACGCCATGC | GTCATGAGTG | CCTGCGCCAC | GCCATTACCC | TGGGCAGAGC | GCTGATCGTG | 4140 |
| CTGGCCGAGC | GTATCGACAG | CGTCGACGAG | CTGCTGGCGN | GGGTACGCCA | GTACAGCTGA | 4200 |
| GTGCGCCTGT | TTCCCTCACC | CCAACCCTCT | CCCACAGGGA | GAGGAGCAC | CCCCTAAAAA | 4260 |
| AGTGCCATTT | TCTGGGATTG | CCCGGCGNGN | TGCGCTTGCC | GGGCCTACAG | ATAGCCGCAT | 4320 |
| AACGGTTTGA | TCTTGCACTC | TTTCGTAGGC | CGGGTAAGGC | GAAAGCCGCC | ACCCGGCAGA | 4380 |
| CATGCGAGTA | CAATTTTGCA | TTTACCTTAC | CCTCACCCCA | GATACTCAAT | CACCGATAGC | 4440 |
| CCGCCGTTGT | AATCGGTGCT | GTAGATAATG | CCTTGCGCAT | CGACAAACAC | GTCACAGGAC | 4500 |
| TGGATCACCC | GCGGCGGCC | GGGACGGGTA | TCCATCATTC | TCTCAGCGCA | GCCGGCACCA | 4560 |
| GCGCCCCGGT | CTCCAGCGGG | CGATACGGGT | TGGAAATGTC | GTAAGCCCGC | ACGCCGGCAT | 4620 |
| TCTGATACGT | GGCAAAAATC | AGCGTTGAGC | TGACAAAGCT | CCCCGGCCGG | TTCTCATGCA | 4680 |
| GGTTGTGCGG | ACCGAAATGC | GCCCCTTTCG | CCACGTAATC | CGCTTCATCC | GGCGGCGGGA | 4740 |
| AGGTGGCGAT | GCTCACCGGG | TTGGTTGGCT | CGCGGATATC | AAACAGCCAG | ATCAGCTTCT | 4800 |
| CGCCGTCCTC | CTGGTTATCG | AGCACCGCTT | CATCCAGCAC | CACCAGCAGA | TCGCGATCCG | 4860 |
| GCAGCGGCAG | CGCGGTATGC | GTTCCGCCGC | CGAACGGCGG | GCTCCAGTTG | CGATGGCTAA | 4920 |
| TCAGCCTCGG | CTGGGTACGG | TCTTTGACAT | CCAGCAGCGT | CAGGCCGCCG | TCGCGCCAGC | 4980 |
| TGCGTAGGCG | TATCCCCGGC | AATAATGGCG | TGATGCAGCG | CATAGCGTTT | GCCCTGCGGC | 5040 |
| CAGTCCGGTG | TTTCACCGCC | CGCCTGGTGC | ATCCCCGGCA | GCCACCAGCG | CCCGGCTACT | 5100 |
| TCGGGCTTAC | GCGGATCGGC | CAGATCGATG | GTCAGGAAGA | TGTAGTCGGT | AAAACCGTCG | 5160 |
| ATCAGCGCAG | ACACATACGC | CCAGCGCCCG | CCGACGTACC | AGATGCGGTG | AATACCGATG | 5220 |
| CCGTTAAGCG | CACAGGAAACT | GATTTCCGC | GCTGCGCGGG | AGTGGAAATA | TCAAAGATGC | 5280 |
| GCAGCCCGGC | GCTCCAGCCC | CTGTCCTGCA | CATCGCTGAC | CGTGTCACCC | ACCGAGCGGG | 5340 |
| TGTAGTACAC | CTTCTCATCA | GCAAACGGG | CGTCAGCAAA | CAGATCCCGG | GCGTTGATCA | 5400 |
| CCAGCAGCAG | ATCGTCATGC | GCCTGGAGTG | CACGTTCCAG | GTGCCCGGCG | GCGCGGCAAT | 5460 |
| ATAGTTGACG | GTGGTGGGCC | GGGTCGGATC | GCGAACATCG | ACCACGGAAA | AACCCTGCGA | 5520 |
| CACCATATGG | CCGATATAGG | CGAATCCGCG | GTGCACCATC | AGCTGCACGC | CGTCCGGACG | 5580 |

| | | | | | | |
|---|---|---|---|---|---|---|
| ACCGCCCTGA | TCGCTATGGC | CAATCAGCCG | CATATTGCGG | CTGTATTCGG | GGGAAGGTAA | 5640 |
| TGCTGACATA | GGGGATCCCT | CTCGCCCGGT | GGCATGGTTT | TCCCCCTCT | CCTGCGGAGA | 5700 |
| GGGCCGGGGC | GAGGGCACCA | GGCCGCCGCC | CACCGCCACC | CGGCTTGATT | TTATTTGTTC | 5760 |
| TTCGCTTCCA | GCGTCGCGAA | CCACGGCGCG | ATAAAGTCTT | CGGTCTGGCC | CCAGCCAGGG | 5820 |
| ATAATTTTCC | CCAGCGACGC | CACGTTTACC | GCTCCCGGCT | GGGCCGCCAG | CAGCGCCTGG | 5880 |
| GGAATCGCTG | CCGCCTTGAA | GTCGTAGGTG | GCTGGCGTCG | GCTCGCCGGC | GATCTTGTTG | 5940 |
| GCGATCAGCC | GCACGTTGGT | CGCGCCGATA | AGCTT | | | 5975 |

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:24:

CGACGTTGTA AAACGACGGC CAGT                                                  24

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:25:

CAGGAAACAG CTATGAC                                                            17

1

PROBE FOR DIAGNOSING *ESCHERICHIA COLI, KLEBSIELLA PNEUMONIEAE* OR *ENTEROBACTER CLOACAE*

This is a divisional of application Ser. No. 08/362,577, filed as PCT/JP93/00936 Jul. 7, 1993.

[TECHNICAL FIELD]

The present invention relates to probes, prepared by making use of causative bacteria of infectious diseases, which are useful for detecting and identifying the causative bacteria.

[BACKGROUND ART]

In pathology, infection is defined as invasion and establishment of a foothold for growth in an organism by a pathogenic organism (hereinafter referred to as "bacteria"), then the outbreak of disease depends upon the interrelationship between the resistance of host and the virulence of bacteria.

In the infectious diseases, improvement in treatment methods of bateremia have been raised as an important issue. That is to say, bacteremia is not a disease caused by a particular bacterium, but is caused by emergence and habitancy of the various bacteria in blood, then onset thereof is clinically suspected when fever of about 40° C. persists for two or more days. If a patient is an infant or is suffering from terminal cancer with weakened resistance, the patient may die in one or two days, therefore, the bacteremia is a serious and urgent disease, and the improvement in treatment methods thereof have been awaited.

In the infectious disease, phagocytes including neutrophils, monocytes and macrophages primarily work in defense of the body. Emergence of bacteria in the blood is thought as invasion of predominant bacteria which have emerged from the tissue of the phagocyte.

Bacteremia is a state wherein the bacteria is emerged into the blood, and a large amount of antibiotic is administrated to treat it wherein the causative bacteria is sensitive to the antibiotic. Generally, since antibiotics lower the functions of the internal organs such as liver, it is necessary to pay an attention to reduce an administration of an ineffective antibiotic to a patient in a serious state.

When bacteremia is defined as a case wherein phagocytesis of cells can not overcome the virulence of bacteria, then the bacteria spread in the body through the blood, bacteremia with serious symptoms due to toxins produced by the bacteria is called as sepsis. Proof of sepsis, in the other word, establishment of the diagnosis requires a check on the items of 1) clinical symptoms, 2) culturing of specimen, 3) gram-staining of the bacteria contained in the specimen, and 4) shock state, then, upon completing the check of these items, the treatment method is determined. Accordingly, to quickly and reliably identify the bacteria have been awaited in the art.

In the present method for detecting and identifying bacteria in a bacteremia-specimen, it is a common procedure to identify in selective medium a specimen which have positive signal in a routine process of culture bottle. However, to successfuly culture the bacteria from these blood specimen is quite difficult, then, if a large dose of antibiotics is administrated when bacteremia was suspected, bacteria in the blood will not be cultured and grown in many cases, therefore, the rate of culture bottle positive case become extremely low.

Although available sub-routine methods include instrumental analysis of constituents and metabolic products of bacteria (Yoshimi Benno, "Quick identification of bacteria with gas chromatography", Rinsho Kensa, Vol. 29, No. 12, November 1985, lgaku Shoin ed.), a method utilizing specific antibody (Japanese Patent Provisional Publication No. 60-224068), and a hybridization method utilizing specificity of DNA (Japanese Phase Patent Provisional Publication No. 61-502376) have been developed, any of which are required to separate the bacteria and culture it. On the other hand, as a method established based on the function of phagocytes in infectious diseases, there is a method to examine, under an optical microscope, a stained smear of buffy coat wherein leukocyte of the blood sample is concentrated. Generally speaking, although the rate of detection of bacteria in buffy coat specimens from adult bacteremia patients is 30% at most, which is similar to that in earlobe blood specimens, it was reported that bacteria had been detected in seven cases of ten cases (70%) in newborn patients, therefore, an information concerning the presence of a bacteria in peripheral blood to be obtained by microscope examination on smear is an important for treatment.

Since the conventional methods necessiate the pretreatment which requires at least three to four days in total containing one to two day(s) for selective isolation of bacteria from a specimen, one day for cultivation, and one or more day(s) for fixation, and the culture thereof is continued in practice until the bacteria grow, the culture will needs one week or more even for C.B.-positive cases, therefore, this was a factor in high mortality of C.B.-positive patients being treated by the conventional methods. For example, according to the a report published in "The Journal of the Japanese Association for Infectious Diseases", Vol. 58, No. 2, p. 122, 1984, even though the blood culture positive rate was 28.6% (163 cases/569 cases), the mortality was as high as 84.6% (138 cases/163 cases).

Further, it may be impossible to distinguish contamination at the cultivation by indigenous bacteria. For example, *Staphylococcus epidermides*, which is one of Staphylococci and is the causative bacterium of bacteremia, stayed in the skin of the normal person, then, there is a risk on contamination of a specimen with this bacterium when a needle is inserted into the skin.

As an important matter, under such circumstances above, since many bacteria in a specimen to be cultured have been incorporated into said phagocyte and are dead or stationary immobilized, the number of growable bacteria is small even under appropriate conditions for cultivation, thereby, the actual detection rate of bacteria through culture specimen is as low as about 10%. In the other word, at this moment, 90% of the examined blood, which have been cultured for further one or more day(s), of the patient suspected clinically as suffering with bacteremia can not clarify the presence of bacteria.

In light of the situation above, the present practice depends on a treatment to be started when bacteremia is clinically suspected without awaiting the detection results, that is to say, a trial and error method wherein an antibiotic having broad spectrum is administrated first, and if the antibiotic is not effective after one or two day(s), another antibiotic will be tried.

According to the method to stain the bacteria in the specimen, the constituents of the living body are also stained together with bacteria, therefore, experience to quickly identify bacteria according to thier image through microscope is required, then there may be cases that can be hardly diagnosed as bacteremia.

Although bacteremia is a disease wherein a rapid and exact diagnosis have been required, the conventional diagnosis method can not respond to such requirements.

[DISCLOSURE OF THE INVENTION]

The present invention was established in view of the problems in the art, and is directed to a probe having a specific reactivity with DNA or RNA obtained from primary causative bacteria of the infectious diseases, then provide a genetic information by analyzing the base sequence of DNA in the probe.

By the probe of the present invention, for example, a causative bacteria of the infectious diseases is detected rapidly and exactly, without cultivating/proliferating the bacteria, through a detection of DNA held in the causative bacteria digested and incorporated gradually with the phagocyte. Then, if primers are designed by referring to an information on base sequence of these probes, causative bacteria can identify, without the hybridization, by amplifying the DNA with PCR technique.

When non-radioactive probe, for example, biotinylated probe is used for hybridization, since such probe can be detected with an optical microscope in a conventional laboratory without radio isotope handling facilities, the detection process would be rapid and simple.

[BEST MODE FOR CARRYING OUT THE INVENTION]

Figure 1:
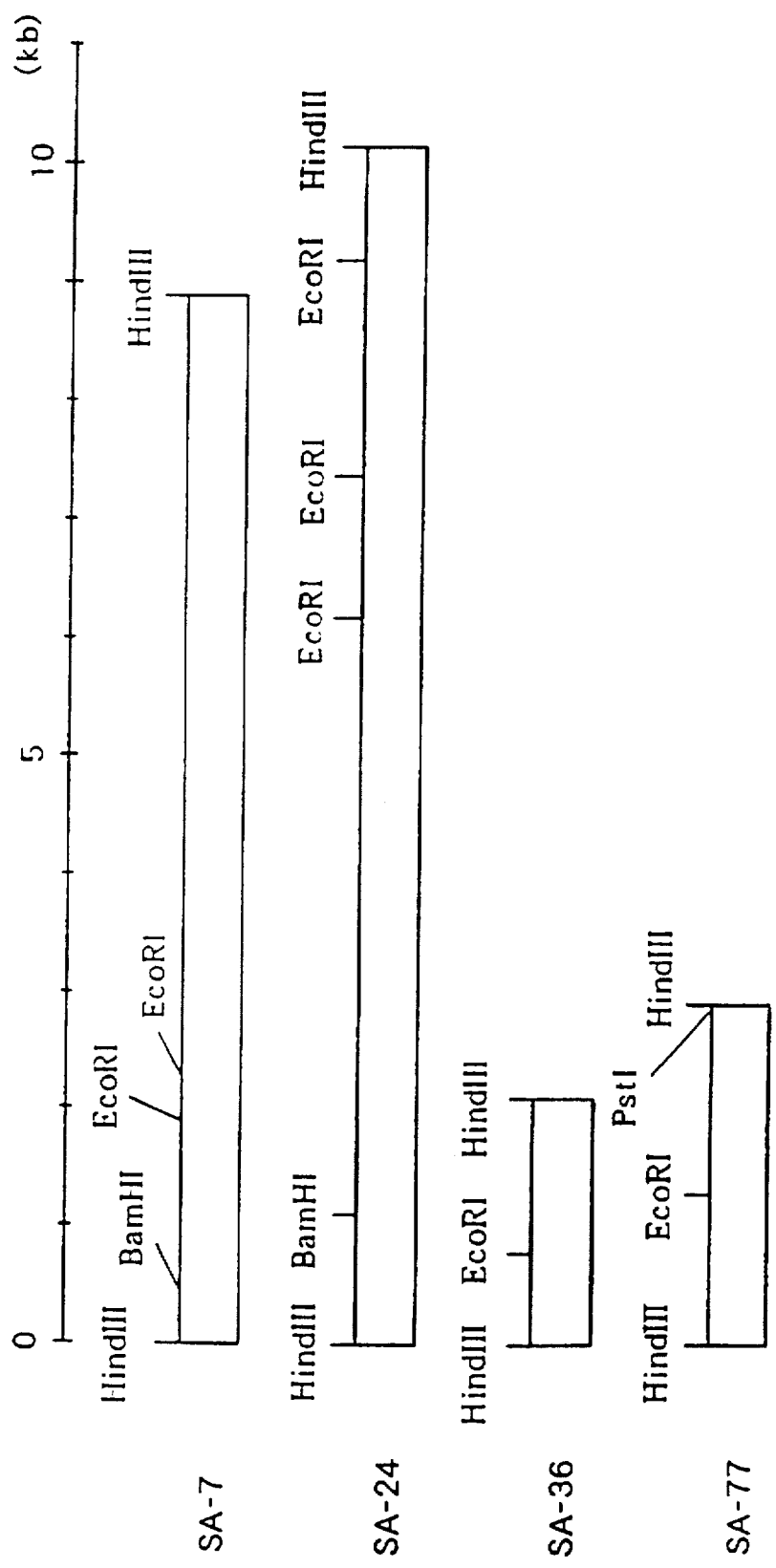
FIG. 1 is a restriction enzyme map of HindIII fragment on probe for detecting Staphylococcus aureus.
Figure 2:
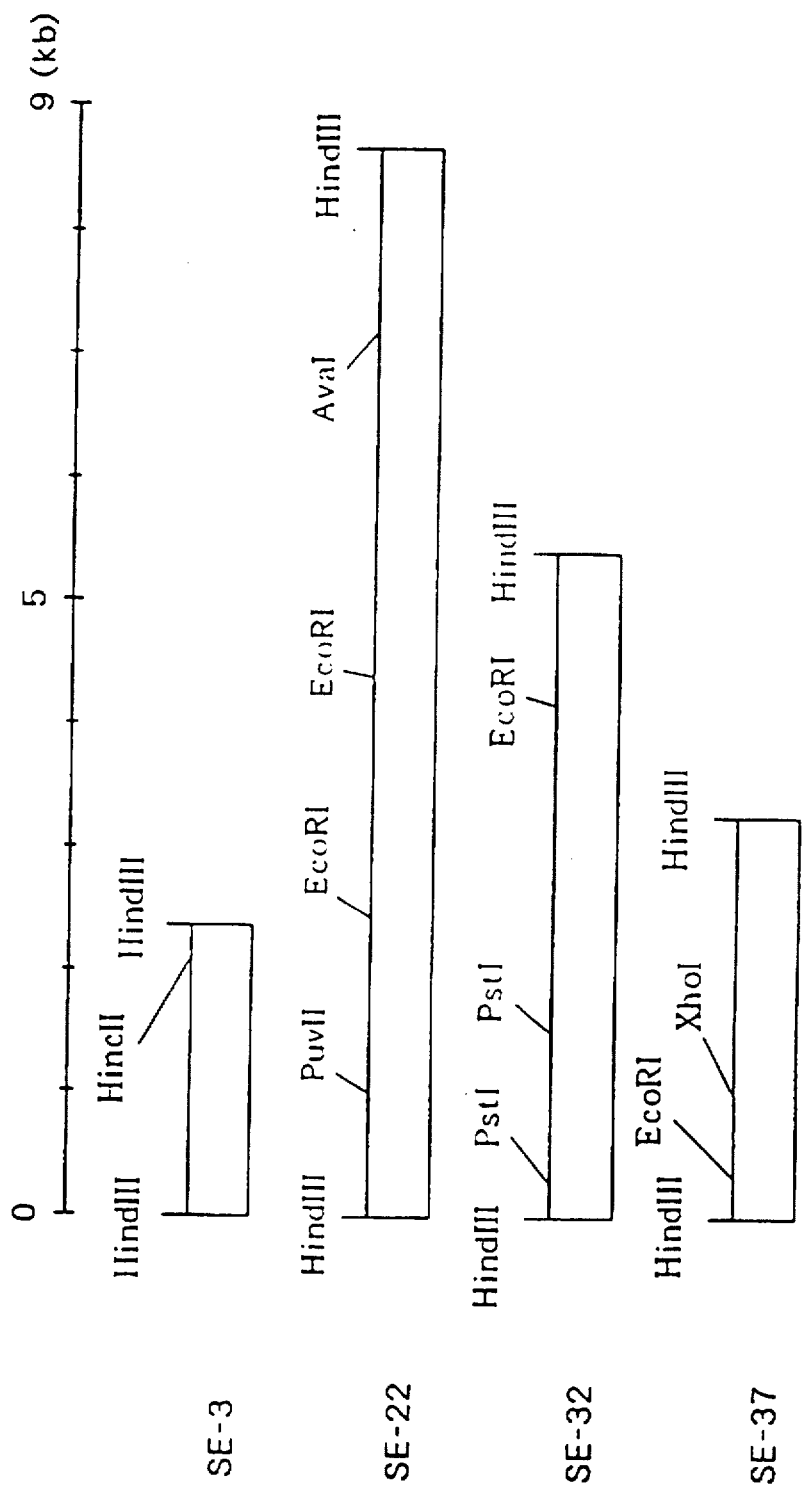
FIG. 2 is a restriction enzyme map of HindIII fragment on probe for detecting Staphylococcus epidermidis.
Figure 3:
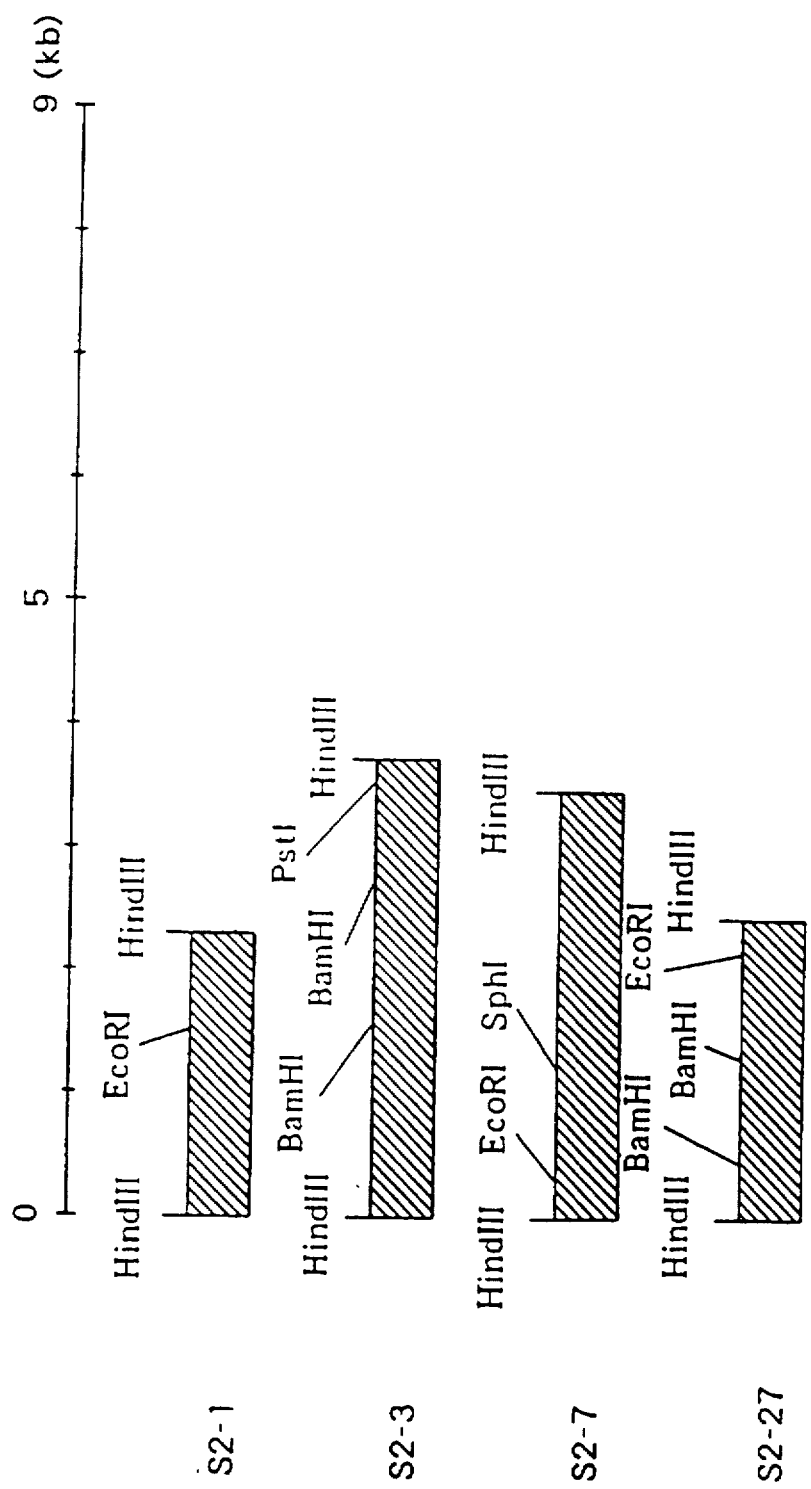
FIG. 3 is a restriction enzyme map of HindIII fragment on probe for detecting Enterococcus faecalis.
Figure 4:
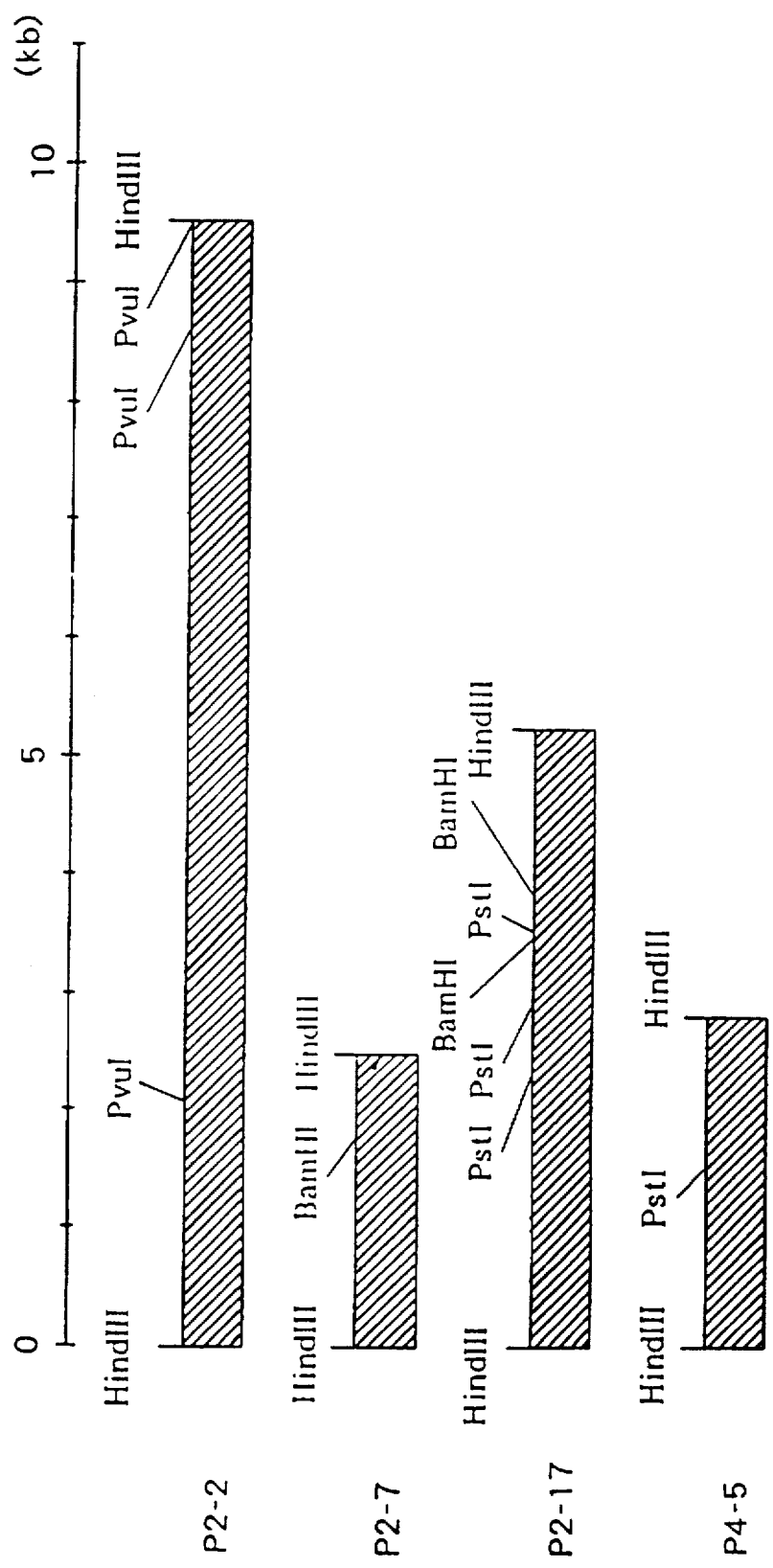
FIG. 4 is a restriction enzyme map of HindIII fragment on probe for detecting Pseudomonas aeruginosa.

Examples on probes prepared from Staphylococcus aureus, Staphylococcus epidermidis, Enterococcus faecalis, Pseudomonas aeruginosa, Escherichia coli, Klebsiella pneumoniae and Enterobacter cloacae (J. Infection, vol. 26, pp. 159–170 (1993), J. Clin. Microbiol., vol. 31., pp. 552–557 (1993)) respectively listed as relatively popular causative bacteria of the infectious diseases, especially bacteremia were described as follows.

EXAMPLE 1

Preparation of DNA Probe from Causative Bacteria of Infectious Diseases (1) Isolation of Causative Bacteria of Infectious Diseases Blood collected from the patient who have been suffered with targeted diseases were applied to Blood Culture Method (BBC System: Blood Culture System; Roche) and to a conventional identification kit (Api 20, Apistaf, Apistlep 20: Bio-Meryu), and the each causative bacterium was isolated and identified according to the manual of said kit.

(2) Extraction and Purification of Genomic DNA from Isolated Strain

Strains isolated in the above (1) was cultivated overnight in BHI (Brain Heart Infusion) medium, collected the cultivated bacteria, added thereto achromopeptidase in stead of lysozyme, then, Genomic DNA was extracted according to Saito-Miura Method ("Preparation of Transforming Deoxyribonucleic Acid by Phenol Treatment", Biochem. Biophys. Acta. vol. 72, pp. 619–629), and extracted DNA was digested with restriction enzyme HindIII and was random cloned into vector pBR322.

(3) Selection of Probe having Specificity to Species of Origin Bacteria Escherichia coli containing each clone prepared according to Manual of Maniatis (T. Maniatis, et al., "Molecular Cloning (A Laboratory Manual)", Cold Spring Harbour Laboratory (1982)) was cultivated with small scale culture, and obtained plasmids containing each clone.

These plasmids were digested with restriction enzyme HindIII, thereby inserts were separated completely from plasmids with 1% agarose-gel electrophoresis (Myupid: Cosmo-Bio), then, were transcribed to nylon membrane with Southern-Transfer Technique (Paul Biodine A: Paul), and were cross-hybridized with a probe prepared by labelling $^{32}$P-dCTP (Amersham) through nick-translation to chromosome DNA from each bacteria species aforelisted.

In this hybridization, a probe which did not cross-react with any insert except for a probe prepared from the origin species thereof was selected as a probe containing DNA fragment which is specific to causative bacteria of the infectious diseases.

With regard to probes prepared from Escherichia coli, Klebsiella pneumoniae, Enterobacter cloacae, since these bacteria are belonged to the same group (enteric bacteria; Gram negative aerobic bacillus) as a causative bacteria of bacteremia (See, J. Infection, vol. 26, pp. 159–170 (1993), J. Clin. Microbiol., vol. 31., pp. 552–557 (1993), supra), and the cross-reaction had been confirmed among said three bacteria in the foregoing series experiments on the specificity, each probe prepared from one of said three bacteria was designated as a probe for detecting all these bacteria as a relevant bacteria.

Probes (denotation) selected from each species through the foregoing methods are listed in the following Table 1.

TABLE 1

| SPECIES | DENOTATION |
| --- | --- |
| Staphylococcus aureus | SA-7, SA-24, SA-36, SA-77 |
| Staphylococcus epidermidis | SE-3, SE-22, SE-32, SE-37 |
| Enterococcus faecalis | S2-1, S2-3, S2-7, S2-27 |
| Pseudomonas aeruginosa | P2-2, P2-7, P2-17, P4-5 |
| Escherichia coli | EC-24, EC-34, EC-39, EC-625 |
| Klebsiella pneumoniae | KI-50 |
| Enterobacter cloacae | ET-12, ET-49 |

Restriction enzyme maps of each probe were also illustrated in FIGS. 1–6 respectively.

EXAMPLE 2

Evaluation on Species-Specificity of Each DNA Probe

Reactivity between each probe and DNA from causative bacteria of infectious diseases were examined acooding to the following method.

First of all, as subject strains for an examination, clinical isolates of Staphylococcus aureus, Staphylococcus epidermidis, Enterococcus faecalis, Pseudomonas aeruginosa, Escherichia coli, Klebsiella pneumoniae, and Enterobacter cloacae were isolated according to the method of Example 1 (1) above.

Then, DNA of each clinical isolate were extracted according to the method of Example 1 (2), and samples for dot-blot-hybridization were obtained by spotting certain amount (e.g., 5 μl) of DNA to nylon filter and selecting the isolates denatured with alkaline. Hybridization on DNA probes prepared from each subjected bacterium and labelled with biotin (Bio-dUTP; BRL) were performed overnight according to Manual of Maniatis, supra, under the condition of 45% formamide, 5×SSC, 42° C.

Samples obtained through overnight hybridization were washed twice with 0.1×SSC, 0.1% SDS for 20 minutes at 55° C., then, were detected the color reaction with Streptavidin-ALP conjugates (BRL), and evaluated the hybridization.

Experimental results on reactivity between each probe and DNA of each clinical isolate are illustrated in the following table 2 (i)-(vi). With regard to a denotation in the tables, denotation of "+" refers to the presence of a signal on hybridization, while that of "-" refers to the absence of a signal on hybridization.

TABLE 2 (i)

|  | SA-7 | SA-24 | SA-36 | SA-77 |
|---|---|---|---|---|
| Staphylococcus aureus | + | + | + | + |
| Staphylococcus epidermidis | - | - | - | - |
| Enterococcus faecalis | - | - | - | - |
| Pseudomonas aeruginosa | - | - | - | - |
| Escherichia coli | - | - | - | - |
| Klebsiella pneumoniae | - | - | - | - |
| Enterobacter cloacae | - | - | - | - |

TABLE 2 (ii)

|  | SE-3 | SE-22 | SE-32 | SE-37 |
|---|---|---|---|---|
| Staphylococcus aureus | - | - | - | - |
| Staphylococcus epidermidis | + | + | + | + |
| Enterococcus faecalis | - | - | - | - |
| Pseudomonas aeruginosa | - | - | - | - |
| Escherichia coli | - | - | - | - |
| Klebsiella pneumoniae | - | - | - | - |
| Enterobacter cloacae | - | - | - | - |

TABLE 2 (iii)

|  | S2-1 | S2-3 | S2-7 | S2-27 |
|---|---|---|---|---|
| Staphylococcus aureus | - | - | - | - |
| Staphylococcus epidermidis | - | - | - | - |
| Enterococcus faecalis | + | + | + | + |
| Pseudomonas aeruginosa | - | - | - | - |
| Escherichia coli | - | - | - | - |
| Klebsiella pneumoniae | - | - | - | - |
| Enterobacter cloacae | - | - | - | - |

TABLE 2 (iv)

|  | P2-2 | P2-7 | P2-17 | P4-5 |
|---|---|---|---|---|
| Staphylococcus aureus | - | - | - | - |
| Staphylococcus epidermidis | - | - | - | - |
| Enterococcus faecalis | - | - | - | - |
| Pseudomonas aeruginosa | + | + | + | + |
| Escherichia coli | - | - | - | - |
| Klebsiella pneumoniae | - | - | - | - |
| Enterobacter cloacae | - | - | - | - |

TABLE 2 (v)

|  | EC-24 | EC-34 | EC-39 | EC-625 |
|---|---|---|---|---|
| Staphylococcus aureus | - | - | - | - |
| Staphylococcus epidermidis | - | - | - | - |
| Enterococcus faecalis | - | - | - | - |
| Pseudomonas aeruginosa | - | - | - | - |
| Escherichia coli | + | + | + | + |
| Klebsiella pneumoniae | + | + | + | + |
| Enterobacter cloacae | + | + | + | + |

TABLE 2 (vi)

|  | ET-12 | ET-49 | KI-50 |
|---|---|---|---|
| Staphylococcus aureus | - | - | - |
| Staphylococcus epidermidis | - | - | - |
| Enterococcus faecalis | - | - | - |
| Pseudomonas aeruginosa | - | - | - |
| Escherichia coli | + | + | + |
| Klebsiella pneumoniae | + | + | + |
| Enterobacter cloacae | + | + | + |

Apparently from Table 2 above, each probe have reacted only with DNA obtained from origin strain (or relative strain thereof) and not reacted (hybridized) with any DNA obtained from strains except for strains from the origin strain, therefore, their specificity have been confirmed.

EXAMPLE 3

Analysis of Base Sequence

Base sequence of DNA probes (total 23 probes) of the present invention, which have been confirmed their specificity to the origin species in the Examples 1 and 2, were sequenced according to the following method.

(1) Preparation of Plasmid DNA

*Escherichia coli* K-12, JM109 transformants, wherein the subcloned insert fragments (to be seqeuenced) is contained in pGem-3Z (Promega), was inoculated in 5 ml of Luria-Bactani Medium (bacto-tryptone, 10 g/1 L; bacto-yeast extract, 5 g/1 L; NaCl, 10 g/1 L; adjusted pH to 7.0 with 5N NaOH) and cultivated overnight.

Culture liquid was centrifuged (5,000 rpm, 5 min.) and collected the bacteria. 100 μl of solution of 50 mM glucose/ 50 mM Tris-HCl (pH8.0)10 mM EDTA containing 2.5 mg/ml of lysozyme (Sigma) was added to precipitate, and left at room temperature for five minutes. 0.2M NaOH solution containing 1% of sodium dodecyl sulfate (Sigma) was added to the suspension so obtained and mixed therewith. 150 μl of 5M pottasium acetate solution (pH 4.8) was further added thereto and mixed therewith, then iced for 15 minutes.

Supernatant obtained by centrifugation (15,000 rpm, 15 min.) was treated with phenol/CHCl₃ and added thereto ethanol of two times volume, then precipitate was obtained by centrifugation (12,000 rpm, 5 min.). This precipitate was dissolved in 100 μl of solution of 10 mM Tris-HCl (pH7.5) /0.1 mM EDTA and added thereto 10 mg/ml RNaseA (Sigma) solution, then left it at room temperature for 15 minutes.

300 μl of 0.1M sodium acetate solution (pH 4.8) was added to this preparation and treated with phenol/CHCl₃, then precipitate was obtained by adding ethanol to supernatant. DNA samples were prepared by drying this precipitate and dissolving in 10 μl distilled water.

(2) Pretreatment for Sequencing

Pretreatment for sequencing was performed with Auto-Read™ Sequencing Kit (Pharmasia).

Concentration of DNA to become a template was adjusted to 5–10 μg in 32 μl. 32 μl of template DNA was transferred to 1.5 ml mini-tube (Eppendolf), and added thereto 8 μl of 2M NaOH solution, then mixed gently therewith. After instant centrifugation, it was left at room temperature for 10 minutes.

7 μl of 3M sodium acetate (pH 4.8) and 4 μl a of distilled water, then 120 μl a of ethanol were added thereto then mixed therewith, and left for 15 minutes on dry ice. DNA which have been precipitated by centrifugation for 15 minutes were collected, and supernatant was removed carefully. The precipitate so obtained were washed with 70% ethanol and centrifuged for 10 minutes. Then, the supernatant was removed carefully again and dried the precipitate under the reduced pressure.

The precipitate was dissolved in 10 μl of distilled water, then 2 μl of fluorescent primer (0.42 $A_{260}$ unit/10 ml, 4–6 pmol) (M13 Universal Primer; 5'-Fluorescein-d [CGACGTTGTAAAACGACGGCCAGT]-3' (SEQ ID NO:24) (1.6 pmol/μl; 0.42 $A_{260}$ unit/ml); M13 Reverse Primer, 5'-Fluorescein-d[CAGGAAACAG CTATGAC]-3' (SEQ ID NO:25) (2.1 pmol/μl; 0.42 $A_{260}$ unit/ml] and 2 μl of saline for annealing were added thereto, and mixed gently.

After instant centrifugation, they were heat-treated at 65° C. for 5 minutes and rapidly transferred it to a circumstance of 37° C. and kept the temperature for 10 minutes. After keeping the temperature, it was left at room temperature for 10 minutes or more and centrifugated instantly. Then, samples were prepared by adding thereto 1 μl of an elongation saline and 3 μl of dimethyl sulfoxide.

Four mini-tubes have been identified with one of marks of "A", "C", "G" and "T", and, according to the mark, 2.5 μl of A Mix (dissolved ddATP with dATP, dCTP, $c^7$dGTP and dTTP), C Mix (dissolved ddCTP with dATP, dCTP, $c^7$dGTP and dTTP), G Mix (dissolved ddGTP with dATP, dCTP, $c^7$dGTP and dTTP), or T Mix (dissolved ddTTP with dATP, dCTP, $c^7$dGTP and dTTF) were poured into each identified tube. Each solution was preserved in freezed condition, and the solution was heated at 37° C. for one minute or more to use it.

2 μl of diluted T7DNA polymerase (Pharmacia; 6–8 units/2 μl ) was added to DNA sample, and completely mixed by pipetting or mixing it gently. Immediately after completing the mixing, these mixed solution was poured into 4.5 μl of four-types solution respectively which have kept the certain temperature. Fresh tips were used at the time of pouring.

The solution have been kept for five minutes at 37° C., then 5 μl of termination solution were poured into each reaction-solution. Fresh tips were used for pouring. Immediately after keeping the solution for 2–3 minutes at 90° C., it was cooled on ice. 4–6 μl/lane of the solution was applied to the electrophoresis.

(3) Sequencing on Base Sequence

Sequencing on each base sequence of probes, disclosed in Examples 1 and 2, having the specificity against Staphylococcus aureus or Staphylococcus epidermidis were performed with A.L.F. DNA Sequencer System (Pharmacia) under an electrophoresis condition of 45° C. for 6 hours.

Then, base sequences of the probes (SEQ ID.No.) prepared from each causative bacteria of the infectious diseases and listed in the following table 3 were disclosed in the sequence listing attached hereto.

TABLE 3

| SPECIES | Probes (SEQ ID. No.) |
|---|---|
| Staphylococcus aureus | SA-7 (1), SA-24 (2) |
|  | SA-36 (3), SA-77 (4) |
| Staphylococcus epidermidis | SE-3 (5), SE-22 (6) |
|  | SE-32 (7), SE-37 (8) |
| Enterococcus faecalis | S2-1 (9), S2-3 (10) |
|  | S2-7 (11), S2-27 (12) |
| Pseudomonas aeruginosa | P2-2 (13), S2-7 (14) |
|  | P2-17 (15), P4-5 (16) |
| Escherichia coli | EC-24 (17), EC-34 (18), |
|  | EC-39 (19), EC-625 (20) |
| Klebsiella pneumoniae | KI-50 (23) |
| Enterobacter cloacae | ET-12 (21), ET-49 (22) |

Thereby, genetic information concerning the specific site of each causative bacteria of the infectious diseases (or relative bacteria thereof) have been clarified.

According to probes of the present invention, for example, causative bacteria of the infectious diseases which have incorporated into the phagocyte can be directly detected, and rapidly and exactly identified without proliferating the bacteria. That is to say, according to the diagnosis using the probe of the present invention, identification of the bacteria can be realized with single specimen, then, reduced the necessary time for diagnosis to about one to two day(s), while the conventional method (with low detection rate) required 3–4 days, and improved remarkably the detection rate. Therefore, this invention can provide an objective factors for the treatment of bacteremia, then realize the effective treatment in the early stage of the infectious diseases, and expect to reduce the mortality.

Then, by clarifying the base sequences of probes which specifically react with primary bacteria of the infectious diseases, these probes can be prepared artifically. Further, a part of information on the analyzed base sequences may be used for rapidly diagnosing the causative bacteria by amplifying DNA of causative bacteria of the infectious diseases in the clinical specimen with PCR technique and primers prepared by making use of said information.

Further, by comparing base sequences of Genomic DNA in the clinical specimen with that of the present invention, rapid identification of the species of the causative bacteria of infectious diseases can be realized.

As stated above, the present invention provide desirable probes for diagnosing the infectious diseases, then expect utilities as a factor to prepare primers for PCR and standard sequence for a comparison with Genomic DNA in the clinical specimen, and further expect an effect to provide valuable hints for preparing and developing the other probes which specifically react with causative bacteria of the infectious diseases.

Then, since the base sequences disclosed in the present application was obtained by random-cloning the Genomic DNA of clinical isolates, utilities of the base sequences of the present invention should be extended to the complementary strands thereof.

Further, although it may be thought that DNA obtained from the wild strains contain the mutated portion, apparently from the disclosure of the Examples above, said mutated DNA portion would not affects the utilities to be derived by the present invention comprising the specificity of the probes of the present invention in the hybridization for a diagnosis of the infectious diseases, and an usage of the information on the base sequences disclosed in the present application to design the primers for PCR technique to realize a rapid diagnosis of the infectious diseases.

We claim:

1. A probe composition for detecting *Escherichia coli*, *Klebsiella pneumoniae* or *Enterobacter cloacae* wherein the probe composition consists essentially of (a) the DNA of any one of SEQ ID NOS:17 through 23, or (b) the complement of (a).

2. A method for detecting the presence of *Escherichia coli*, *Klebsiella pneunmniae* or *Enterobacter cloacae* in a sample comprising the steps of contacting nucleic acid from said sample with the probe composition of claim 1 and detecting hybridization of the nucleic acid from said sample with DNA in said probe composition as an indication of the presence of *Escherichia coli*, *Klebsiella pneumoniae* or *Enterobacter cloacae*.

* * * * *

UNITED STATES PATENT AND TRADEMARK OFFICE
CERTIFICATE OF CORRECTION

PATENT NO.   : 5,763,188
DATED        : June 9, 1998
INVENTOR(S)  : Ohno et al.

It is certified that error appears in the above-identified patent and that said Letters Patent is hereby corrected as shown below:

Title page,
Item [54], please delete "PNEUMONIEAE" and insert -- PNEUMONIAE -- therefor.

Figure 5:
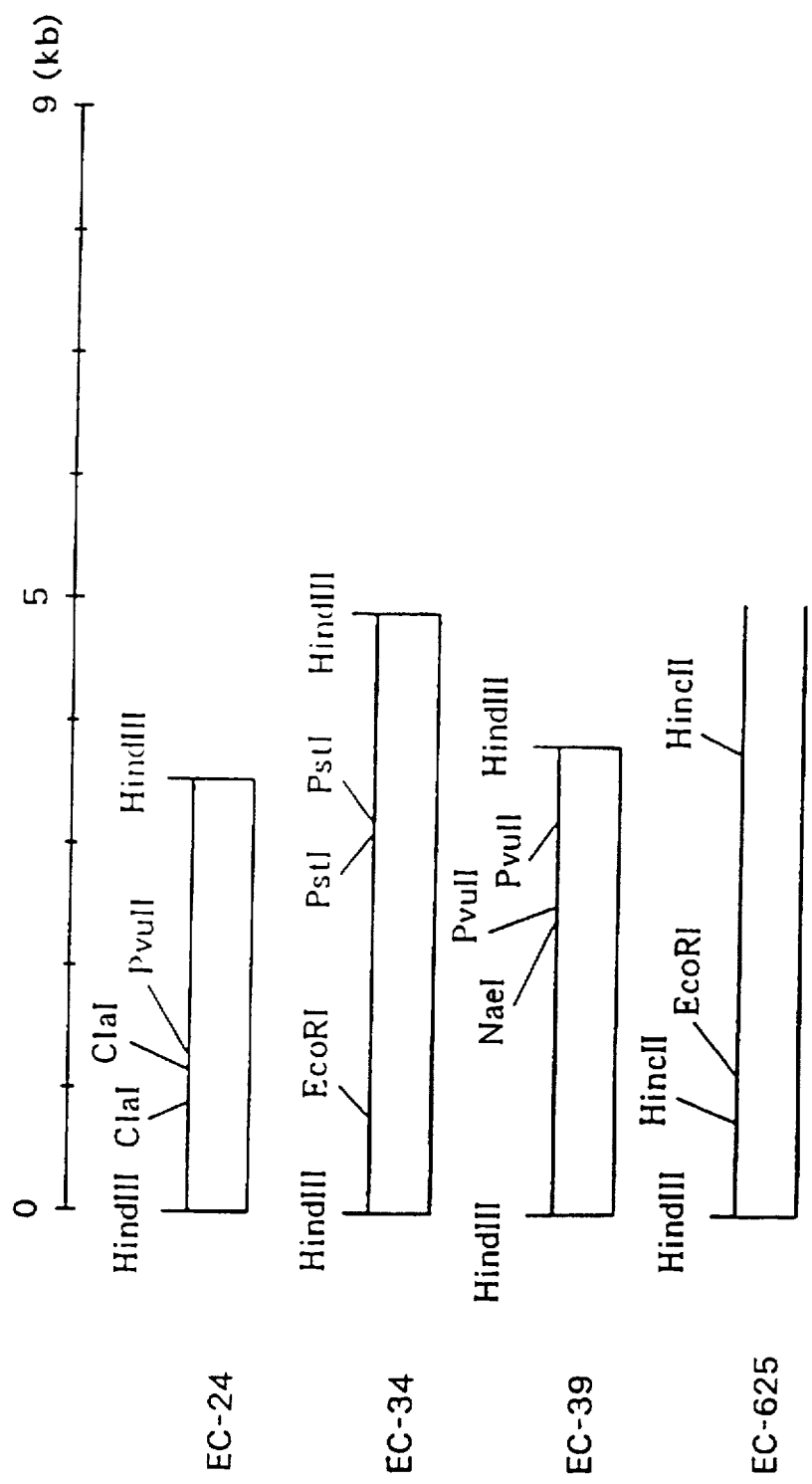
FIG. 5 is a restriction enzyme map of HindIII fragment on probe for detecting Escherichia coli.
Figure 6:
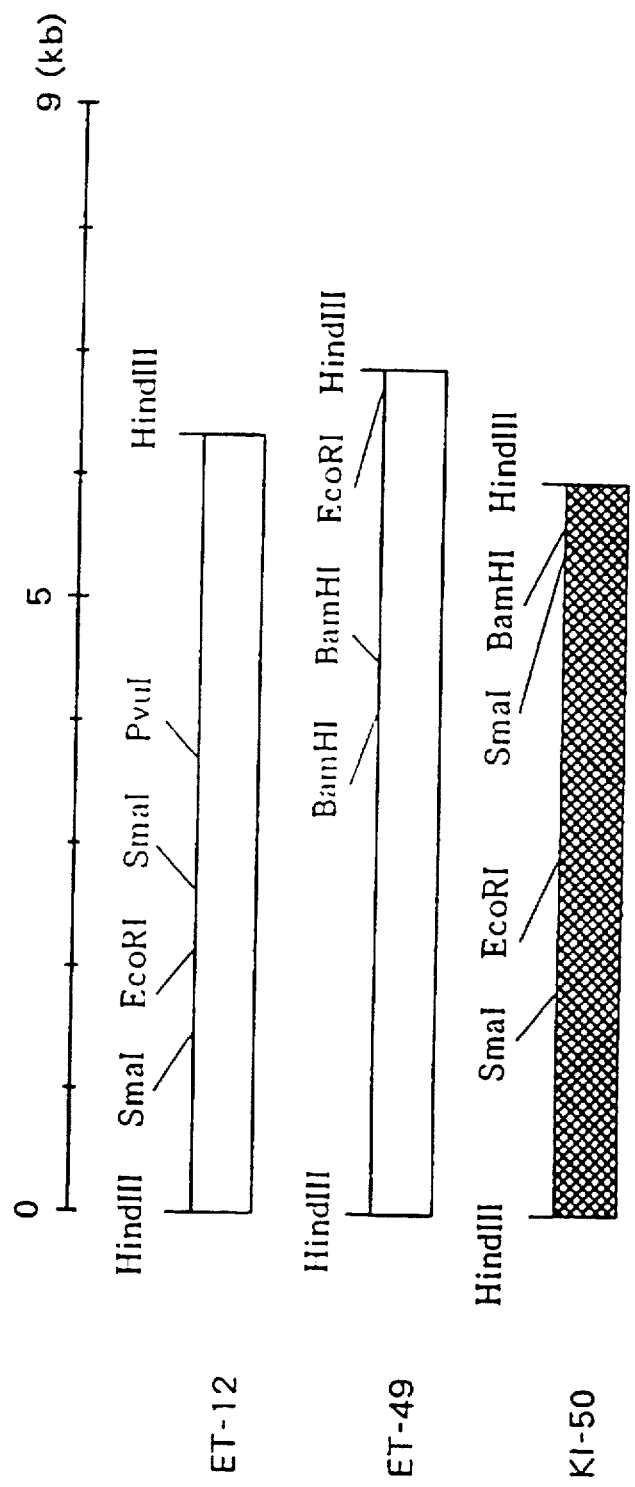
FIG. 6 is a restriction enzyme map of HindIII fragment on probe for detecting Enterobacter cloacae and Klebsiella pneumonia.

Drawings,
Figure 5, please delete   "   "

insert -- 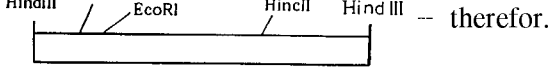 -- therefor.

Column 1,
Line 23, please delete "bateremia" and insert -- bacteremia -- therefor.

Column 2,
Line 39, please delete "*epidermides*" and insert -- *epidermidis* -- therefor.
Line 65, please delete "thier" and insert -- their -- therefor.

Column 4,
Line 9, after "Bacteria" start new paragraph with -- *Escherichia* -- therefor.
Line 58, please delete "acooding" and insert -- according -- therefor.

Column 6,
Line 37, please delete "seqeuenced" and insert -- sequenced -- therefor.
Line 49, please delete "pottasium" and insert -- potassium -- therefor.
Line 67, please delete "(Pharmasia)" and insert -- (Pharmacia) -- therefor.

Column 7,
Line 9, please delete "120 $\mu$l a of ethanol" and insert -- 120 $\mu$l of ethanol -- therefor.
Line 23, please delete "$A_{260}$ unit/ml]" and insert -- 120 $\mu$l unit/ml)] -- therefor.
Line 39, please delete "dTTF)" and insert -- dTTP) -- therefor.

UNITED STATES PATENT AND TRADEMARK OFFICE
CERTIFICATE OF CORRECTION

PATENT NO. : 5,763,188
DATED : June 9, 1998
INVENTOR(S) : Ohno et al.

It is certified that error appears in the above-identified patent and that said Letters Patent is hereby corrected as shown below:

Column 114,
Line 41, please delete "pneunmniae" and insert -- pneumoniae -- therefor.

Signed and Sealed this

First Day of October, 2002

Attest:

Attesting Officer

JAMES E. ROGAN
Director of the United States Patent and Trademark Office